(12) United States Patent
Edman et al.

(10) Patent No.: US 6,706,473 B1
(45) Date of Patent: Mar. 16, 2004

(54) SYSTEMS AND DEVICES FOR PHOTOELECTROPHORETIC TRANSPORT AND HYBRIDIZATION OF OLIGONUCLEOTIDES

(75) Inventors: Carl Frederick Edman, San Diego, CA (US); Michael James Heller, Encinitas, CA (US); Christian Gurtner, La Jolla, CA (US); Rachel Formosa, San Diego, CA (US)

(73) Assignee: Nanogen, Inc., San Diego, CA (US)

( * ) Notice: Subject to any disclaimer, the term of this patent is extended or adjusted under 35 U.S.C. 154(b) by 0 days.

(21) Appl. No.: 09/489,855

(22) Filed: Jan. 24, 2000

Related U.S. Application Data

(63) Continuation-in-part of application No. 09/436,311, filed on Nov. 8, 1999, now Pat. No. 6,569,382, which is a continuation-in-part of application No. 08/760,933, filed on Dec. 6, 1996, now Pat. No. 6,652,808.

(51) Int. Cl.$^7$ .............................. C12Q 1/68; C12Q 1/00; G01N 1/00; G01N 15/00; G01N 33/53
(52) U.S. Cl. .................... 435/6; 435/4; 435/5; 435/7.1; 422/50; 422/68.1
(58) Field of Search .............................. 435/4, 5, 6, 7.1; 422/50, 68.1

(56) References Cited

U.S. PATENT DOCUMENTS

| 3,950,738 A | 4/1976 | Hayashi et al. .............. 365/185 |
| 3,995,190 A | 11/1976 | Salgo .......................... 313/391 |
| 4,032,901 A | 6/1977 | Levinthal .................... 365/118 |

(List continued on next page.)

FOREIGN PATENT DOCUMENTS

| EP | 0228075 | 7/1987 |
| EP | 0229943 | 7/1987 |
| EP | 0617303 | 9/1994 |

(List continued on next page.)

OTHER PUBLICATIONS

Matthews et al, "Analytical Strategies For Use of DNA Probes", Analytical Biochemistry, 169, 1988, 1–25.

Misiura et al, "Biotinyl & Phosphotyrosinyl Phosphoramidite Derivatives Useful In The Incorporation Of Multiple Reporter Groups On Synthetic Oligonucleotides", Nucleic Acids Research, 18, 15, 1990, 4345–4354.

Yu et al, "High Speed, Self–Passivated In GaAs PIN Photodiode For Microwave Fiber Links", Electron. Lett., 23, 1987, 570–572.

Anand et al., "Pulsed Field Gel Electrophoresis" *Gel Electrophoresis Of Nucleic Acids—A Practical Approach,*. $2^{nd}$ Ed., Eds. D.Rickwood & B.D.Hames (New York:IRL Press), 101–123 (1990).

(List continued on next page.)

*Primary Examiner*—Ardin H. Marschel
(74) *Attorney, Agent, or Firm*—O'Melveny & Myers LLP

(57) ABSTRACT

A platform for photoelectrophoretic transport and electronic hybridization of fluorescence labeled DNA oligonucleotides in a low conductivity electrolyte is described. A chemically stabilized semiconductor photodiode or photoconductor surface is coated with a streptavidin-agarose permeation layer. Micro-illumination of the surface generates photoelectrochemical currents that are used to electrophoretically transport and attach capture strands, preferably biotinylated DNA, to arbitrarily selected locations. The same process is then used to transport and electronically hybridize fluorescence labeled DNA target strands to the previously attached capture strands. Signal detection is accomplished either by a fluorescence scanner or a CCD camera. This represents a flexible electronic DNA assay platform that need not rely on pre-patterned microelectronic arrays.

49 Claims, 52 Drawing Sheets

U.S. PATENT DOCUMENTS

| | | | |
|---|---|---|---|
| 4,563,419 A | 1/1986 | Ranki et al. ................... | 435/6 |
| 4,580,895 A | 4/1986 | Patel ........................... | 356/39 |
| 4,584,075 A | 4/1986 | Goldstein et al. ........... | 204/552 |
| 4,594,135 A | 6/1986 | Goldstein ................... | 204/551 |
| 4,599,303 A | 7/1986 | Yabusaki et al. | |
| 4,728,724 A | 3/1988 | Jones, Jr. et al. ............ | 430/19 |
| 4,731,325 A | 3/1988 | Palva et al. | |
| 4,751,177 A | 6/1988 | Stabinsky ..................... | 435/6 |
| 4,787,963 A | 11/1988 | MacConnell | |
| 4,804,625 A | 2/1989 | Morrison et al. ............. | 435/7 |
| 4,816,418 A | 3/1989 | Mack et al. ................ | 436/518 |
| 4,822,566 A | 4/1989 | Newman ..................... | 422/82 |
| 4,822,746 A | 4/1989 | Walt ........................... | 436/528 |
| 4,824,776 A | 4/1989 | Heller et al. .................. | 435/6 |
| 4,859,583 A | 8/1989 | Heller et al. .................. | 435/7 |
| 4,868,103 A | 9/1989 | Stavrianopoulos et al. .... | 435/5 |
| 4,908,112 A | 3/1990 | Pace .......................... | 210/198 |
| 4,908,453 A | 3/1990 | Cocuzza | |
| 4,996,143 A | 2/1991 | Heller ........................... | 435/6 |
| 5,063,081 A | 11/1991 | Cozzette et al. ............... | 435/4 |
| 5,075,077 A | 12/1991 | Durley, III et al. ........... | 422/56 |
| 5,096,807 A | 3/1992 | Leaback ....................... | 435/6 |
| 5,125,748 A | 6/1992 | Bjornson et al. ........... | 356/414 |
| 5,126,022 A | 6/1992 | Soane et al. ............... | 204/458 |
| 5,143,854 A | 9/1992 | Pirrung et al. .............. | 436/518 |
| 5,164,319 A | 11/1992 | Hafeman et al. ........... | 435/287 |
| 5,166,063 A | 11/1992 | Johnson ...................... | 435/173 |
| 5,200,051 A | 4/1993 | Cozzette et al. ............ | 204/403 |
| 5,202,231 A | 4/1993 | Drmanac et al. ............. | 435/6 |
| 5,219,726 A | 6/1993 | Evans .......................... | 435/6 |
| 5,227,265 A | 7/1993 | Deboer et al. | |
| 5,231,626 A | 7/1993 | Tadokoro et al. ........... | 369/121 |
| 5,234,566 A | 8/1993 | Osman et al. | |
| 5,278,051 A | 1/1994 | Seeman et al. ............... | 435/91 |
| 5,304,487 A | 4/1994 | Wilding et al. ............... | 435/29 |
| 5,312,527 A | 5/1994 | Mikkelsen et al. ......... | 205/777 |
| 5,316,900 A | 5/1994 | Tsujioka et al. ............ | 430/270 |
| 5,346,789 A | 9/1994 | Lewis et al. .................. | 430/19 |
| 5,355,577 A | 10/1994 | Cohn .......................... | 29/592 |
| 5,380,833 A | 1/1995 | Urdea ......................... | 536/22 |
| 5,399,451 A | 3/1995 | Hashida et al. ............... | 430/19 |
| 5,405,783 A | 4/1995 | Pirrung et al. | |
| 5,434,049 A | 7/1995 | Okano et al. .................. | 435/6 |
| 5,466,575 A | 11/1995 | Cozzette et al. | |
| 5,505,700 A | 4/1996 | Leone et al. | |
| 5,561,043 A | 10/1996 | Cantor et al. .................. | 435/6 |
| 5,565,322 A | 10/1996 | Heller ........................... | 435/6 |
| 5,567,811 A | 10/1996 | Misiura et al. | |
| 5,605,662 A | 2/1997 | Heller et al. | |
| 5,632,957 A | 5/1997 | Heller et al. | |
| 5,637,458 A | 6/1997 | Frankel et al. | |
| 5,653,939 A | 8/1997 | Hollis et al. .................. | 422/50 |
| 5,674,743 A | 10/1997 | Ulmer ........................ | 435/287 |
| 5,681,751 A | 10/1997 | Begg et al. | |
| 5,723,345 A | 3/1998 | Yamauchi et al. | |
| 5,741,462 A | 4/1998 | Nova et al. | |
| 5,751,629 A | 5/1998 | Nova et al. | |
| 5,789,167 A | 8/1998 | Konrad | |
| 5,795,714 A | 8/1998 | Cantor et al. | |
| 5,849,486 A | 12/1998 | Heller et al. | |
| 5,874,214 A | 2/1999 | Nova et al. | |
| 5,925,562 A | 7/1999 | Nova et al. | |
| 5,965,410 A | 10/1999 | Chow et al. | |
| 5,965,452 A | 10/1999 | Kovacs | |
| 5,968,745 A | 10/1999 | Thorpe et al. | |
| 5,972,187 A | 10/1999 | Parce et al. | |
| 5,972,692 A | 10/1999 | Hashimoto et al. | |
| 6,017,696 A | 1/2000 | Heller | |
| 6,025,129 A | 2/2000 | Nova et al. | |
| 6,033,546 A | 3/2000 | Ramsey | |
| 6,048,690 A | 4/2000 | Heller et al. | |
| 6,051,380 A | 4/2000 | Sosnowski et al. | |
| 6,251,691 B1 * | 6/2001 | Seul ........................... | 436/534 |
| 6,507,989 B1 | 1/2003 | Bowden et al. | |

FOREIGN PATENT DOCUMENTS

| | | |
|---|---|---|
| GB | 2156074 | 10/1985 |
| GB | 2258236 B | 7/1991 |
| WO | WO 86/03782 | 7/1986 |
| WO | WO 88/08528 | 11/1988 |
| WO | WO 89/01159 | 2/1989 |
| WO | WO 89/10977 | 11/1989 |
| WO | WO 90/01564 | 2/1990 |
| WO | WO 92/04470 | 3/1992 |
| WO | WO 93/09128 | 5/1993 |
| WO | WO 93/21663 | 10/1993 |
| WO | WO 93/22678 | 11/1993 |
| WO | WO 95/07363 | 3/1995 |
| WO | WO 96/01836 | 1/1996 |
| WO | WO 98/28320 A2 | 7/1998 |
| WO | WO 99/29711 A1 | 6/1999 |
| YU | 57087 A | 8/1990 |

OTHER PUBLICATIONS

Anderson et al., "Quantitative Filter Hybridization", *Nucleic Acid Hybridization—A Practical Approach.* Eds. B.D.Hames & S.J.Higgins (Washington D.C.:IRL Press), 73–111 (1985).

Bains, "Setting A Sequence To Sequence A Sequence", *Bio/Technology,* 10, 757–758, Jul. 10, 1992.

Barinaga., "Will 'DNA Chip'Speed Genome Initative?", *Science,* 253, 1489, Sep. 27, 1991.

Bauer et al., "Robotic Nanomanipulation With An SPM In A Networked Computing Environment", website printout, http://alicudi.usc.edu:80, 1–7, Nov. 20, 1997.

Beattie et al., The 1992 San Diego Conference: "Genosensor Technology", *Genetic Revolution,* 1–5, Nov. (1992).

Beltz et al., "Isolation Of Multigene Families & Determination Of Homologics By Filter Hybridization Methods", *Methods In Enzymology,* 100, 26–285 (1983).

Brown et al. , "Electrochemically Induced Adsorption Of Radio–Labelled DNA On Gold & HOPG Substrates For STM Investigations". *Ultramicroscopy,* 38, 253–264 (1991).

Bugart et al., "Multiplex Polymerase Chain Reaction", *Modern Pathology,* 5, (3), 320–323, May, 1992.

Callahan et al., "Alignable Liftoff Transfer Of Device Arrays Via A Single Polymeric Carrier Membrane", *Electronics Letters,* 29, 951–953, May 27, 1993.

Cardullo et al., "Detection Of Nucleic Acid Hybridization With Synthetic Olgonucleotides", *Proc.Natl.Acad.Sci.USA,* 85, 8790–8794, Dec., 1988.

Connor et al., "Detection Of Sickle Cell $\beta^3$–Globin Allele By Hybridization With Synthetic Oligonucleotides". *Proc. Natl.Acad.Sci.USA,* 80, 278–282, Jan., 1983.

Cuberes, "Room Temperature Repositioning Of Individual $C_{60}$ Molecules At Cu Steps: Operation Of A Molecular Counting Device", *Appl.Phys.Lett.,* 69, (20), 3016–3018 (1996).

Dagani, "Putting The Nano Finger On Atoms", *C&EN,* 20–23, Dec. 2, 1996.

Drmanac et al., "Sequencing Of Megabase Plus DNA By Hybridization: A Strategy For Efficient Large Scale Sequencing". *Genomics,* 4, 114–128 (1989).

Drmanac et al., "DNA Sequence Determination By Hybridization: A Strategy For Efficient Large Scale Sequencing". *Science,* 260, 1649–1652, Jun. 11, 1993.

Esener et al., "Punch–Through Current Under Diffusion Limited Injection: Analysis & Applications". *J.Appl.Phys.*, 12, 1380–1387, Aug., 1985.

Esener et al., "Design Considerations For Three–Terminal Optically Addressed MQW Spatial Light Modulators". Presented at The Annual Meeting Of OSA, at Seattle, Wash, Oct., 1986.

Esener et al., "One Dimensional Silicon/PLZT Spatial Light Modulators". *Opt.Eng.*, 26, (5), 406–413, (Also in: *Proc. SPIE Annual Meeting In San Diego*, 8/86), May, 1987.

Fan et al., "Fundamental Bandgap & Schottky Barrier Height Of Quarternary In AlGa As Grown On GaAs". MRS Meeting, Spring, 1992.

Fan et al., "Quantum–Confined Stark Effect Modulators At 1.06 μm On GaAs", accepted for publication, *IEEE Photonics Technology Letter*, 6, (12), 1383–1385, Dec., 1993.

Feldman et al., "A Comparison Of Electrical & Free Space Optical Interconnections" *Appl.Opt.*, 27, 1742–1751 (1998).

Fodor et al., "Light Directed, Spatially Addressable Parallel Chemical Synthesis". *Science*, 251, 767–773 (1991).

Fodor et al., "Multiplexed Biochemical Assays With Biological Chips". *Nature*, 364, 555–556 (1993).

Garner et al., "Absorption Detection In Capillary Electrophoresis By Fluorescence Energy Transfer". *Anal. Chemistry*, 62, (2), 2193–2198, Oct. 15, 1990.

Glazer et al., "Emerging Techniques Physofluor Probes", *Trends In Biochemical Sciences*, 9, (10), 423–427 (1984).

Haddon et al., "The Molecular Electronic Device & The Biochip Computer: Present Status", *Proc.Natl.Acad. Sci.USA*, 82, 1874–1878 (1985).

Halfhill, "New Memory Architectures To Boost Performance", *Byte*, 86–87, Jul., 1993.

Heller, "An Active Microelectronics Device For Multiplex DNA Analysis", *IEEE Engineering In Medicine & Biology*, 15, (2), 100–104, Mar.–Apr., 1996.

Heller et al., "Interaction Of Divalent Manganese Ion With Adenosine Triphosphate & Related Compounds", *Biochemistry*, 9, (25), 4970 (1970).

Heller et al., "Interactions Of Miracil D With Double–Stranded Polyadenylic Acid & Polyuridylic Acid", *Biochemistry*, 13, 1623 (1974).

Heller et al., *Rapid Detection & Infection Of Infectious Diseases*. Eds. Kingsbury et al. (New York: Academic Press), 245–256 (1986).

Heller et al., "Chemiluminescent & Fluorescent DNA Probes In Hybridization Systems", *Rapid Detection & Identification Of Infectious Agents*. Eds. Kingsbury et al. (New York: Academic Press), 345–365 (1985).

Heller et al., "Self–Organizing Structures Based On Functional Synthetic Nucleic Acid Polymers", *Nanotechnology*, 2, 165–171 (1991).

Heller et al., "Micrelectrophoresis For The Separation Of DNA Fragments", *Electrophoresis*, 13, 512–520 (1992).

Heller et al., "Fluorescent Detection Methods In PCR Analysis", *The Polymerase Chain Reaction*. Eds. Mullis et al. (Birkhanuser) (1994).

Hopfield et al., "A Molecular Shift Register Based On Electron Transfer", *Science*, 241, 817–820, Aug. 12, 1988.

Horejsí, "Some Theoretical Aspects Of Affinity Electrophoresis", *Jnl. Of Chromatography*, 1–13 (1979).

Horejsí et al., "Determination Of Dissociation Constants Of Lectin Sugar Complexes By Means Of Affinity Electrophoresis", *Biochemica et Biophysica Acta*, 499, 290–300 (1977).

Iakoubova et al., "Oncogene Amplification Screening By Labeled Primer Multiiplex Polymerase Chain Reaction", *Modern Pathology*, 7, (7), 784–789, Sep., 1994.

Keller et al., *DNA Probes*. (New York: Stockton Press), 104–108 (1989).

Kornberg, *DNA Synthesis*. Eds. William H. Freeman (San Francisco) (1974).

Krishnakumar et al., "Deposition Characterization Of Thin Ferroelectric Lead Lanthaum Zircontate Titanate (PLTZ) Films On Sapphire For Spatial Light Modulators Applications", *IEEE Transactions On Ultrasonics, Ferroelectrics & Frequency Control*, 38, (6), 585–590, Nov., 1991.

Lee et al., "Interfacial Properties Of InAlAs/InGaAs High FETs & MIS Capacitors", *Semiconductor Science & Technology*, 5, 716–720 (1990).

Lin et al., "Two Dimensional Spatial Light Modulators Fabricated In Si/PLTZ", *Appl.Opt*, 29, (11), Apr., 1990.

Mansoonian et al., "A Comparison Of Transmitter Technologies For Digital Free–Space Optical Interconnection", Submitted To *Applied Optics*, Jul., 1994.

McAlear et al., *Molecular Electronic Devices II*. Eds. Carter (New York: Marcel Dekker), 623–633 (1987).

Mizuno, The Organic Chemistry Of Nucleic Acids (Tokyo: Elsevier), 181–200 (1986).

Morrison et al., "Solution Phasing Detection Of Polynucleotides Using Interacting Fluorescent Labels & Competitive Hybridization", *Anal.Biochem.*, 183, 231–244 (1989).

Moses, "Bioelectronics: Biochips", *Biotechnology: The Science & The Business*, ch 21, 371–378 (1991).

Niemeyer, "DNA As A Materal For Nanotechnology", *Agnew Chem.Int.Ed.Engl.*, 36, 585–587 (1997).

Palecek, "New Trends In Electrochemical Analysis Of Nucleic Acids", *Bioelectrochemistry & Bioenergetics*, 20, 179–194 (1988).

Ranki et al., "Sandwich Hybridization As A Convenient Method For Detection Of Nucleic Acids In Crude Samples", *Gene*, 21, 77–85 (1983).

Requicha, "Nanorobotics", web site printout, http://alicudi.usc.edu:80, 1–13, Nov. 20, 1997.

Robinson et al., "The Design Of A Biochip: A Self–Assembling Molecular Scale Memory Device", Protein Eng., 1, 295–300 (1987).

Saiki, "Amplification Of Genomica DNA", *PCR Protocols: A Guide To Methods & Applications*. (Academic Press), 13–20 (1990).

Shih et al., "Quantum–Confined Stark Effective Modulatos On GaAs Substrates", *Electronic Letters*, 30, (20), Sep., 1994.

Shih et al., "Integration Of InAlGaAs./InGaAs MODFET's On MQW Modulators On GaAs Substrates", *Electronic Letters*, 30, (20), Sep., 1994.

Southern et al., "Analyzing & Comparing Nucleic Acid Sequences By Hybridization To Arrays Of Oligonucleotides Evaluation Using Experimental Models", *Genomics*, 13, 1008–1017 (1992).

Strezoska et al., "DNA Sequencing By Hybridization: 100 Bases Ready By A Non–gel Based Method", *Proc.Natl.Acad.Sci. USA*, 88, 10089–10093 (1991).

Stroscio et al., "Atomic & Molecular Manipulation With The Scanning Tunneling Microscope", *Science*, 254, 1319–1326 (1991).

Tu et al.., "Structure & Stability Of Metal Nucleoside Phosphate Complexes", *Metal Ions & Biological System*, 1, chap 1., Eds. Siegal (New York: Marcel Dekker) (1974).

Uchida et al., "Single Atom Manipulation On The Si(III) 7×7 Surface By The Scanning Tunneling Microscope (STM)". *Surface Science,* 287/288, 1056–1061 (1993).

Wallace et al., "Hybridization of Synthetic Oligodoxyribonucleotides To φx174 DNA: The Effect Of Single Base Pair Mismatch", *Nucleic Acid Res.* 6, (11), 3543–3557 (1979).

Washizu, "Electrostatic Manipulation Of Biological Objects", *Journal of Electrostatics,* 25, 109–123 (1990).

Washizu, "Electrostatic Manipulation Of DNA In Microfabricated Structures", *IEEE Transactions On Industry Applications,* 26, (6), 1165–1172, Nov.–Dec., 1990.

Whitesides et al., "Molecular Self–Assembly & Nanochemistry: A Chemical Synthesis Of Nanostructures". *Science,* 254, 1312–1318 (1994).

Wilke et al., "Use Of Thiazole Orange Homodimer As An Alternative To Ethiduium Bromide For DNA Detection In Agarose Gels", *Modern Pathology,* 7, (3), 385–387, Apr., 1994.

Yu et al., "A Novel In GaAs PIN Photodiode On Semi–Insulating InP", *Optical & Quantum Electronics,* 18, 174–176 (1986).

Yu et al., "Self Aligned Diffusion Technique For N–Imp JFETS", *Electron Lett,* 23, 981–982, 1987.

\* cited by examiner

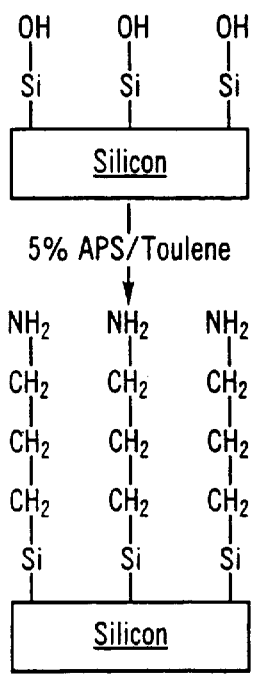
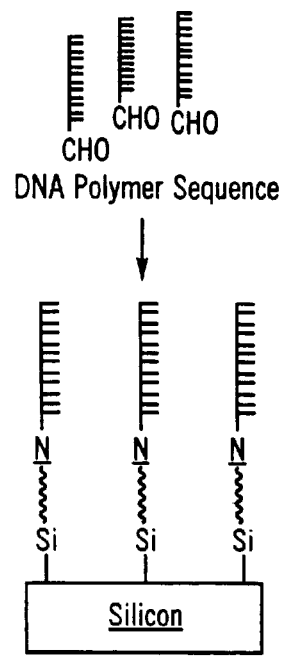
FIG. 4.

PROCESS FOR PREPARING FOUR ID DNA WRITE MATERIAL
THE DNA WITH SEQUENCE (A) IDENTITY IS BOUND COVALENTLY TO THE ENTIRE SURFACE

PROCESS FOR PREPARING FOUR ID DNA WRITE MATERIAL
DNA SEQUENCE (B) FUNCTIONALIZED WITH A PSORALEN MOLECULE IS HYBRIDIZED TO SEQUENCE (A) LEAVING AN UNHYBRIDIZED OVERHANG SEQUENCE FOR SUBSEQUENT HYBRIDIZATION

FIG. 11

LOCATION #1 IS MASKED FROM UV EXPOSURE WHILE LOCATIONS 2,3 & 4 ARE EXPOSED ALLOWING THE PSORALEN MOLECULES TO COVALENTLY CROSS-LINK THE (A) AND (B) DNA SEQUENCE.

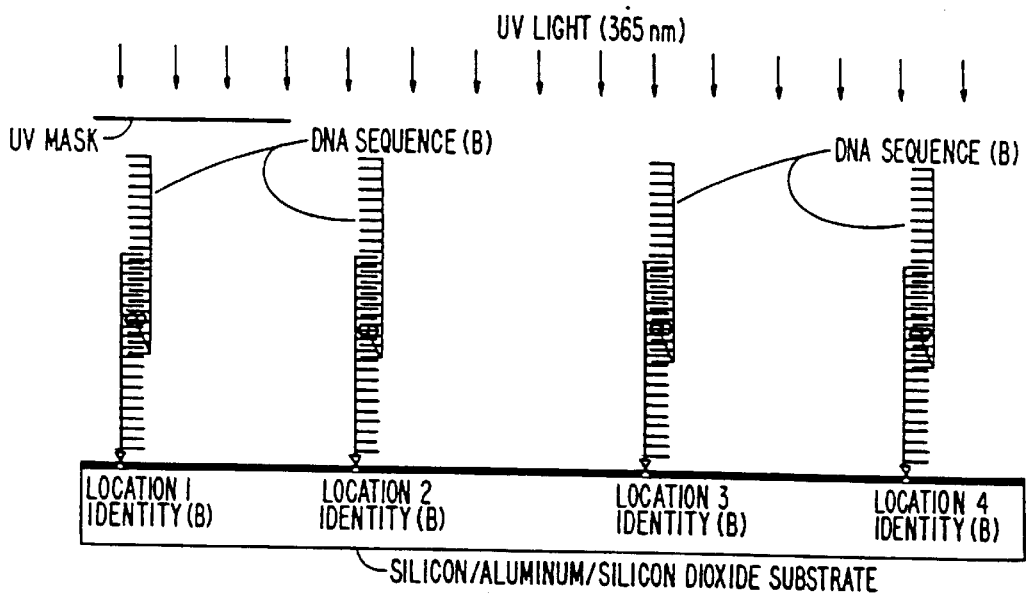

FIG. 12

PROCESS FOR PREPARING FOUR ID DNA WRITE MATERIAL

DEHYBRIDIZATION IS CARRIED OUT TO REMOVE THE NON-CROSSLINKED SEQUENCE (B) FROM THE 1st LOCATION, WHICH NOW HAS A PERMANENT (A) SEQUENCE IDENTITY. DNA SEQUENCE (B) IS NOW COVALENTLY COUPLED TO LOCATIONS 2, 3 AND 4

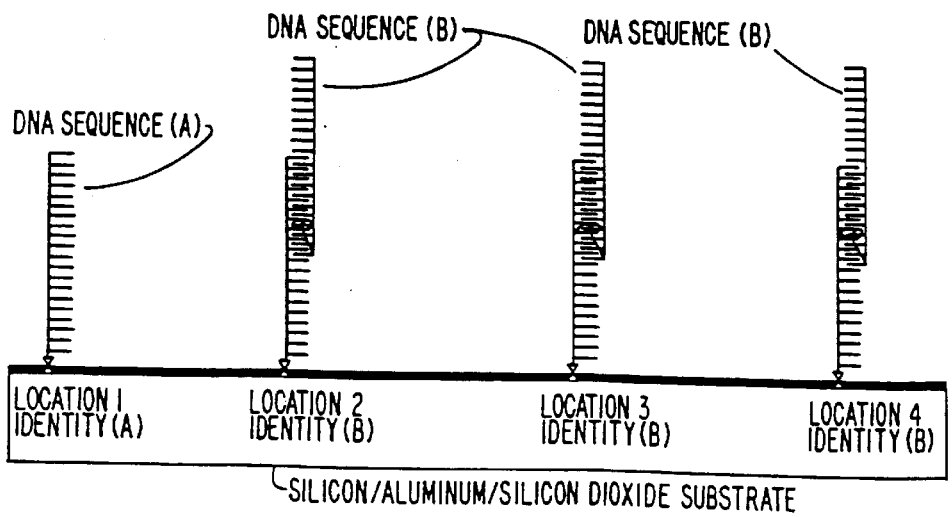

PROCESS FOR PREPARING FOUR ID DNA WRITE MATERIAL

A PSORALEN FUCTIONALIZED DNA SEQUENCE (C) IS NOW HYBRIDIZED TO SEQUENCE (B), AND THE PROCESS IS REPEATED.

PROCESS FOR PREPARING FOUR ID DNA WRITE MATERIAL

LOCATIONS 1 AND 2 ARE NOW MASKED WHILE LOCATIONS 3 AND 4 ARE EXPOSED AFFECTING THE COVALENT CROSS-LINKING OF SEQUENCES (B) AND (C).

PROCESS FOR PREPARING FOUR ID DNA WRITE MATERIAL

DEHYBRIDIZATION IS CARRIED OUT TO REMOVE SEQUENCE (C) FROM LOCATION 2.
A PERMANENT (B) DNA SEQUENCE IDENTITY IS NOW PRESENT AT LOCATION 2

PROCESS FOR PREPARING FOUR ID DNA WRITE MATERIAL

PROCESS FOR PREPARING FOUR ID DNA WRITE MATERIAL

PROCESS FOR PREPARING FOUR ID DNA WRITE MATERIAL

DEHYBRIDIZATION IS CARRIED OUT TO REMOVE DNA SEQUENCE (D) FROM LOCATION 3. A PERMANENT (C) IDENTITY IS PRESENT AT LOCATION 3 AND A PERMANENT (D) IDENTITY IS PRESENT AT LOCATION 4. THIS COMPLETES THE PROCESS FOR PREPARING A FOUR ID DNA WRITE MATERIAL.

PROCESS FOR WRITING TO FOUR ID DNA WRITE MATERIAL

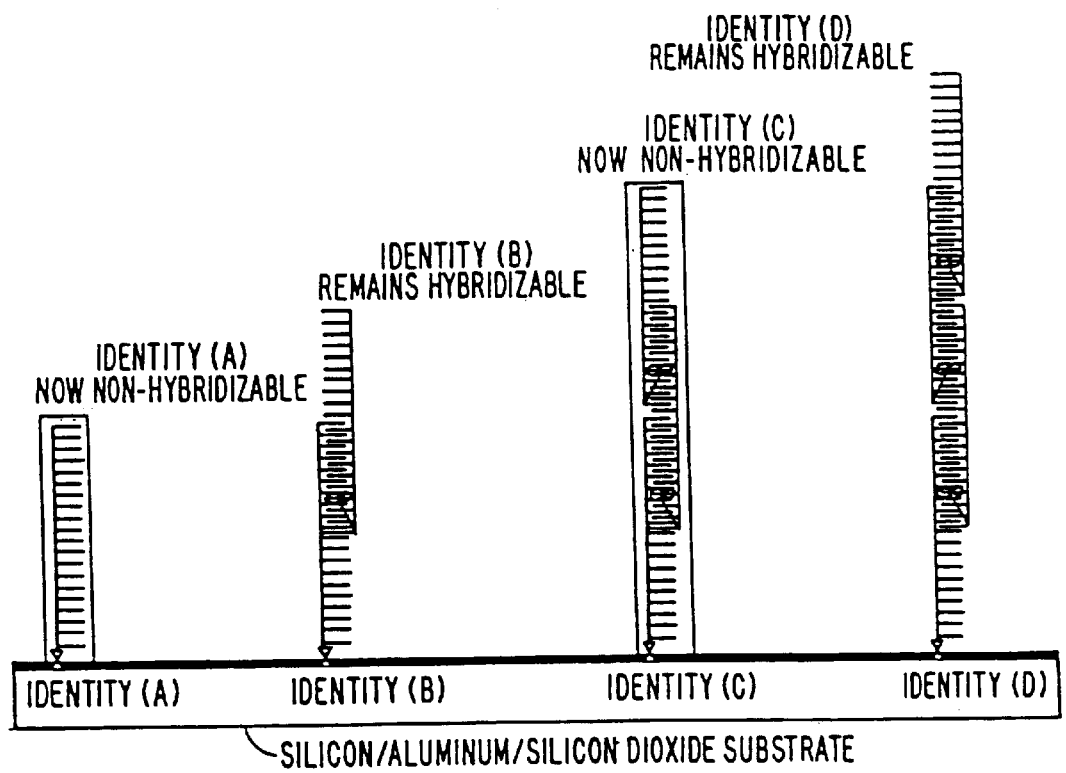

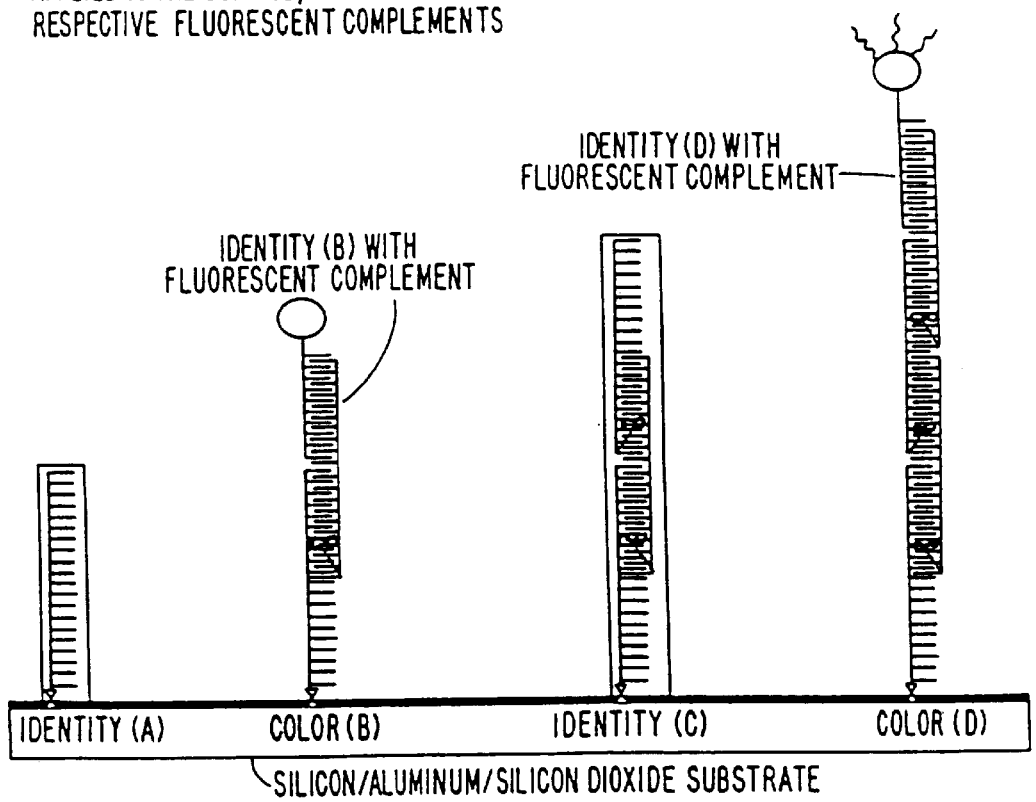

CHIP SURFACE IS FUNCTIONALIZED ONLY WITH APS

ORIGINAL CAPTURE DNA SEQUENCE A, WHICH IS NOT FLUORESCENTLY LABELED, IS COVALENTLY ATTACHED TO THE APS LAYER ON THE CHIP SURFACE

FLUORESCENTLY LABELED COMPLEMENTARY DNA SEQUENCE TO THE (A) IDENTITY ON THE SURFACE IS HYBRIDIZED TO THE ENTIRE CHIP LEAVING THE ENTIRE SURFACE BRIGHT

1/2 OF SURFACE IS UV CROSSLINKED SO WHEN THE BODIPY TEXAS RED LABELED (A) IDENTITY COMPLEMENT IS HYBRIDIZED ACROSS THE ENTIRE CHIP ONLY THE NON-CROSSLINKED RIGHT SIDE OF THE CHIP ATTAINS COLOR

AFTER UV CROSSLINKING THE BODIPY ORANGE LABELED (B) DNA COMPLEMENT IS HYBRIDIZED LEAVING ONLY THE (B) IDENTITY LEFT SIDE OF THE CHIP BRIGHT

AFTER UV CROSSLINKING BOTH (A) AND (B) DNA COMPLEMENTS LABELED WITH THEIR RESPECTIVE FLUOROPHORES ARE HYBRIDIZED TO THE SURFACE, THE LEFT SIDE ATTAINING THE BODIPY ORANGE AND THE RIGHT ATTAINING THE BODIPY TEXAS RED COLOR

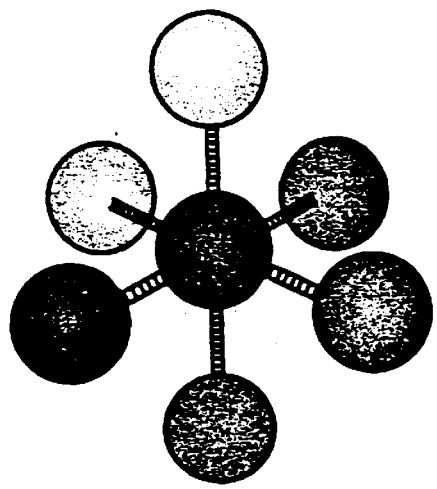
Nanospheres arranged in Octahedron
using 3D DNA nanoconstruction tecniques
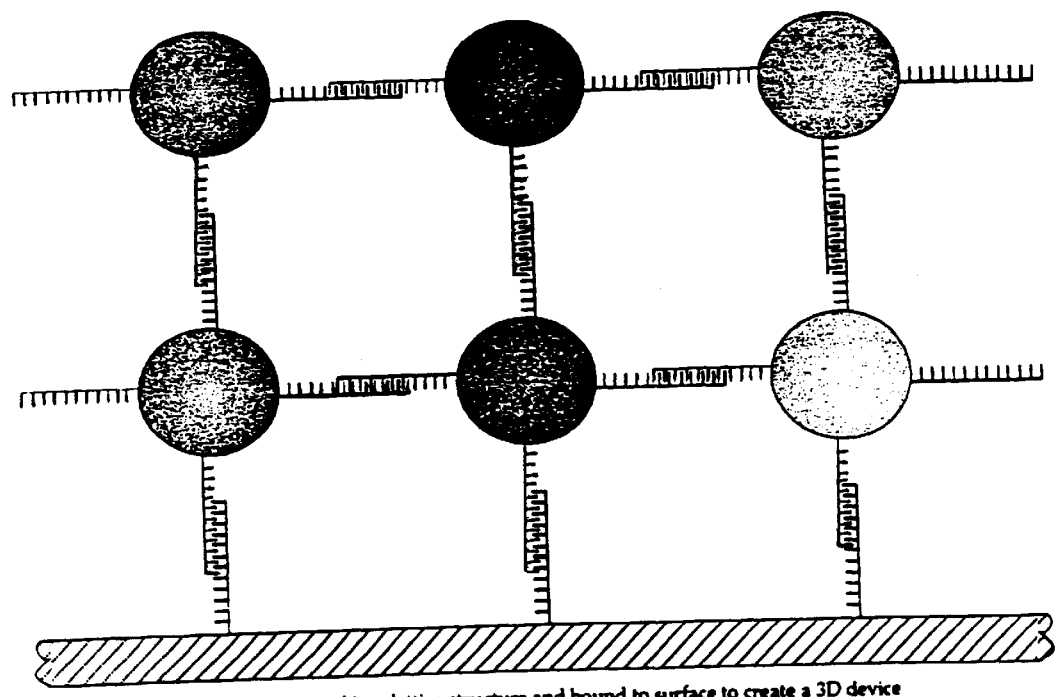
Nanospheres arranged into lattice structure and bound to surface to create a 3D device
FIG. 36

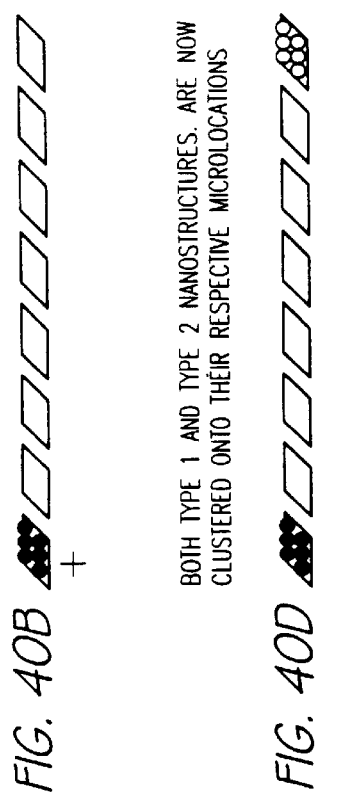

FIG. 40B  TYPE 1 NANOSTRUCTURES ACCUMULATE ON THE POSITIVELY BIASED MICROLOCATION

FIG. 40D  BOTH TYPE 1 AND TYPE 2 NANOSTRUCTURES ARE NOW CLUSTERED ONTO THEIR RESPECTIVE MICROLOCATIONS

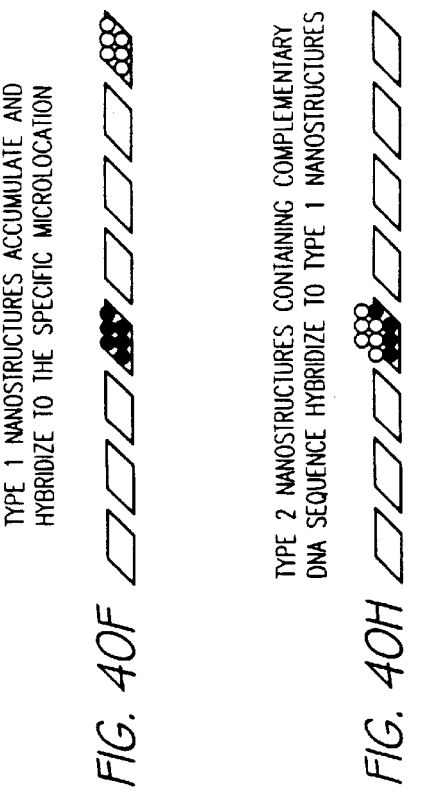

FIG. 40F  TYPE 1 NANOSTRUCTURES ACCUMULATE AND HYBRIDIZE TO THE SPECIFIC MICROLOCATION

FIG. 40H  TYPE 2 NANOSTRUCTURES CONTAINING COMPLEMENTARY DNA SEQUENCE HYBRIDIZE TO TYPE 1 NANOSTRUCTURES

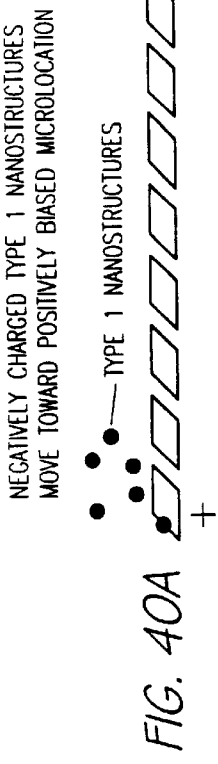

FIG. 40A  NEGATIVELY CHARGED TYPE 1 NANOSTRUCTURES MOVE TOWARD POSITIVELY BIASED MICROLOCATION

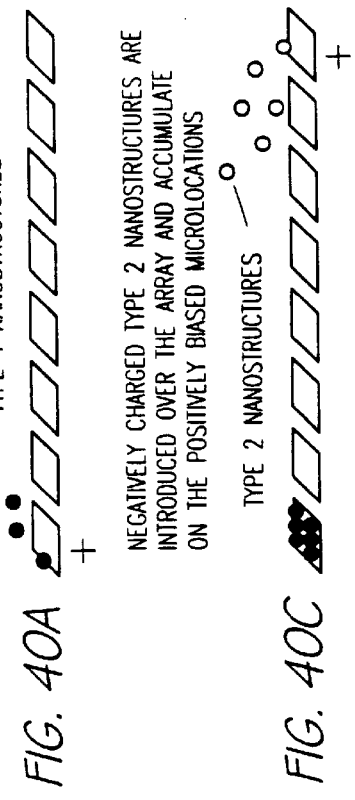

FIG. 40C  NEGATIVELY CHARGED TYPE 2 NANOSTRUCTURES ARE INTRODUCED OVER THE ARRAY AND ACCUMULATE ON THE POSITIVELY BIASED MICROLOCATIONS

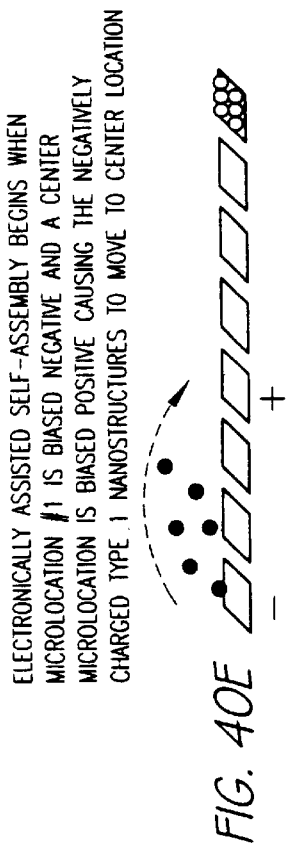

FIG. 40E  ELECTRONICALLY ASSISTED SELF-ASSEMBLY BEGINS WHEN MICROLOCATION #1 IS BIASED NEGATIVE AND A CENTER MICROLOCATION IS BIASED POSITIVE CAUSING THE NEGATIVELY CHARGED TYPE 1 NANOSTRUCTURES TO MOVE TO CENTER LOCATION

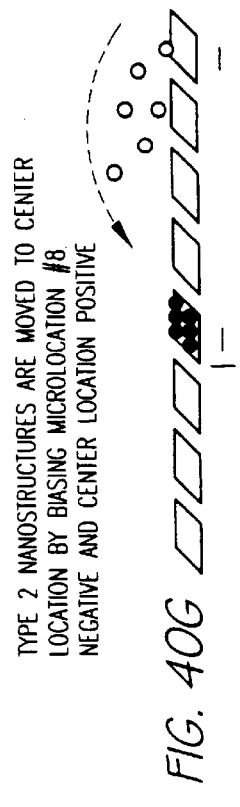

FIG. 40G  TYPE 2 NANOSTRUCTURES ARE MOVED TO CENTER LOCATION BY BIASING MICROLOCATION #8 NEGATIVE AND CENTER LOCATION POSITIVE

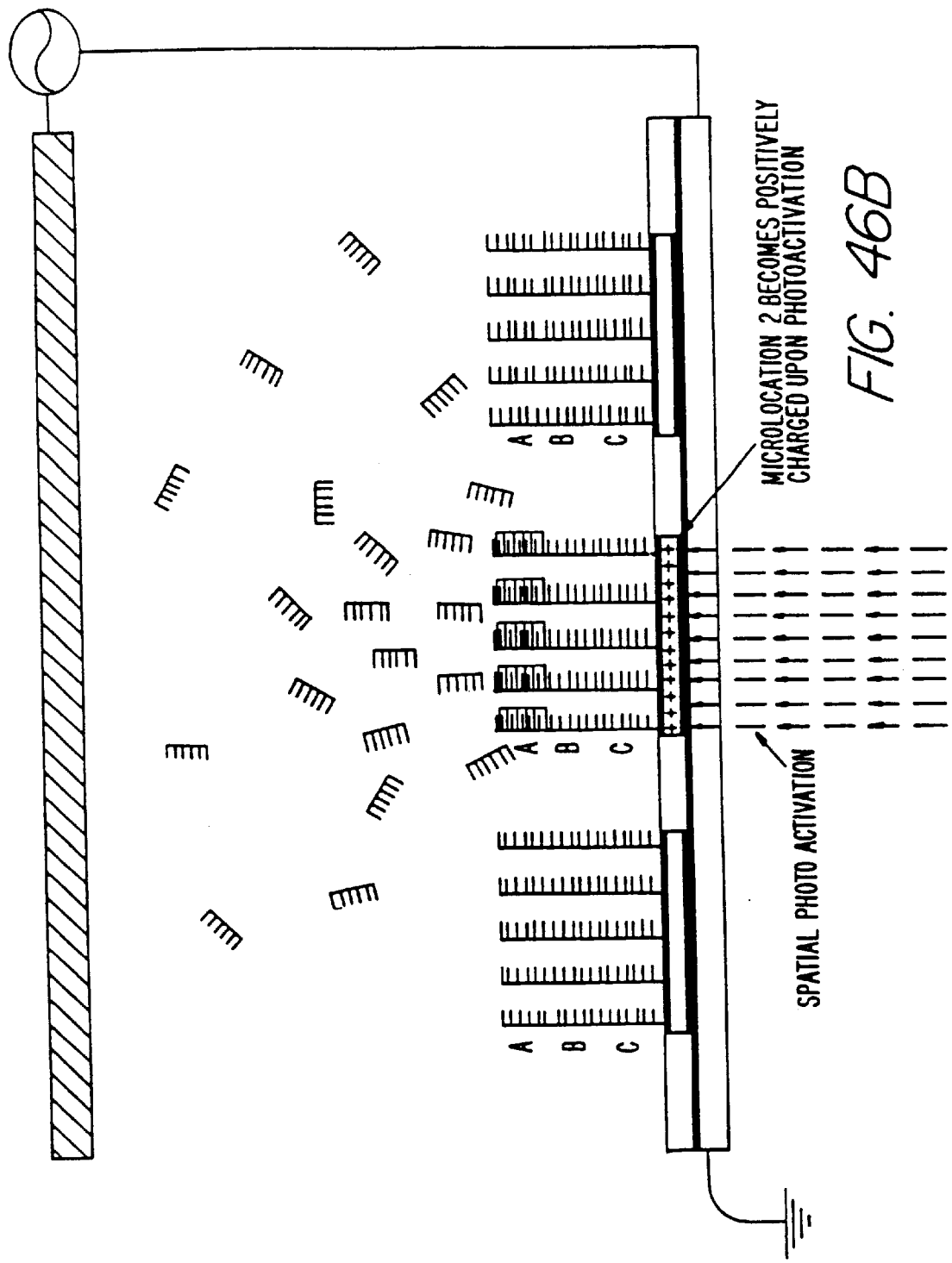

SPATIAL LIGHT ADDRESSING PROCESS COMPLETE

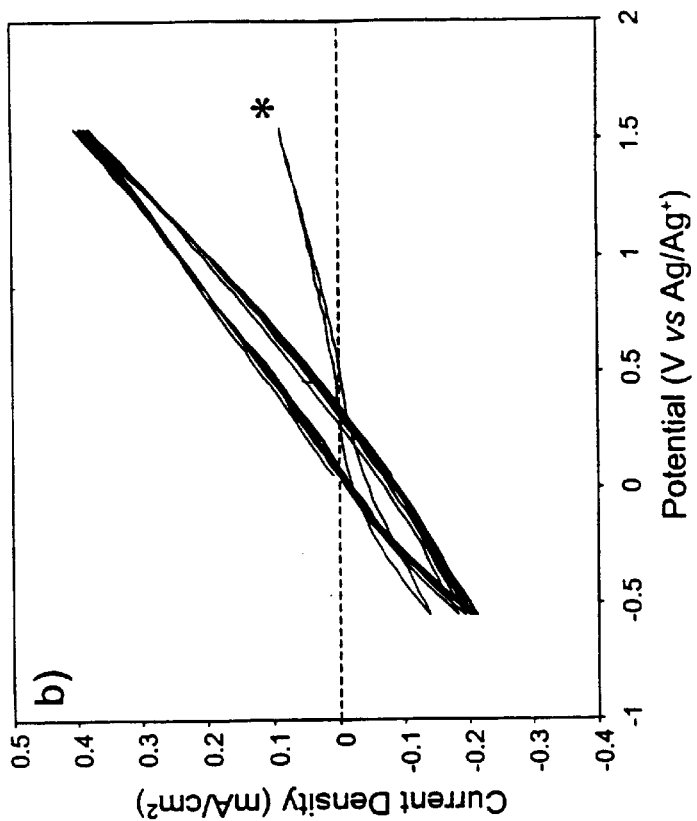
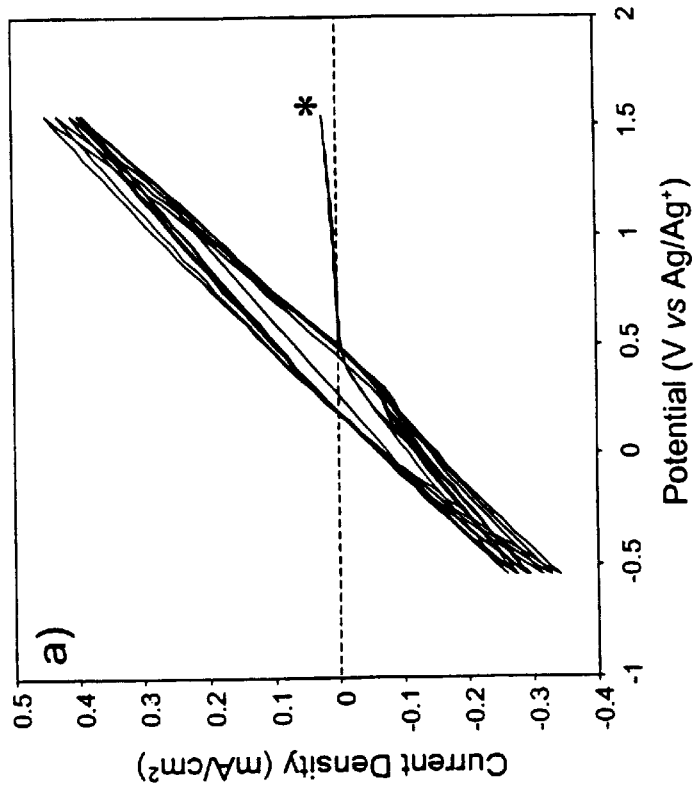
FIG. 49A.
FIG. 49B.

a)
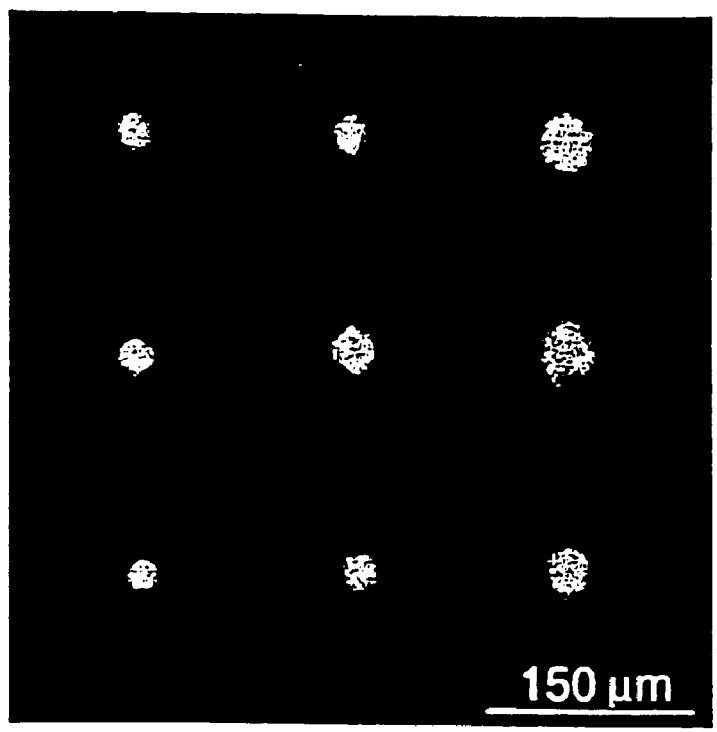
b)
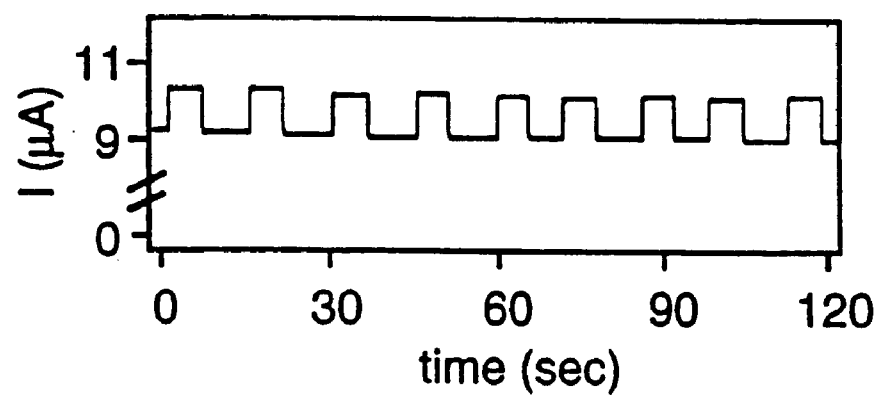
Figure 50

150 μm

SYSTEMS AND DEVICES FOR PHOTOELECTROPHORETIC TRANSPORT AND HYBRIDIZATION OF OLIGONUCLEOTIDES

RELATED APPLICATION INFORMATION

This is a continuation-in-part of application Ser. No. 09/436,311, filed on Nov. 8, 1999, now issued as U.S. Pat. No. 6,569,382, which is a continuation-in-part of application Ser. No. 08/760,933, filed Dec. 6, 1996, now issued as U.S. Pat. No. 6,652,808, all of which are incorporated herein by reference as if fully set forth herein.

FEDERAL FUNDS STATEMENT

At least some support for aspects of the disclosed subject matter was probided by the United States Air Force under grant number F30602-97-C-0229.

1. Field of the Invention

This invention relates to methodologies and techniques which utilize programmable functionalized self-assembling nucleic acids, nucleic acid modified structures, and other selective affinity or binding moieties as building blocks for: (1) creating molecular electronic and photonic mechanisms; (2) for the organization, assembly, and interconnection of nanostructures, submicron and micron sized components onto silicon or other materials; (3) for the organization, assembly, and interconnection of nanostructures, submicron and micron sized components within perimeters of microelectronic or optoelectronic components and devices; (4) for creating, arraying, and manufacturing photonic and electronic structures, devices, and systems; (5) for the development of a high bit density (large byte) three and four dimensional optical data storage materials and devices; and (6) for development of low density optical memory for applications in authentication, anti-counterfeiting, and encryption of information in document or goods. This invention also relates to associated microelectronic and optoelectronic devices, systems, and manufacturing platforms which provide electric field transport and selective addressing of self-assembling, nanostructures, sub-micron and micron sized components to selected locations on the device itself or onto other substrate materials. all incorporated herein by reference as if fully set forth herein.

2. Background of the Invention

The fields of molecular electronics/photonics and nanotechnology offer immense technological promise for the future. Nanotechnology is defined as a projected technology based on a generalized ability to build objects to complex atomic specifications. Drexler, *Proc. Natl. Acad. Sci USA*, 78:5275–5278, (1981). Nanotechnology generally means an atom-by-atom or molecule-by-molecule control for organizing and building complex structures all the way to the macroscopic level. Nanotechnology is a bottom-up approach, in contrast to a top-down strategy like present lithographic techniques used in the semiconductor and integrated circuit industries. The success of nanotechnology may be based on the development of programmable self-assembling molecular units and molecular level machine tools, so-called assemblers, which will enable the construction of a wide range of molecular structures and devices. Drexler, "Engines of Creation," Doubleday Publishing Co., New York, N.Y. (1986).

Present molecular electronic/photonic technology includes numerous efforts from diverse fields of scientists and engineers. Carter, ed., "Molecular Electronic Devices II," Marcel Dekker, Inc, New York, N.Y. (1987). Those fields include organic polymer based rectifiers, Metzger et al., "Molecular Electronic Devices II," Carter, ed., Marcel Dekker, New York, N.Y., pp. 5–25 (1987), conducting conjugated polymers, MacDiarmid et al., *Synthetic Metals*, 18:285 (1987), electronic properties of organic thin films or Langmuir-Blogett films, Watanabe et al., *Synthetic Metals*, 28:C473 (1989), molecular shift registers based on electron transfer, Hopfield et al., *Science*, 241:817 (1988), and a self-assembly system based on synthetically modified lipids which form a variety of different "tubular" microstructures. Singh et al., "Applied Bioactive Polymeric Materials," Plenum Press, New York, N.Y., pp. 239–249 (1988). Molecular optical or photonic devices based on conjugated organic polymers, Baker et al., *Synthetic Metals*, 28:D639 (1989), and nonlinear organic materials have also been described. Potember et al., *Proc. Annual Conf. IEEE in Medicine and Biology*, Part 4/6:1302–1303 (1989).

However, none of the cited references describe a sophisticated or programmable level of self-organizationor self-assembly. Typically the actual molecular component which carries out the electronic and/or photonic mechanism is a natural biological protein or other molecule. Akaike et al., *Proc. Annual Conf. IEEE in Medicine and Biology*, Part 4/6:1337–1338 (1989). There are presently no examples of a totally synthetic programmable self-assembling molecule which produces an efficient electronic or photonic structure, mechanism or device.

Progress in understanding self-assembly in biological systems is relevant to nanotechnology. Drexler, *Proc. Nat. Acad. Sci USA*, 78:5275–5278 (1981), and Drexler, "Engines of Creation," Doubleday Publishing Co., New York, N.Y. (1986). Areas of significant progress include the organization of the light harvesting photosynthetic systems, the energy transducing electron transport systems, the visual process, nerve conduction and the structure and function of the protein components which make up these systems. The so called bio-chips described the use of synthetically or biologically modified proteins to construct molecular electronic devices. Haddonet al., *Proc. Natl. Acad. Sci. USA*, 82:1874–1878(1985), McAlearet al., "Molecular Electronic Devices II," Carter ed., Marcel Dekker, Inc., New York N.Y., pp. 623–633 (1987).

Some work on synthetic proteins (polypeptides) has been carried out with the objective of developing conducting networks. McAlear et al., "Molecular Electronic Devices," Carter ed., Marcel Dekker, New York, N.Y., pp. 175–180 (1982). Other workers have speculated that nucleic acid based bio-chips may be more promising. Robinson et al., "The Design of a Biochip: a Self-Assembling Molecular-Scale. Memory Device," *Protein Engineering*, 1:295–300 (1987).

Great strides have also been made in the understanding of the structure and function of the nucleic acids, deoxyribonucleic acid or DNA, Watson, et al., in "Molecular Biology of the Gene," Vol. 1, Benjamin Publishing Co., Menlo Park, Calif. (1987), which is the carrier of genetic information in all living organisms (See FIG. 1). In DNA, information is encoded in the linear sequence of nucleotides by their base units adenine, guanine, cytosine, and thymidine (A, G, C, and T). Single strands of DNA (or polynucleotide) have the unique property of recognizing and binding, by hybridization, to their complementary sequence to form a double stranded nucleic acid duplex structure. This is possible because of the inherent base-pairing properties of the nucleic acids: A recognizes T, and G recognizes C. This property leads to a very high degree of specificity since any given polynucleotide sequence will hybridize only to its exact complementary sequence.

In addition to the molecular biology of nucleic acids, great progress has also been made in the area of the chemical synthesis of nucleic acids. This technology has developed so automated instruments can now efficiently synthesize sequences over 100 nucleotides in length, at synthesis rates of 15 nucleotides per hour. Also, many techniques have been developed for the modification of nucleic acids with functional groups, including: fluorophores, chromophores, affinity labels, metal chelates, chemically reactive groups and enzymes. Smith et al., *Nature*, 321:674–679 (1986); Agarawal et al., *Nucleic Acids Research*, 14:6227–6245 (1986); Chu et al., *Nucleic Acids Research*, 16:3671–3691 (1988).

An impetus for developing both the synthesis and modification of nucleic acids has been the potential for their use in clinical diagnostic assays, an area also referred to as DNA probe diagnostics. Simple photonic mechanisms have been incorporated into modified oligonucleotides in an effort to impart sensitive fluorescent detection properties into the DNA probe diagnostic assay systems. This approach involved fluorophore and chemilluminescent-labeled oligonucleotides which carry out Förster nonradiative energy transfer. Heller et al., "Rapid Detection and Identification of Infectious Agents," Kingsbury et al., eds., Academic Press, New York, N.Y. pp. 345–356 (1985). Forster nonradiative energy transfer is a process by which a fluorescent donor group excited at one wavelength transfers its absorbed energy by a resonant dipole coupling process to a suitable fluorescent acceptor group. The efficiency of energy transfer between a suitable donor and acceptor group has a $1/r^6$ distance dependency (see Lakowicz et al., "Principles of Fluorescent Spectroscopy," Plenum Press, New York, N.Y., Chap. 10, pp. 305–337 (1983)).

As to photonic devices, they can generally be fabricated in dense arrays using well developed micro-fabrication techniques. However, they can only be integrated over small areas limited by the relatively high defect densities of the substrates employed. In order to be useful and economically viable, these devices must in many cases, be used within large area silicon integrated circuits. A good example of this issue is the vertical cavity surface emitting lasers. To address many potential applications, it would be highly desirable to integrate these devices with large area silicon IC's. A major obstacle in the integration of these new devices with silicon is the existence of material and geometrical incompatibilities. These devices need to be integrated on silicon in large sparse arrays with minimal performance degradation, and without affecting the underlying silicon circuits. Over the past years, a number of component assembly technologies have been extensively investigated regarding the integration of such compound semiconductor devices on silicon. These include hybrid flip-chip bonding or epitaxial lift-off and other direct bonding methods. Although these hybrid technologies have made significant progress and several component demonstrations have shown the viability of these techniques, these methods do not address the problem of geometrical incompatibility. That is, the dimensions with which the specialty devices are fabricated on their mother substrate must be conserved when they are coupled onto the host substrate. This makes the integration of small area devices on large area components economically unfeasible.

A major obstacle in the integration of these new devices with silicon is the existence of material and geometrical incompatibilities. These devices need to be integrated on silicon in large sparse arrays with minimal performance degradation, and without affecting the underlying silicon circuits. Over the past years, a number of component assembly technologies have been extensively investigated regarding the integration of such compound semiconductor devices on silicon. These include hybrid flip-chip bonding or epitaxial lift-off and other direct bonding methods. Although these hybrid technologies have made significant progress and several component demonstrations have shown the viability of these techniques, these methods do not address the problem of geometrical incompatibility. That is, the dimensions with which the specialty devices are fabricated on their mother substrate must be conserved when they are coupled or grafted onto the silicon board.

The prior art has no integration technique that is capable of creating a sparse array of devices distributed over a large area, when the devices are originally fabricated densely over small areas. This makes large area components made up from integration of micron size devices economically unfeasible. To solve this problem, the electronics industry employs a hierarchy of packaging techniques. However, this problem remains unsolved when a regular array of devices is needed on large areas with a relatively small pitch. This problem is probably most noticeable through the high cost associated with the implementation of matrix addressed displays, where the silicon active matrix consists of small transistors that need to be distributed over a large area. Thus, prior art microfabrication techniques limit devices to small area components where a dense array of devices are integrated. However, there are a number of important applications that could benefit from specialty devices being integrated more sparsely over large areas.

One possible method for removing the geometrical limitations is the further development of semiconductor substrate materials to the point where their defect densities approaches that of silicon. This is a long and expensive process that requires incremental progress. A second approach is the development of special robots capable of handling micron and sub-micron size devices and able to graft them to appropriate places. This also seems impractical because the grafting process will remain sequential where one device may be grafted after another, requiring impractical processing times. In any case, both of these approaches may be limited to motherboard dimensions on the order of 10 cm.

With regard to memories, data processing engines have been physically and conceptually separated from the memory which stores the data and program commands. As processor speed has increased over time, there has been a continuous press for larger memories and faster access. Recent advances in processor speed have caused system bottlenecks in access to memory. This restriction is critical because delays in obtaining instructions or data may cause significant processor wait time, resulting in loss of valuable processing time.

Various approaches have been taken to solve these concerns. Generally, the solutions include using various types of memory which have different attributes. For example, it is common to use a relatively small amount of fast, and typically expensive, memory directly associated with the processor units, typically called cache memory. Additionally, larger capacity, but generally slower, memory such as DRAM or SRAM is associated with the CPU. This intermediate memory is often large enough for a small number of current applications, but not large enough to hold all system programs and data. Mass storage memory, which is ordinary very large, but relatively inexpensive, is relatively slow. While advances have been continually made in improving the size and speed of all types of memory, and generally reducing the cost per bit of memory, there remains a substantial need especially to serve yet faster processors.

For the last 20 years most mass storage devices have utilized a rotating memory medium. Magnetic media have been used for both "floppy" (flexible) disks or "hard" disk drives. Information is stored by the presence or absence of magnetization at defined physical locations on the disk. Ordinarily, magnetic media are "read-write" memories in that the memory may be both written to and read from by the system. Data is written to or read from the disk by heads placed close to the surface of the disk.

A more recent development in rotating mass storage media are the optical media. Compact disks are read only memory in which the presence or absence of physical deformations in the disk indicates the data. The information is read by use of a focused laser beam, in which the change in reflectance properties from the disk indicate the data states. Also in the optical realm are various optical memories which utilize magnetooptic properties in the writing and reading of data. These disks are both read only, write once read many ("WORM") drives and multiple read-write memories. Generally, optical media have proved to have a larger storage capacity, but higher costs per bit and limited write ability, as compared with magnetic media.

Several proposals have been made for using polymers for electronic based molecular memories. For example, Hopfield, J. J., Onuchic, J. N. and Beratan, D. N., "A Molecular Shift Register", *Science*, 241, p. 817, 1988, discloses a polymer based shift register memory which incorporates charge transfer groups. Other workers have proposed an electronic based DNA memory (see Robinson et al, "The Design of a Biochip: A Self-Assembling Molecular-Scale Memory Device", *Protein Engineering*, 1:295–300 (1987)). In this case, DNA is used with electron conducting polymers for a molecular memory device. Both concepts for these molecular electronic memories do not provide a viable mechanism for inputting data (write) and for outputting data (read).

Molecular electronic memories have been particularly disappointing in their practical results. While proposals have been made, and minimal existence proofs performed, generally these systems have not been converted to commercial reality. Further, a specific deficiency of the system described above is that a sequential memory is typically substantially slower than a random access memory for use in most systems.

The optical memories described above suffer from the particular problem of requiring use of optical systems which are diffraction limited. This imposes size restrictions upon the minimum size of a data bit, thereby limiting memory density. This is an inherent limit in systems which store a single bit of data at a given physical memory location.

Further, in all optical memory systems described above, the information is stored on a bit-by-bit basis, such that only a single bit of data is obtained by accessing a giving physical location in memory. While word-wide memory access systems do exist, generally they store but a single bit of information at a given location, thereby requiring substantially the same amount of physical memory space whether accessed in a bit manner or word-wide manner.

While systems have generally increased in speed and storage density, and decreased in cost per bit, there remains a clear gap at present between processor speed and system requirements. See generally, "New Memory Architectures to Boost Performance", Tom R. Halfhill, Byte, July, 1993, pp 86 and 87. Despite the general desirability of memories which are faster, denser and cheaper per bit, and the specific critical need for mass memory which can meet the demands of modem day processor systems speed, no completely satisfactory solution has been advanced heretofore. The fundamental limitations on the currently existing paradigms cannot be overcome by evolutionary enhancements in those systems.

Inorganic and organic semiconductors are the materials of choice for the generation of photocurrents or photoelectrochemicalcurrents. Although there are a rich variety of semiconductors suitable for solid state devices (solar cells, photodiodes, photoconductors etc), only a limited number of these are adequate for photoelectrochemical current formation. In addition, there is no single low band-gap semiconductor or compound semiconductor material known that can withstand the corrosive environment present during photooxidation of water. Photooxidation of water, however, is the dominant process at the positive electrode (anode) during electrophoresis of negatively charged DNA in aqueous electrolytes. To overcome this instability, a number of research groups involved in the field of photovoltaic applications have reported on the stabilization of inorganic semiconductor photoanodes against corrosion in water. Variable levels of stabilization were achieved by deposition of protective surface layers such as noble metals, metal oxides or conducting polymers. One report by Kainthla, et al. demonstrated excellent long-term stability of n-type silicon surfaces under conditions of water oxidation. The stabilizing layer in this case was $Mn_2O_3$ that was applied to the silicon surface by a simple solution phase deposition process.

Despite the clear desirability for new and improved apparatus and methods in this field, no optimal solution has been proposed previously.

SUMMARY OF THE INVENTION

A platform for photoelectrophoretic transport and electronic hybridization of fluorescence labeled DNA oligonucleotides in a low conductivity electrolyte is described. A chemically stabilized semiconductor photodiode or photoconductor surface is coated with a streptavidin-agarose permeation layer. Micro-illumination of the surface generates photo-electrochemical currents that are used to electrophoretically transport and attach capture strands, preferably biotinylated DNA, to arbitrarily selected locations. The same process is then used to transport and electronically hybridize fluorescence labeled DNA target strands to the previously attached capture strands. Signal detection is accomplished either by a fluorescence scanner or a CCD camera. This represents a flexible electronic DNA assay platform that need not rely on pre-patterned microelectronic arrays.

Increasingly, the technologies of communication, information processing, and data storage are beginning to depend upon highly-integrated arrays of small, fast electronic and photonic devices. As device sizes scale down and array sizes increase, conventional integration techniques become increasingly costly. The dimensions of photonic and electronic devices permit the use of molecular biological engineering for the integration and manufacturing of photonic and electronic array components. This invention relates to methodologies and manufacturing techniques which utilize programmable functionalized self-assembling nucleic acids, nucleic acid modified structures, and other selective affinity or binding moieties as building blocks for: (1) creating molecular electronic and photonic mechanisms; (2) for the organization, assembly, and interconnection of nanostructures, submicron and micron sized components onto silicon or other materials; (3) for the organization, assembly, and interconnection of nanostructures, submicron and micron sized components within perimeters of microelectronic or optoelectronic components and devices; (4) for creating, arraying, and manufacturing photonic and electronic structures, devices, and systems; (5) for the development of a high bit density (large byte) three and four dimensional optical data storage materials and devices; and (6) for development of low density optical memory for applications in authentication, anti-counterfeiting, and encryption of information in documents or goods. This invention also relates to associated microelectronic and optoelectronic devices, systems, and manufacturing platforms which provide electric field transport and selective addressing of self-assembling, nanostructures, sub-micron and micron size components to selected locations on the device itself or onto other substrate materials.

Functionalized nucleic acids based polymers (e.g., DNA, RNA, peptide nucleic acids, methyphosphonates) constitute a vehicle to assemble large numbers of photonic and electronic devices and systems, utilizing the base-pair coding property of the DNA which allows specific complementary double stranded DNA structures to be formed. This unique property of DNA provides a programmable recognition code (via the DNA sequence) which can be used for specific placement and alignment of nanostructures.

In the preferred embodiment, the process by which photonic devices would be aligned, involves first coating them with a specific DNA sequence. The area of the host substrate where attachment of the devices is desired are coated with the specific complementary DNA sequence. The substrate and DNA-covered devices are released into a solution and hybridization between complementary DNA strands occurs. Hybridization effectively grafts the devices to their proper receptor locations on the substrate.

More broadly, the invention in this respect relates to a method for the fabrication of micro scale and nanoscale devices comprising the steps of: fabricating first component devices on a first support, releasing at least one first component device from the first support, transporting the first component device to a second support, and attaching the first component device to the second support.

Some potential applications for these techniques are: (1) fabricating light emitter arrays over large surfaces; (2) assembly of two or three-dimensional photonic crystal structures; and (3) manufacturing of various hybrid-integrated components including flat panel displays, medical diagnostic equipment and data storage systems.

As photonics plays an increasingly important role in information processing, communication and storage systems it will deliver faster, smaller, more power efficient, and functionally versatile integrated systems at lower cost. New fabrication technologies including nanostructure fabrication, integration and self-assembly techniques are used. As device dimensions shrink to submicron levels, it becomes important to utilize the inventive concepts employing molecular biological engineering concepts and principles as manufacturing techniques for the fabrication of integrated photonic and electronic devices.

These inventions relate to nanostructures, submicron and micron-sized structures incorporating synthetic DNA polymers. This includes DNA modified with small chromophore molecules, to large structures (e.g., micron-sized) which are modified with DNA sequences. Synthetic DNA polymers can be designed with highly specific binding affinities. When covalently attached to nanoscale organic and metallic structures or micron scale semiconductor component devices, DNA polymers can provide a self-assembly fabrication mechanism. This mechanism can be used for both the selective grafting of the devices to specific pre-programmed locations on a desired surface, and for the clustering of devices into pre-programmed 2-D or 3-D lattices. For grafting of photonic or electronic component devices onto host substrates, DNA polymers with complementary sequences are first synthesized. The photonic component devices and desired areas of the host substrate (receptor areas) are coated with the complementary DNA sequences. The host substrates are then introduced into a solution.

In one aspect of this invention, a method for fabrication of nanoscale and microscale structures is provided comprising the steps of providing a structure with multiple affinity surface identities, orienting the structure in an electric field, and reacting the oriented structure with an affinity site.

In yet another aspect of this invention, a method for forming a multiple identity substrate material is provided comprising the steps of: providing a first affinity sequence at multiple locations on a support, providing a functionalized second affinity sequence, which reacts with the first affinity sequence, and has an unhybridized overhang sequence, and selectively cross-linking first affinity sequences and second affinity sequences.

In yet another aspect of this invention, a method for the assembly of chromophoric structures is provided comprising the steps of: selectively irradiating a photoactivatable region, whereby an electric field is generated corresponding to the region, providing charged reactants in solution which includes the electric field, and repeating the selective irradiation to sequentially assemble the chromophoric structures.

It is an object of this invention to enable nanotechnology and self-assembly technology by the development of programmable self-assembling molecular construction units.

BRIEF DESCRIPTION OF THE DRAWINGS

FIG. 4 shows a cross-section of an attachment mechanism for attaching DNA to silicon.

FIG. 11 is a cross-sectional view of a step in the process for preparing DNA write materials.

FIG. 12 is a cross-sectional view of a step in the process for preparing DNA write materials.

FIG. 21 is a cross-sectional view of a step in the process for preparing DNA write materials.

FIG. 22 is a cross-sectional view of a step in the process for preparing DNA write materials.

FIG. 36 shows structures for the formation of nanodevices, providing an octahedron using 3-D DNA nano-construction techniques (top) and nanospheres arranged into lattice structure and bound to surface to create a 3-D device (lower).

FIGS. 40A–H show the larger environment of FIG. 39.

FIGS. 46A–F show steps in a spacial light addressing process.

FIGS. 49A and B. Current-voltage characteristics of $Mn_2O_3$ coated n-type silicon electrodes measured in 50 mM L-histidine solutions. The ten consecutive cyclic voltammograms acquired in the dark (*) and under illumination were measured a) before and b) after deposition of the streptavidin-agarose permeation layer. The scan rate was 100 mV/sec. (Electrochemical potentials were not compensated for ohmic potential drops across the low conductivity electrolyte.).

FIGS. 50A and B. a) Image of an array of fluorescent spots that was produced by photoelectrophoretic transport and biotin-streptavidin mediated immobilization of fluorescence labeled DNA oligonucleotides on a streptavidin-agarose and $Mn_2O_3$ coated amorphous silicon electrode. Individual spots were illuminated for 5 sec at a light intensity of 4 W (630 nm) and an applied electrochemical potential of 1.5 V. b)Photo-current transient recorded during formation of the array.

IMPORTANT ASPECTS OF DNA STRUCTURE, PROPERTIES, AND SYNTHESIS

Figure 1B:
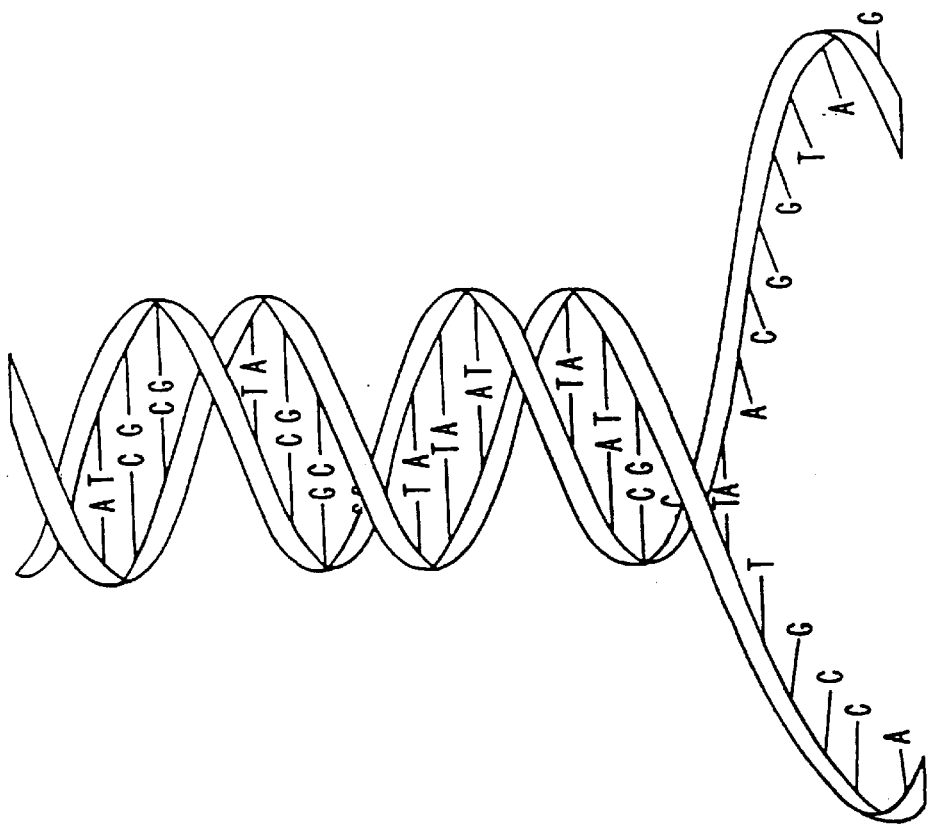
FIGS. 1A and 1B shows show DNA (SEQ ID NOS: 9 and 10) structure and its related physical dimensions.
Figure 1A:
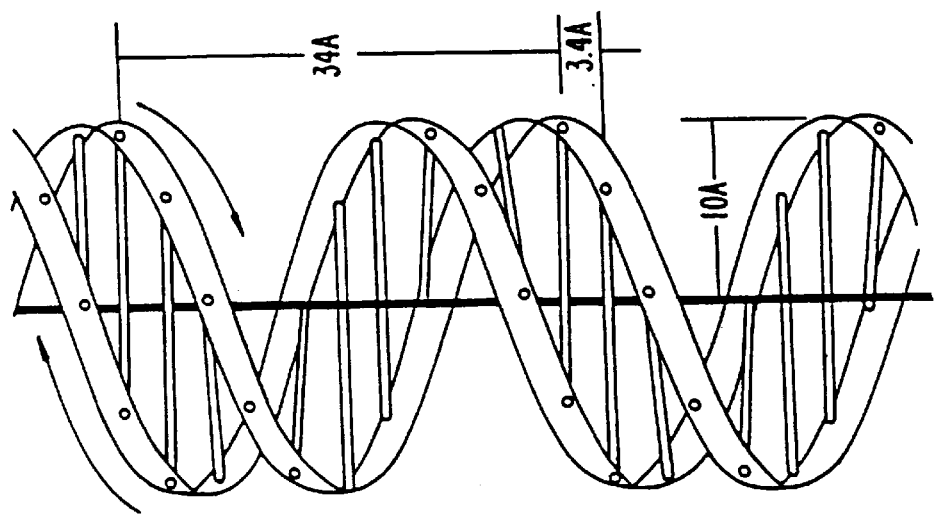

Synthetic DNA possesses a number of important properties which make it a useful material for the applications of these inventions. The most important are the molecular recognition (via base pairing) and self-assembly (via hybridization) properties which are inherent in all DNA molecules. Other important advantages include the ability to easily synthesize DNA, and to readily modify its structure with a variety of functional groups. We have extensively investigated the photonic and electronic energy transfer mechanisms in self-assembled arrangements of synthetic DNA functionalized with a wide variety of donor and acceptor chromophore groups. We have paid particular attention to the basic problems involved in communicating or getting information in and out of these molecular structures. This basic work is now being applied to potential applications for high density optical storage materials, which have been designed to absorb light energy at a single wavelength and re-emit at predetermined multiple wavelengths. We are also now using DNA polymers for the two and three dimensional organization of micron and submicron sized structures on silicon surfaces. This work is being directed at the development of novel optoelectronic devices.

The DNA molecule is considered important to this invention and the proposed applications because it is inherently programmable and can self-assemble. Designing, synthesizing, and organizing these systems requires nanometer range control which few other synthetic polymer systems can match. Additionally, DNA molecules are relatively stable and have a number of other attributes which make them a preferred material for nanofabrication.

The underlying technology for DNA and other nucleic acid type polymers comes from the enormous effort that has been invested over the past fifteen years in synthetic nucleic acid chemistry. Molecular biologists have refined techniques and DNA materials in their pursuit of diagnostics, genetic sequencing, and drug discovery. The basic chemistry for the efficient synthesis of DNA, its modification, its labeling with ligands and chromophores, and its covalent linkage to solid supports are now well developed technologies. Synthetic DNA represents the preferred material into which so many important structural, functional, and mechanistic properties can be combined.

DNA polymers have three important advantages over any of the present polymeric materials used for electronic and photonic applications. First, DNA polymers provide a way to encode highly specific binding-site identities o semiconductor or photonic surfaces. These sites, produced at defined locations, could be of microscopic (micron), sub-micron, or even molecular (nanometer) dimension. Second, DNA polymers provide a way to specifically connect any of these locations. The pre-programmed DNA polymers self-organize automatically. Finally, DNA polymers provide the building blocks for nanotechnology; they are self-organizing materials for creating true molecular-level electronic and photonic devices.

The specificity of DNA is inherent in the hydrogen bonding properties of the base components (Adenine bonds only with Thymine, and Guanine bonds only with Cytosine). These specific base pairing properties of DNA allow complementary sequences of DNA to "hybridize" together to form the double-stranded structure. It is this inherent property which allows DNA polymers to be used to form programmable self-assembling structures. Thus, when a photonic device has one specific DNA polymer sequence attached to it, it will only bind (hybridize) to a device or surface coated with the complementary DNA polymer sequence. Since a large variety of DNA sequences can be used, multiple devices, each attached to a different DNA sequence can in principle be self-assembled simultaneously. The following lists the important advantages of using DNA polymers for self-assembling nanofabrication applications:

1. DNA polymers can by synthesized both rapidly and efficiently with automated instruments. Conventional polymer chemistries can be significantly more complex and costly to develop.

2. DNA polymers can be synthesized in lengths from 2 to 150 nucleotides, which is the appropriate size range (1 nm to 60 nm) for self-assembling unit cells.

3. DNA polymers can be synthesized with any desired base sequence, therein providing programmable recognition for an almost unlimited number of specific connections.

4. DNA polymers with unique sequences of as few as ten nucleotides are highly specific and will bind only to their complementary sequence. Thus, the material allows specific connections as small as 3.4 nm to be made between molecular units.

5. DNA polymers can be covalently labeled with fluorophores, chromophores, affinity labels, metal chelates, chemically reactive functional groups and enzymes. This allows important photonic and electronic properties to be directly incorporated into the DNA polymers.

6. DNA polymers can be modified at any position in their sequence, and at several places within the individual nucleotide unit. This provides a means to position functional groups for maximum performance.

7. DNA polymers can be both covalently and non-covalently linked to solid surfaces: glass, metals, silicon, organic polymers, and bio-polymers. These attachment chemistries are both existing and easily developed.

8. The backbone structure of the DNA molecule itself can be highly modified to produce different properties. Thus, there is compatibility with existing semiconductor and photonic substrate materials.

9. Modified DNA polymers can be used to form three-dimensional structures, thus leading to ultra high density secondary storage schemes.

10. DNA polymers can be reversibly assembled and disassembled by cooling and heating, or modified to remain in the assembled state. This is a critical property for self-organizing materials as it allows for more options in the manufacture of resulting systems.

11. The structural and organizational properties of DNA polymers (nucleic acids in general) are well understood and can be easily modeled by simple computer programs. Thus, more complex molecular photonic and electronic devices can be designed.

DETAILED DESCRIPTION OF THE INVENTION

This invention relates to methodologies, techniques, and devices which utilize self-assembling DNA polymers, modified DNA polymers, DNA derivatized structures and other affinity binding moieties for nanofabrication and microfabrication of electronic and photonic mechanisms, devices and systems. This invention also relates to processes which allow multiplex and multi-step fabrication, organization or assembly of modified DNA polymers, DNA derivatized structures, and other types of affinity or charged structures into more complex structures on or within silicon or other surfaces.

For purposes of this invention "DNA polymers" is broadly defined as polymeric or oligomeric forms (linear or three-dimensional) of nucleic acids including: deoxyribonucleic acid, ribonucleic acids (synthetic or natural); peptide nucleic acids (PNA); methyphosphonates; and other forms of DNA in which the backbone structure has been modified to produce negative, positive or neutral species, or linkages other than the natural phosphate ester. Also included are forms of DNA in which the sugar or base moieties have been modified or substituted, and polymeric forms of DNA in which nucleotide or polynucleotide units are interspersed with other units including but not limited to phosphate ester spacer moieties, amino acids, peptides, polysaccharides, synthetic organic polymers, silicon or inorganic polymers, conductive polymers, chromophoric polymers and nanoparticles or nanostructures.

For purposes of this invention "Modified or Derivatized DNA polymers" are broadly defined as nucleic acids which have been functionalized with chemical or biological moieties (e.g., amines, thiols, aldehydes, carboxyl groups, active esters, biotin and haptens) which allow the DNA to be attached covalently or non-covalently to other molecules, structures, or materials. Also included are forms of DNA which have been modified or Derivatized with chromophores, fluorophores, chelates, metal ions, amino acids, peptides, proteins, enzymes, antibodies, or aliphatic or aromatic moieties which change solubility, and moieties which change the net charge on the DNA molecule.

For purposes of this invention "DNA Derivitized structures" are broadly defined as nanostructures (organic, inorganic, biological); nanoparticles (gold, silica, and other inorganic materials); organic or polymeric nanobeads; submicron devices, components, particles, (silicon based devices produced by photolithographyor E-beam lithography); and micron scale devices or particles which have been functionalized with a specific DNA sequence which allows the structure to be specifically attached or interconnected to another structure, device, or to a specific location on a surface.

While the terms "nanostructure" refers to sub-micron sized structures, terms such as "nano" or "micro" are not intended to be limited in the sense that a micron scale device can be functionalized with DNA polymers which technically have lengths of 10–180 nanometers.

The unique properties of DNA provides a programmable recognition code (via the DNA base sequence) which can be used for specific placement and alignment of sub-micron and nanoscale structures. The basic chemistry and technology required to attach specific DNA sequences to organic, semiconductor, and metallic compounds is known to the art and specific chemistries are described for carrying out such applications.

In the preferred embodiment, the process by which photonic devices are aligned and fixed to substrate surfaces, involves first coating them with a specific DNA polymer sequences. The area of the host substrate where attachment of the specific device is desired, would then be coated with the specific complementary DNA sequence. The substrate would be exposed to a solution containing the DNA covered devices, and hybridization between complementary DNA strands allowed to occur. This hybridization process effectively grafts the devices to their proper receptor locations on the substrate surface. This self-assembly fabrication process can be used for, by way of example, (1) the fabrication of light emitter arrays over large surface areas, and (2) the fabrication of two or three-dimensional photonic band-gap crystal structures.

This fabrication technique has major applications in the field of optoelectronics and in the manufacturing of various hybrid-integrated components including flat panel displays, medical diagnostic equipment and data storage systems. Novel devices with very small physical dimensions take advantage of various quantum confinement techniques. In most cases, these devices are preferably distributed over large areas (e.g. smart pixels and displays). Other devices may be brought together in dense regular crystal lattices (e.g. photonic bandgap crystals). In both cases, the physics of the devices are now understood, and viable fabrication techniques of these inventions are required. With regard to new processing techniques, DNA self-assembly technology allows these devices to be constructed.

Integrated photonic and electronic systems utilize the inventive fabrication technologies including nanostructure fabrication, integration, interconnection and self-assembly techniques. For such applications, DNA self-assembly fabrication technology involves the following steps. Synthetic DNA polymers are designed with highly specific binding affinities. When covalently attached to nanoscale organic, metallic or semiconductor component devices, DNA polymers provide a self-assembly fabrication mechanism. This mechanism can be used for both the selective grafting of devices to specific pre-programmed locations on a desired surface, and for the clustering of devices into pre-programmed 2 and 3 dimensional lattices.

Figure 2:
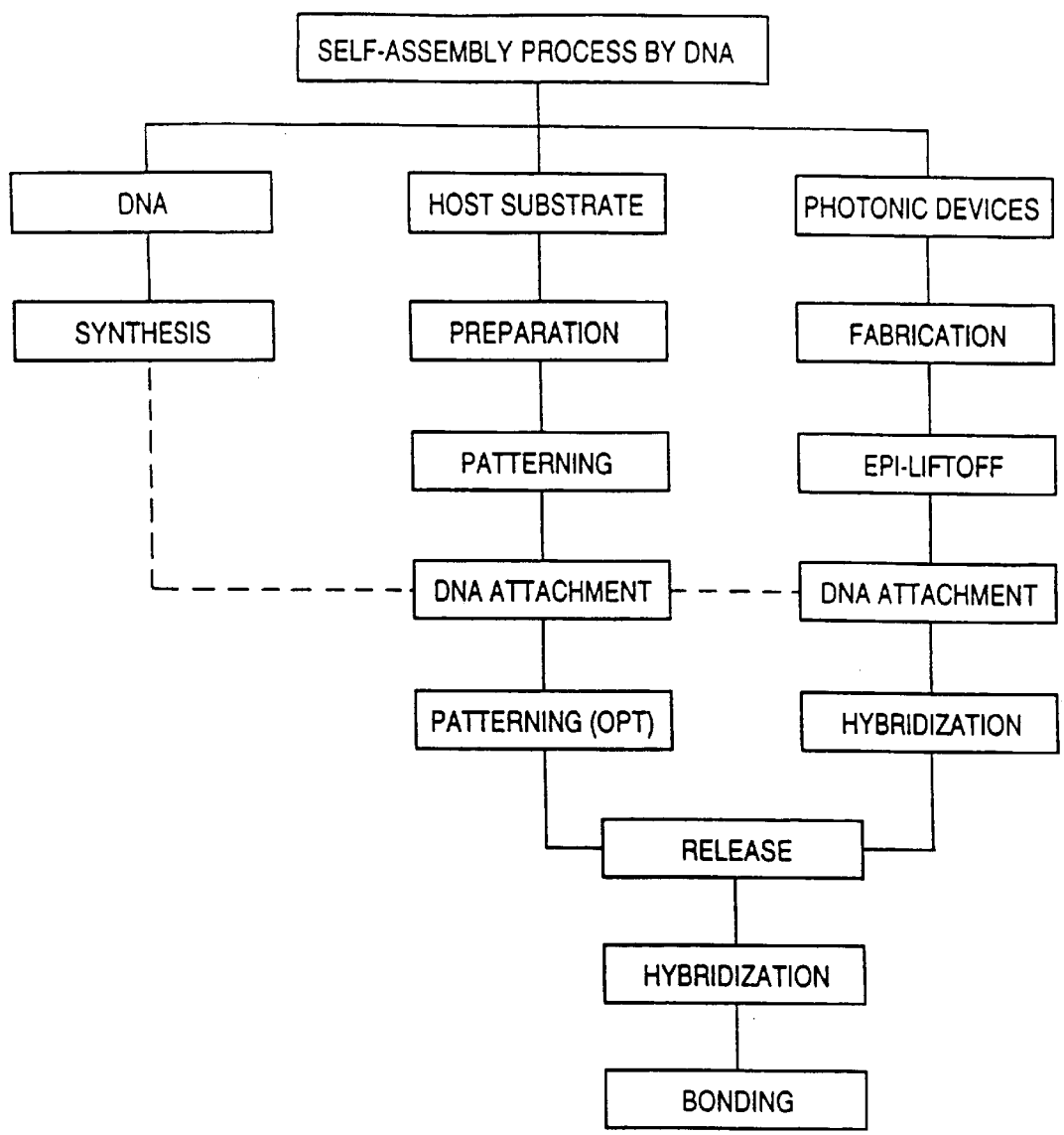
FIG. 2 is a flow diagram of self-assembly processes.

For grafting an array of photonic component devices onto a host substrates, DNA polymers with complementary sequences are first synthesized as shown in FIG. 2. The photonic component devices and desired areas of the host substrate (receptor areas) are coated with the complementary DNA sequences. The host substrate is then introduced into a hybridization solution. The devices coated with the specific DNA polymers are also released from their mother substrate into the solution. The released devices can be actively transported to their receptor areas under the influence of electrically or optically induced local fields (electrophoresis). Hybridization is carried out by carefully controlling the solution temperature, ionic strength, or the electric field strength. Once the devices are grafted via hybridization to their specific receptor areas, the solution is removed and the substrate is dried. Metallurgical (or eutectic) bonding can now be carried out at a higher temperature to fully bond the devices to the host substrate material. The clustering of sub-micron and nanoscale elements into 2-D or 3-D structures (e.g., photonic band-gap crystals), can be carried out in a similar fashion. In this case, the host substrate is replaced by other nanoscale elements. A major difference however, is the attachment technique used to position different DNA strands on the nanoscale elements.

Figure 3B:
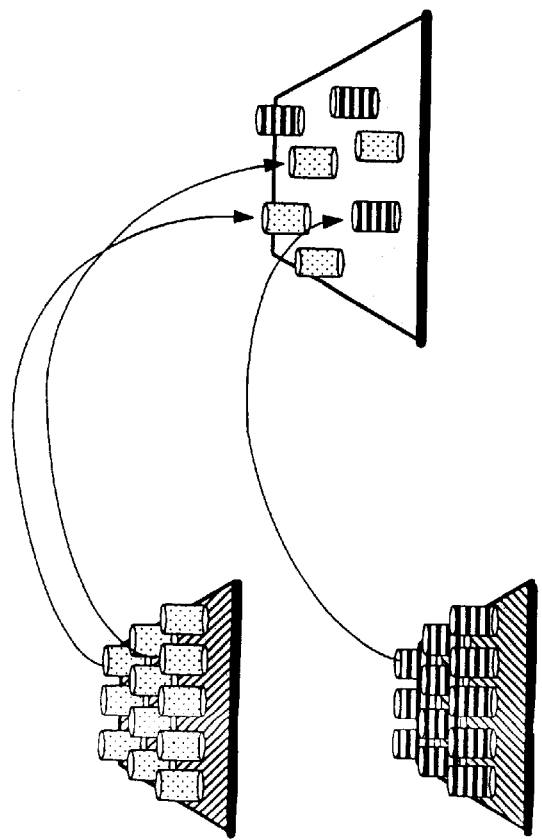
FIG. 3B is a perspective view of a clustering of nanospheres by DNA assisted self-assembly to form synthetic photonic crystals.
Figure 3A:
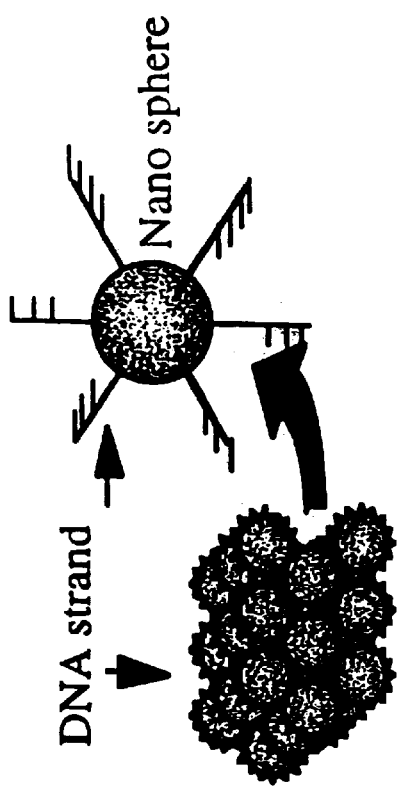
FIG. 3A is a perspective drawing of the apparatus and method for redistribution of photonic devices fabricated as dense arrays onto the host substrate without mother substrate layout constraints.

The self-assembly fabrication technique based on DNA polymers offers two unique features. First, by removing the requirement for conservation of relative device spacing (as defined by the mother substrate) during the device grafting (hybridization) process, the technique enables the micron, sub-micron or nanoscale devices to be fabricated densely on their mother substrates and then be redistributed in a pre-programmed fashion onto the host substrate (FIG. 3A).

This feature has a profound impact on the viability of intra-chip optical interconnects within large chips. It lowers the cost of silicon based smart pixels where photonic devices must be fabricated on more expensive smaller substrates. The second feature is the ability to manipulate and orient with respect to each other a large number of nanoscale devices (e.g. organic or metallic nanospheres). This feature allows the "growth" of synthetic photonic crystals with large lattice constants possessing desired orientation symmetries for exhibiting photonic bandgap properties (FIG. 3B).

Thus, the highly specific binding affinities and self-assembly of DNA polymers can lead to:

(1) Low cost smart pixels and display devices by enabling photonic or electronic micron or nanoscale devices to be self-assembled and integrated over very large areas of silicon or other substrates, i.e. the self-assembly of an arrays of light emitters on a silicon substrate, (2) Highly selective wavelength and tunable devices by enabling dielectric nanostructures to be self-assembled to form photonic bandgap crystals, i.e. the encapsulation of emitter devices within a photonic bandgap crystal layer created by the self-assembly of DNA nanospheres, (3) Ultra high density optical storage media by enabling chromophore molecules and nanostructure units to be selectively self-positioned, and (4) The selective positioning of bonding structures, such as gold, tin or solder structures as bonding pads, e.g., to achieve low cost or unassisted die-to-die processing, e.g., for flip-chip applications.

In the preferred embodiment, these applications require four steps in the process. The first involves the design and synthesis of the DNA polymer sequences and their selective attachment to the sub-micron and nanoscale devices of interest. Second, attachment of specific complementary DNA polymers to pre-selected receptor locations on a host substrate surface. Third, the self-assembly of the devices by the DNA hybridization process. The fourth process involves establishing the electrical contacts.

This invention brings together molecular biological (DNA structure and function) and photonic and electronic device principles in a synergistic manner. On the photonic device side, novel devices with very small physical dimensions take advantage of various quantum confinement techniques. In most cases, these devices must be distributed over large areas (e.g. smart pixels and displays). In other cases, these devices must be brought together densely to form regular crystal lattices (e.g. photonic bandgap crystals). With regard to processing techniques, self-assembly DNA techniques with its well developed base of DNA synthesis, modification, and hybridization is an enabling technology for these applications. DNA linkage to solid supports and various other materials is possible via a variety of processes for attaching DNA selectively to silicon, gold, aluminum and other inorganic and organic materials. A number of thin film processing techniques are highly complementary with these DNA processes. For example, as will be described later, the lift-off process can be easily adapted to produce micron, and sub-micron devices with attached DNA sequences.

KEY PROCESSES FOR DNA BASED COMPONENT DEVICE SELF-ASSEMBLY

Four techniques are important for the DNA based component device self-assembly process. These are the DNA polymer synthesis, DNA attachment chemistry, DNA selective hybridization and epitaxial lift-off of semiconductor thin films and devices. In the following sections we provide brief summaries of these techniques.

DNA Synthesis and Dervatization

The synthesis of the DNA polymer or oligomer sequences, their purification, and their Derivatization with the appropriate attachment and chromophore groups can be carried out in the following preferred manner: DNA sequences are synthesized using automated DNA synthesizer and phosphoramidite chemistry procedures and reagents, using well known procedures. DNA polymers (polynucleotide, oligonucleotides, oligomers) can have primary amine groups incorporated at chemical bonding sites for subsequent attachment or functionalization reactions. These primary amine groups can be incorporated at precise locations on the DNA structure, according to the need for that particular sequence. Attachment sequences can also contain a terminal ribonucleotide group for subsequent surface coupling reactions. Sequences, including the amino modified oligomers, can be purified by preparative gel electrophoresis (PAGE) or high pressure liquid chromatography (HPLC). Attachment sequences with terminal amino groups can be designed for covalent bonding to gold, silver, or aluminum metalized features or to small areas where silicon dioxide is present. These sequences can be further Derivatized with a thiolation reagent called succinimidyl 3-(2-pyridyldithio)propionate (SPDP). This particular reagent produces a sequence with a terminal sulfhydryl group which can be used for subsequent attachment to metal surfaces. Other attachment sequences containing a terminal ribonucleotide group can be converted to a dialdehyde derivative via Schiff's base reaction. These attachment sequences can then be coupled to aminopropylated silicon dioxide surfaces. Specific sequences designed for electronic or photonic transfer responses can be functionalized with their appropriate chromophore, fluorophore, or charge transfer groups. Many of these groups are available off-the-shelf as activated reagents that readily couple with the chemical bonding sites described above to form stable derivatives.

DNA Attachment to Solid Supports and Preparation of the Host Substrate Materials This step involves the covalent coupling of the attachment sequences to solid support materials. In the general area of DNA attachment to solid materials, sequences have been covalently attached to a number of materials which include: (i) Glass ($SiO_2$), (ii) Silicon (Si), (iii) Metals (Gold, Silver, Aluminum), and (iv) Langmuir-Blodgett (LB) films. Glass, silicon, and aluminum structures have been prepared in the following manner. Glass and silicon ($SiO_2$) are first treated with dilute sodium hydroxide solution and aluminum with dilute hydrogen fluoride solution. The materials are then Derivitized Derivatized for covalent coupling with the attachment sequences by treatment with 3-aminopropyltriethoxysilane (APS). This is carried out by refluxing the materials for 2–5 minutes in a 10% APS/toluene solution. After treatment with APS, the materials are washed once with toluene, then methanol, and finally dried for 1 hour at 100° C. Attachment to the APS Derivitized Derivatized materials is carried out by reaction with the specific dialdehyde Derivatized attachment oligomers (see FIG. 4) for 1–2 hours in 0.1 M sodium phosphate buffer (pH 7.5). In addition, attachment to metal (gold, silver, aluminum) and organic features can be carried out.

To delineate the areas where the grafting of the specialty devices will take place, a selective attachment procedure for the complementary DNA polymer may be carried out. The selective attachment can be realized by using the inherent selectivity of DNA sequences, selective attachment chemistries, or by directed electrophoretic transport. Alternatively after attachment, the DNA strands in unwanted regions can be destroyed by UV radiation. This approach is useful only when one group of devices need to be self-assembled. This approach would in normal operation preclude subsequent DNA attachment processes, and would not allow for the self-assembly of several specialty device groups. Attachment chemistry is strongly dependent upon the materials used to which the DNA polymers may be attached.

For example, to attach DNA to aluminum pads on a silicon chip coated with a protective glass layer, the aluminum regions are activated by dipping the sample for a short period of time into a dilute buffered HF solution. The end result of this process is that only a few DNA strands are attached to the protective glass layer while the exposed aluminum pads are highly reactive to DNA. This material selectivity is a convenient and general way to attach DNA to the desired regions. When material selectivity is combined with UV directed inactivation and electrophoretic transport, this allows for repeatable attachment processes to be carried out sequentially.

Consider the simultaneous self-assembly of several types of specialty devices. The receptor pads need to be grouped according to the device to which they are to be coupled. In this case, each pad group needs to be coated with a specific DNA sequence complementary to the DNA sequence attached to the specialty device that it would be bonded to. In order to "pre-program" the receptor pads, each DNA sequence is attached sequentially to the proper pads. This can be easily achieved by using the electrophoretic transport process and by applying a negative potential to the pads where DNA attachment is not desired. Simultaneously, a positive voltage can be applied to enhance attachment to the desired locations. Alternatively, an optically induced electric field can be used to migrate the DNA strands to desired locations. For a second set of DNA sequence attachment, the procedure is repeated. It should be pointed out that when only one type of device needs to be self-assembled on the host substrate, the use of the material selectivity of the DNA attachment chemistry alone is sufficient. UV radiation of the regions where DNA hybridization is not desired, would be carried out.

Component Device Preparation and Epitaxial Lift-Off

Figure 5:
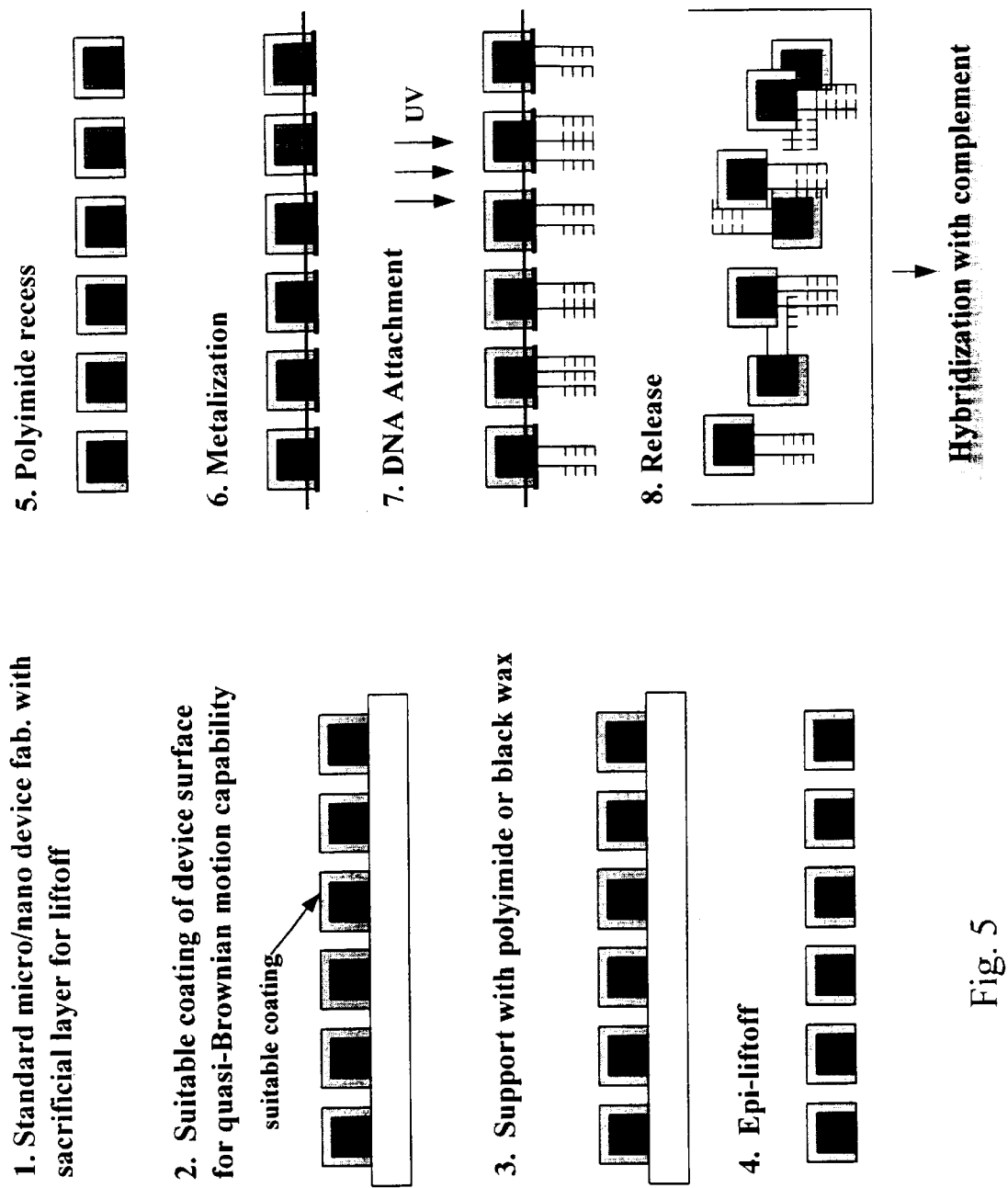
FIG. 5 shows steps for preparation of photonic devices for self assembly.

Another key step for the self-assembly process is the preparation of the sub-micron and micron-scale component devices for DNA attachment, their handling during the attachment process, and their final release into solution prior to hybridization. The epitaxial lift-off (ELO) process can substantially improve these aspects of this technique. Epitaxial films in the thickness range of 20 nm to 10 mm have been separated from their growth substrates, handled and manipulated. For example, using this technique thin III–V semiconductor films have been direct-bonded to foreign substrates, such as processed silicon wafers. Prior to lift-off, various devices can be fabricated on the films while still on their mother substrates. The first step in our self-assembly technique is the preparation of the photonic devices that are to be grafted. FIG. 5 describes a preferred process flow for this preparation step. The photonic devices are fabricated in a standard fashion on their mother substrates on a sacrificial layer as required by the ELO process. A suitable coating layer is then deposited on these devices. By controlling the characteristics of the deposited material with respect to device materials the behavior of the devices once released into the saline solution can be controlled. For example, by controlling the coating material properties the direction of the devices in the solution can be controlled. A thick polyimide film is spun to provide a physical support to the devices after the ELO process. The ELO process is carried out and the thin film devices are separated from their mother substrates. By using plasma etching, the polyimide holding membrane is recessed in areas with no devices. If needed, a metal layer can be deposited to assure good electrical contacts to the photonic devices. The DNA attachment process is then carried out and a specific DNA sequence is covalently attached on all metal surfaces. By irradiating the front surface with a UV light, the photonic devices are used as a self-aligned mask enabling exposure of polyimide areas coated with DNA polymer. In these areas, the DNA polymers react to a form that is not suitable for further hybridization. By using a solvent, the polyimide may then be removed and the devices released into the saline solution used for the further hybridization processes.

Selective DNA Hybridization Techniques

Once the host substrate is pre-programmed and the component devices are released into the solution, the self-assembly process can take place. Two different approaches for hybridization are applicable: (1) Conventional hybridization and (2) Active hybridization using an electric field.

For the conventional hybridization process, all devices may be released simultaneously into the solution. By gently agitating the devices in the solution at the proper hybridization stringency temperature and ionic strength, hybridization of the complementary DNA strands takes place as the proper device-receptor pairs come into contact. The probability of hybridization taking place may be related directly to the probability of the proper device-host pad pairs coming into contact. Since the probability distribution is most likely random, this process may take longer to achieve reasonable hybridization yields on large area surfaces unless the solution is saturated with the devices. In order to improve the selectivity and alignment accuracy several controlled heating and cooling cycles may be carried out during the hybridization process. During the heat cycle, weakly hybridized components are dissociated away to increase the chances of forming stronger bonds.

For active or electronic hybridization, the motherboard itself or another electrode array manufacturing device are used to produce localized electric fields which attract and concentrate selected component devices at selected locations. For this process the motherboard or manufacturing device has sites which can be used as an electrodes. A potential is applied across the solution between selected receptor sites and auxiliary electrodes. Receptor sites biased opposite (+) to the net charge (−) on selected devices, now affect the electrophoretic transport and concentration of these devices thereby increasing the rate of hybridization and binding. These sites can be selectively switched on or off using electronic or photonic addressing. A pulsing DC or biased AC electric field can be applied at a suitable frequency to eliminate the screening effect of the unwanted device types.

The electric field effect can also be used in a protective manner. In this case, the receptor pads are now biased the same (−) as the net charge (−) on the devices. The devices are then repelled from these regions and interact or bind only to those locations which have the opposite charge (+) or are neutral. Active electric field transport can be used to carry out multiplex and multi-step addressing of component devices and structures to any location on the motherboard array.

Another important consideration during hybridization is the alignment accuracy of the photonic devices on the motherboard or host substrate. It is assumed cylindrical photonic devices that rotation is invariant. In this case, if the device and host pad diameter is d, an alignment accuracy of d/2 may be first achieved with the natural hybridization process prior to the drying process. Devices that are misaligned with more than d/2 misalignment will not form a strong bond during the hybridization process and will not be held in place during the heating and cooling cycles of the hybridization process. Better alignment accuracy and orientation are possible when active electric field hybridization is used. Once the substrates are removed from the solution, increased surface tension during the drying process could further improve the alignment accuracy.

Metallurgical Bonding

After the hybridization process the specialty devices are held in their proper places through the formation of the double-stranded DNA structure which has a very high bonding strength. The entire assembly is then cleaned by rinsing and then dried. The DNA bond strength remains in the solid state and serves to keep the devices in place. At this point of the process, there is however, no electrical contact between the host substrate and the photonic devices. One method to achieve a metallurgical bond exhibiting an ohmic contact between the host substrate and the photonic devices is to use conductive materials on the pads and devices that can be bonded together eutectically at low temperatures. A second method is to use metals with low melting temperatures like solder or indium under a metal layer that is active for DNA attachment. While the photonic devices are held in place by the DNA bonds, the application of heat will result in the formation of a metallurgical bond. The DNA polymer will disintegrate within the bond but may only contribute to an increased contact resistance depending on the initial DNA loading factor used.

Development of Self-Assembled Emitter Arrays

As one example of the utility of these inventions, emitter arrays can be advantageously formed. Specific DNA polymer sequences may be covalently attached to semiconductor light emitting diodes (LED) and the complementary DNA sequences may be attached to receptor pads on the host silicon substrate. UV/DNA patterning techniques may be used for selective activation/inactivation of DNA on the coated surfaces. All DNA Derivitized Derivatized test structures and materials will then be tested for selective hybridizability using complementary fluorescent DNA probes. LED test devices Derivatized with specific DNA sequences may be hybridized to test substrates Derivatized with complementary DNA sequences.

Development of Self-Assembled Photonic Band-Gap Structures

Photonic or crystals may be formed using the DNA self-assembly technique. Photonic Bandgap Structures are artificial periodic lattice structures in two- or three-dimensional arrangements and composed of elements of proper dimensions, density and separations. Such structures result in the modification of photonic density of states and a gap in the electromagnetic wave dispersion. Indeed, photonic bandgap structures operating at specific optical wavelengths have been demonstrated. Potential applications of photonic bandgap materials include tailoring of the spontaneous emission of a laser to achieve ultra-low threshold lazing, improved wave guiding structures without radiation loss, novel optical modulators, etc.

In one aspect of these inventions, nano-scale rods or spheres of higher dielectric constant are positioned in a medium of lower dielectric constant. A three-dimensional diamond lattice arrangement of close-packed tetrahedrally-connected dielectric spheres (200 nm in diameter and a refractive index of 3.6) embedded in a lower-dielectric-constant medium such as air exhibits photonic bandgaps. This invention relates to new ways of constructing photonic crystals by self-assembling high dielectric constant elements with desired geometry's in lower dielectric materials. In order to construct such a structure and to obtain the desired lattice geometry and nano-elements at the lattice sites, the selective attachment of DNA sequences to the nano-elements and the hybridization of finite sequences of DNA strands are employed. Metal spheres exhibiting magnetic properties may have attached DNA strands. Magnetic properties may be used to control the orientation of the spheres (or rods for 2-D crystals). The metal spheres may be dipped into a DNA solution, aligned using a magnetic field, and exposed under UV radiation. This technique allows 2D and 3D photonic-bandgap structures to be "grown" around active optoelectronic devices with minimum fabrication complexity. Additionally, because the DNA bonds connecting the nanospheres are somewhat flexible, this technique may also provide a means of realizing tunable photonic bandgap structures. The process for electronic orientation is discussed in the "Process for Electric Field Orientation Synthesis of Nanospheres and Sub-Micron Devices", below.

The various DNA polymer (oligonucleotide) sequences described above, in the 20-mer to 50-mer size range, may be synthesized on automated DNA synthesizers using phosphoramidite chemistry. Longer DNA sequences are generally required to bind larger objects to surfaces because the binding force must be sufficient to overcome forces (e.g., shearing forces) tending to remove the object. Longer DNA sequences (>50 mers) may be constructed using the polymerize chain reaction (PCR) technique. The DNA sequences may be further Derivatized with appropriate functional groups (amines, thiols, aldehydes, fluorophores, etc.). All sequences may be purified by either PAGE gel electrophoresis or HPLC. After purification, all sequences may be checked on analytical PAGE gels for purity, and then tested for specificity by hybridization analysis.

Several DNA sequences may be used to develop and test additional chemistries for the covalently attachment to various, organic polymer based nanospheres, semiconductor, and other material substrates (glass, gold, indium tin oxide, etc.). Additional attachment chemistries provide more options and flexibility for attachment selectivity to different semi-conductor materials.

Specific DNA polymer sequences may be covalently attached to semi-conductor test structures and the complementary DNA sequences to test substrate (motherboard) materials. UV/DNA patterning techniques may be used for selective activation/inactivation of DNA on the coated surfaces. All DNA Derivatized test structures and materials will then be tested for selective hybridizability using complementary fluorescent DNA probes.

Nanospheres, nanoparticles, and semi-conductor test structures Derivatized with specific DNA sequences will now be hybridized using both conventional (temperature, salt, and chaotropic agents) and electronic (electrophoretic) techniques to the test substrates (motherboards) Derivatized with complementary DNA sequences. The hybridization techniques may be optimized for highest selectivity and least amount of non-specific binding.

Fabrication of an LED Array

Specific DNA polymer sequences may be covalently attached to semi-conductor light emitting diode (LED) component devices and the complementary DNA sequences to motherboard materials. UV/DNA patterning techniques may be used for selective activation/inactivation of DNA on the coated surfaces. LED component devices Derivatized with specific DNA sequences are then hybridized to test substrates (motherboards) Derivatized with complementary DNA sequences.

Self-Assembly Fabrication of a Photonic Crystal Structure

Multiple specific DNA polymer identities may be incorporated into nanoparticles or nanospheres for the self-assembly around emitter test devices located on motherboard materials. UV/DNA patterning techniques may be used for selective activation/inactivation of DNA on the coated surfaces. Nanoparticles Derivatized with specific DNA sequences will now hybridized to the emitter test devices located on the substrates (motherboards) Derivatized with complementary DNA polymers.

Further Aspects of Self-Assembly

Figure 30:
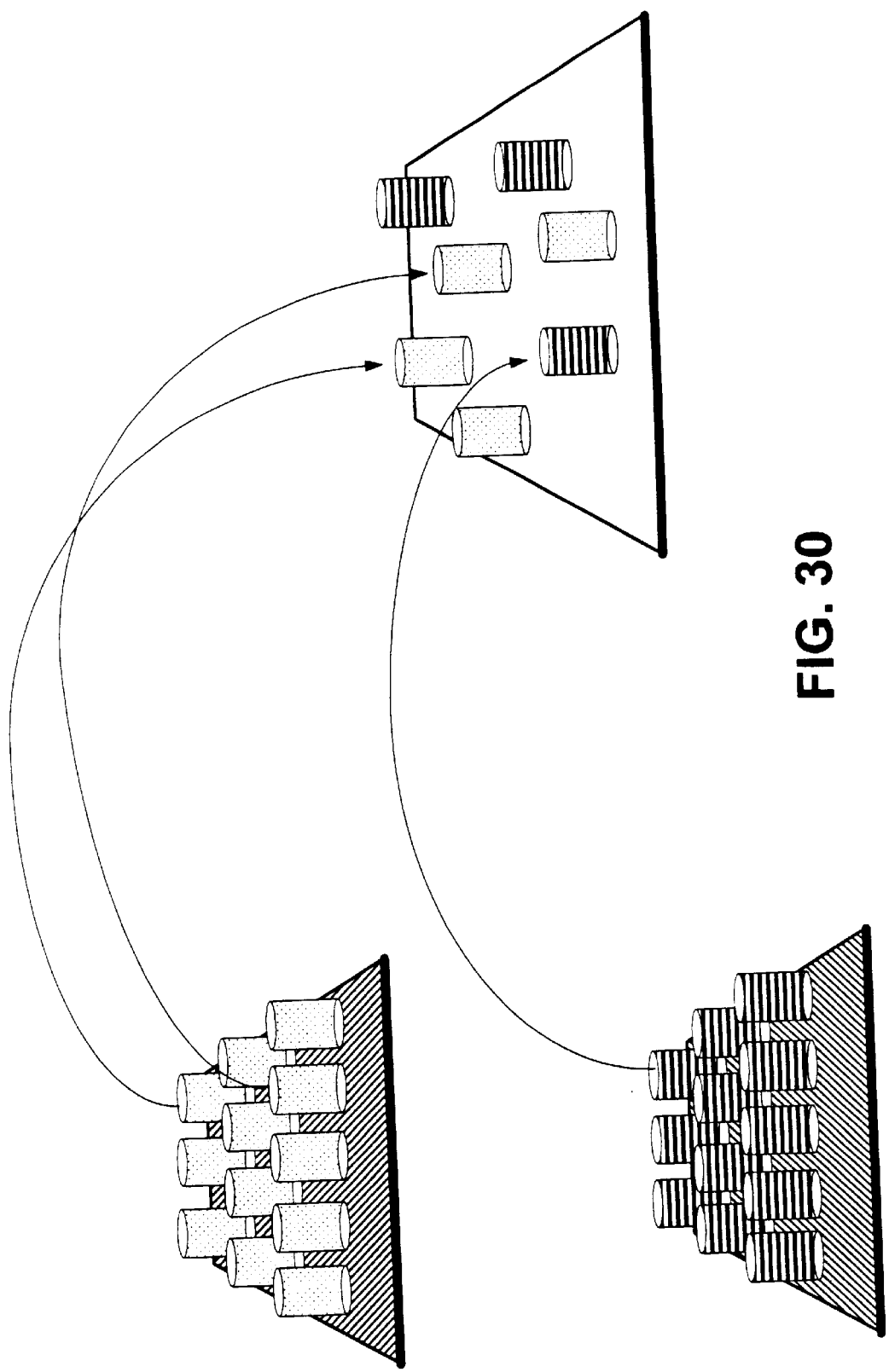
FIG. 30 shows a perspective view of global distribution of small dense structures from small dense chips on to less dense mother boards.
Figure 31:
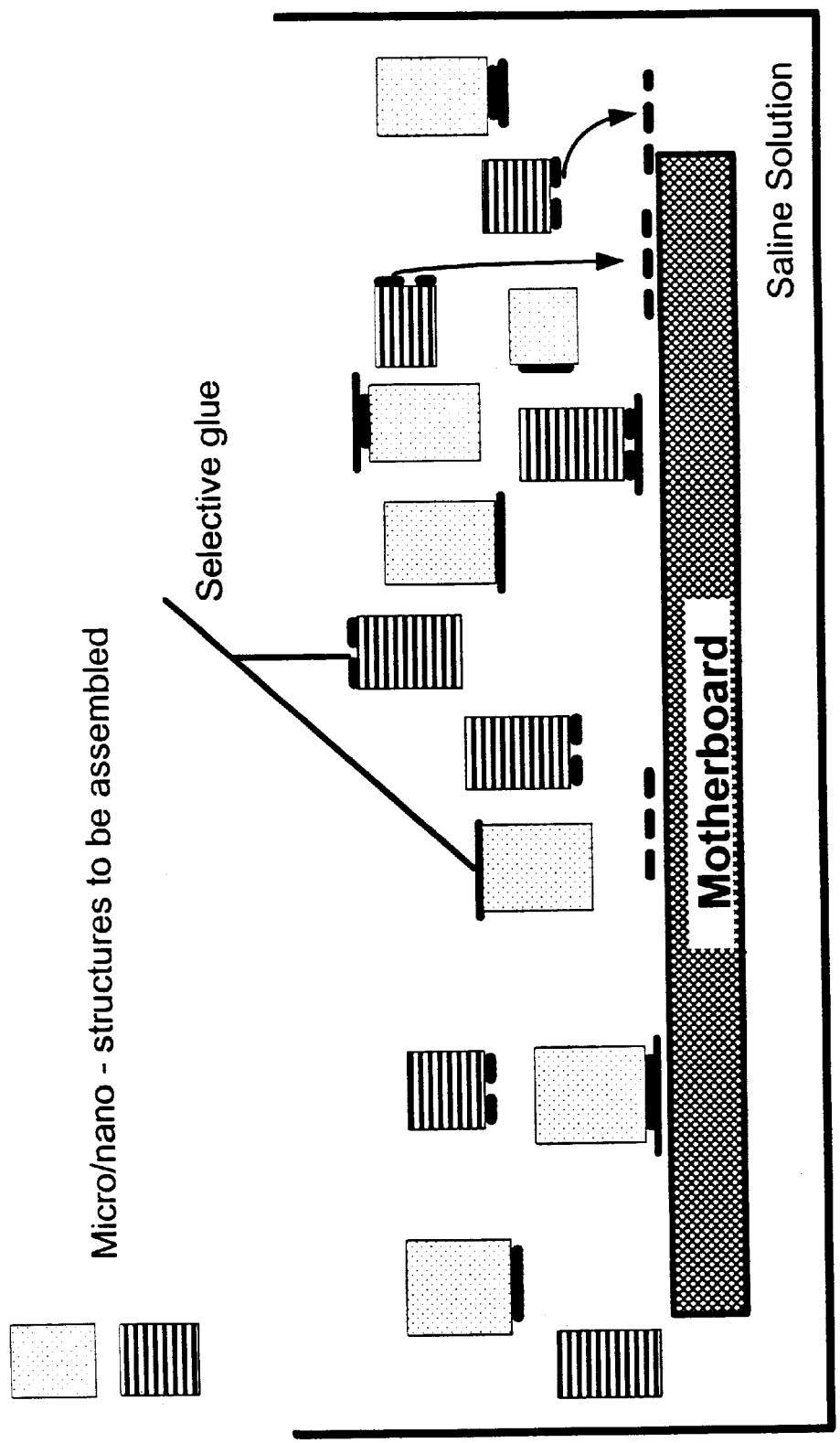
FIG. 31 shows a cross-sectional view of a structure for the self-assembly of micro or nanostructures utilizing a selective glue in which specialty devices of the given type are provided with a specific DNA polymer glue, the areas where these devices must attach being covered with the complimentary DNA glue.

This invention provides for assembling specialty devices in parallel and over larger areas (up to several meters on a side) using a "self-assembly" technique. In this approach, each device to be grafted somehow "knows" where it is destined to be on the motherboard. This invention relates to a new integration technique based on programmable self-assembly principles encountered in biological systems. This new technique removes the requirement of dimension conservation during the grafting process. Our objective is to demonstrate the self-assembly of micro/nano structures on silicon using DNA (Deoxyribonucleic Acid) polymers as "selective glues", thereby developing techniques for integrating these structures sparsely onto large area motherboards. This brings together with high precision, at low cost, devices made of different materials with different real densities as shown in FIG. 30. This approach relies on the principles of programmable self-assembly found in all biological systems, and uses existing well-understood synthetic DNA chemistry as the enabling process. These techniques include: 1) remove the specialty devices from their mother substrates using the epitaxial lift-off process, 2) attach selective DNA polymer sequences onto the specialty devices using DNA attachment chemistry specially developed in our company, 3) selectively attach complementary DNA polymer sequences to proper locations on the motherboard substrate, and 4) carry out self-assembly by using hybridization of the complementary DNA strands. This uses DNA polymer sequences as a smart and very selective glue to attach micron/nanosize specialty devices to designated areas on a motherboard (see FIG. 31).

Selective DNA Hybridization and Electric Field Transport Techniques

Figure 7:
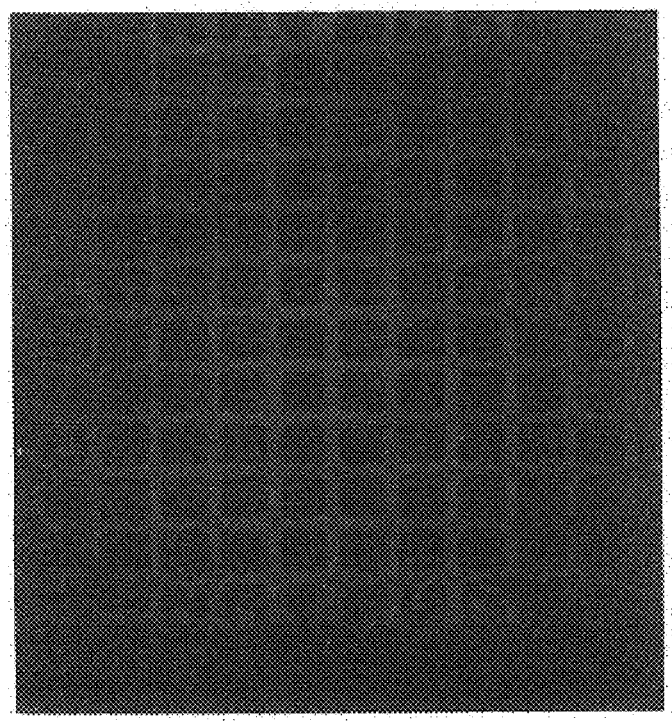
FIG. 7 is a plan view of a UV write/imaging into monolayers of DNA on silicon/silicon dioxide/aluminum.
Figure 32:
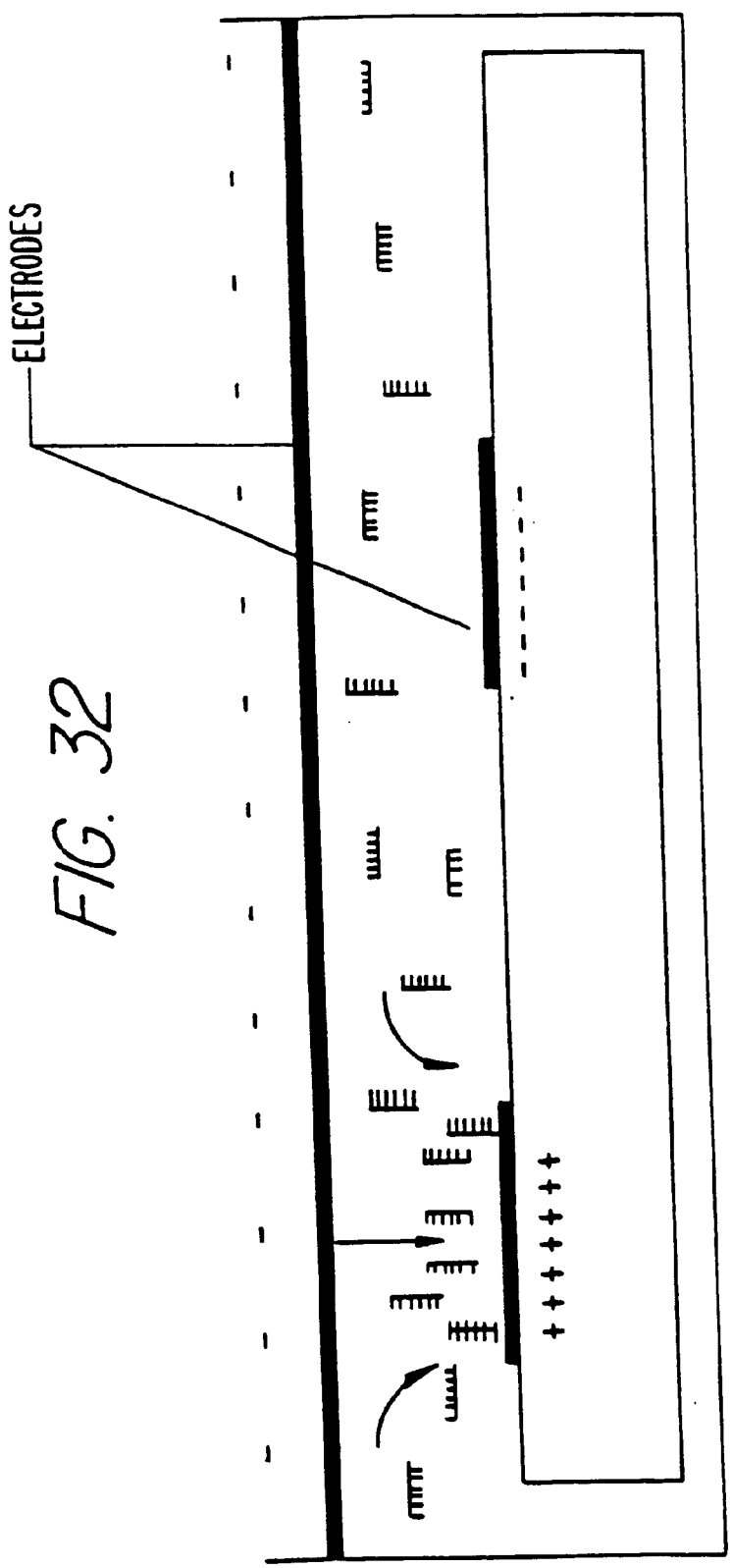
FIG. 32 shows a cross-sectional view of selective electric field deposition of DNA onto the specially derivitized microelectrode surfaces.

Techniques for the hybridization of DNA sequences to complementary DNA sequences attached to solid support materials are well known and used in many biotechnological, molecular biology, and clinical diagnostic applications. In general hybridization reaction are carried out in aqueous solutions which contain appropriate buffer electrolyte salts (e.g., sodium chloride, sodium phosphate). Temperature is an important parameter for controlling the stringency (specificity) and the rate of the hybridization reactions. Techniques exist for hybridization of DNA sequences to semiconductor materials. The first is a UV lithographic method which allow imprinting or patterning of DNA hybridization onto solid supports materials such as silicon dioxide and various metals. The second is a method for electrophoretically transporting DNA-nanostructures (nanostructures to which specific DNA sequences are attached) to selected locations on substrate materials. The technique for UV lithography with DNA involves first coating a substrate material with a molecular layer of specific attachment DNA polymer sequences. An appropriate mask can be used to imprint a pattern into the attachment layer of DNA by exposure to UV irradiation (300 nm) for several seconds. The DNA in the area on the substrate exposed to UV light becomes in-active to hybridization with its complementary DNA sequence i.e., it is not able to form the double-stranded structure. FIG. 7 show fluorescent DNA on a silicon structure was patterned with 10 micron lines using an electron microscope grid pattern. After UV patterning the material is hybridized with a complementary fluorescent labeled DNA probe, and examined epifluorescent microscopy. The fluorescent image analysis shows where the complementary probe has hybridized (fluorescent), and where no hybridization has occurred (no fluorescence). In addition to DNA based UV photolithographic type processes, other electric field based process allows derivatized DNA and charged fluorescent nanospheres to be electrophoretically transported and deposited onto selective microscopic locations on solid supports. The basic method and apparatus for this technology is shown in FIG. 32. Negatively charged DNA, sub-micron or micron-scale structures can be suspended in aqueous solutions and transported via an electric field (electrophoresis in solutions) to microscopic locations which are biased positive, relative to other locations which are biased negative. This is a particularly important technique in that it provides a mechanism to direct the transport of specifically labeled devices to specific locations on a substrate material.

Micron/Nanoscale Structure Preparation

The first step in our self-assembly technique is the preparation of the specialty devices to grafting. In this case, the specialty devices are fabricated in a standard fashion on their mother substrates on a sacrificial layer as required by the ELO process. A suitable coating layer is then deposited on these devices to assure they have a Brownian like motion in the saline solution. By controlling the characteristics of the deposited material with respect to device materials the behavior of the devices once released into the saline solution can be controlled. For example, by controlling the coating material properties we could control the direction of the devices in the solution. Once the devices are coated, a thick polyimide film may be spun to provide a physical support to the devices after the ELO process. The ELO process may be carried out and the thin film devices may be separated from their mother substrates. By using plasma etching the polyimide film may be recessed to provide sufficient steps to prevent the metal layer from being continuous. The DNA attachment process is then carried out and a specific DNA sequence may be covalently attach on all the metal surfaces. By irritating with a UV light from the front surface of the devices, the DNA areas that are exposed and not protected, may be destroyed or put in a form that is not suitable for further hybridization. By using a proper solvent the polyimide will then be removed and the devices may be released into the saline solution used for the further hybridization processes.

Preparation of the Motherboard Substrate

To delineate the areas where the grafting of the specialty devices will take place, a selective attachment procedure for the complementary DNA polymer must be carried out. The selective attachment can be realized by using the inherent selectivity of DNA sequences, selective attachment chemistries, or by directed electrophoretic transport. Alternatively after attachment, the DNA strands in unwanted regions can be destroyed by UV radiation. This approach is useful only when one group of devices need to be self-assembled.

As described in earlier sections, DNA attachment chemistry is strongly dependent on the materials used to which the DNA polymers may be attached. For example, to attach DNA to aluminum pads on a silicon chip coated with a protective glass layer, we first activate the aluminum regions by dipping the sample for a short period of time into a dilute buffered HF solution. The end result of this process is that only a few DNA strands are attached to the protective glass layer while the exposed aluminum pads are highly reactive to DNA. This material selectivity is a convenient and general way to attach DNA to the desired regions. When material selectivity is combined with UV directed inactivation and electrophoretic transport process, this allows for repeatable attachment processes to be carried out sequentially. Consider the simultaneous self-assembly of several types of specialty devices. The pads need then to be grouped according to the device to which they are to be coupled. In this case, each pad group needs to be coated with a specific DNA sequence complementary to the DNA sequence attached to the specialty device that it would be bonded to. In order to "pre-program" the motherboard pads, each DNA sequence can be attached sequentially to the proper pads. This can be easily achieved by using the electrophoresis process and by applying a negative potential to the pads where DNA attachment is not desired. Simultaneously, a positive voltage can be applied to enhance attachment to the desired locations. For a second set of DNA sequence attachment, the procedure may be repeated with a different set of programming voltages. Thus, when the self-assembly of multiple device types need to be carried out simultaneously, the motherboard receiving pads may be programmed by applying a proper set of positive and negative potentials to the pads. When only one type of device needs to be self-assembled on the motherboard, the use of the material selectivity of the DNA attachment chemistry alone is sufficient.

Specific DNA Polymers: A Selective Glue

Figure 33:
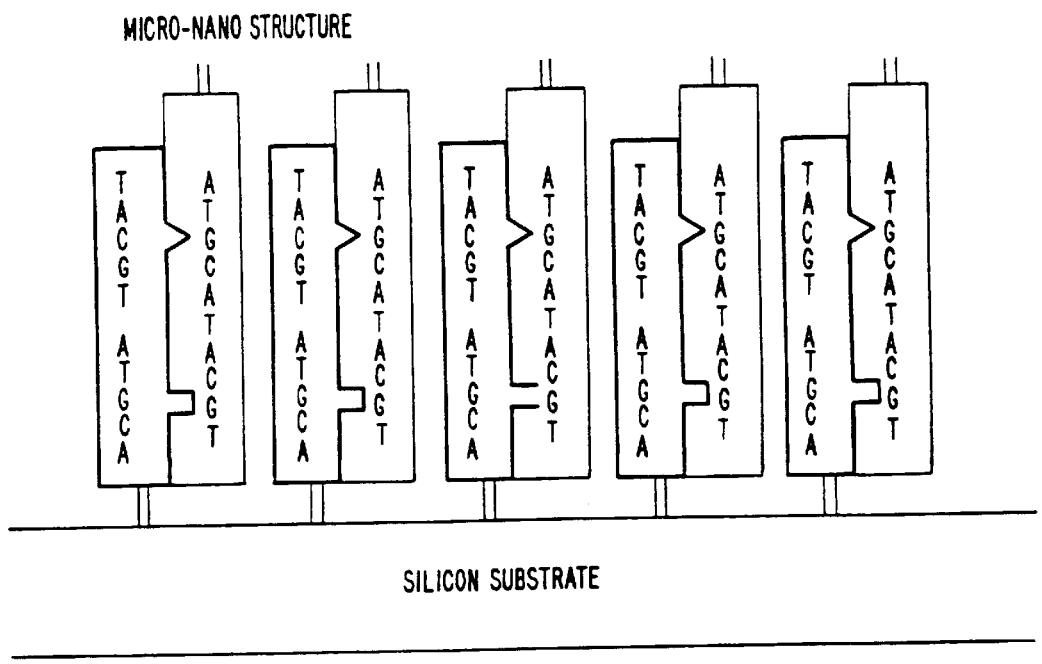
FIG. 33 shows a cross-sectional view of a micro or nanoscale structure coupled to its host mother board substrate by selective DNA hybridization between complimentary DNA strands (SEQ ID NOS: 11 and 12).

Once the motherboard is pre-programmed and the specialty devices are released and are freely moving in the saline solution bath, the self-assembly process can take place. At the proper (hybridization) stringency temperature, and by agitating gently the devices in the solution, hybridization of complementary DNA strands may be allowed to take place as the proper device-pad pairs come into contact (see FIG. 33). To achieve this process several different methods may be investigated.

Conventional and Electronic Hybridization

In this methods all devices may be released simultaneously into the solution, and the probability of a hybridization process taking place may be related directly to the probability of the proper device-pad pairs to come into contact. Under very simplifying assumptions, the probability of a hybridization $P_h$ may be roughly related to the ratio of the total available pad area $A_p$ to the mother board area $A_{mb}$ $$P_h N A_p / A_{mb}$$

where N is the real density of one of the specialty device groups in the solution. Since the probability distribution is expected to be random, this process may take very long times to achieve reasonable hybridization yields. Alternatively it may require the solution to be saturated with the specialty devices. This may increase the cost of the process and limit the number of types of specialty devices that can be self-assembled. In order to improve the selectivity and alignment accuracy several heating and cooling cycles will be carried out during the hybridization process. During the heat cycle, weakly hybridized components may be dissociated away to increase the chance of forming stronger bonds.

Epitaxial Lift-Off Process

A key part of the self-assembly process is the preparation of the micro/nano scale devices for DNA attachment, their handling during the attachment and finally their release into the saline solution prior to hybridization. The most popular ELO approach is to employ the selectivity of dilute HF acid on the Al GaAs series of alloys. The Aluminum rich alloys etch at a rate of approximately 1 mm/hr, while the etch rate of Gallium rich alloys is almost undetectable, less than 0.1 nm/hr. An intermediate layer of AlAs dissolves, allowing upper epitaxial layers to simply float away from the substrate. Other separation methods have also been used, including mechanical cleavage (CLEFT), and total substrate etching down to an etch stop layer. Epitaxial films in the thickness range between 20 nm and 10 mm have been separated from their growth substrates, handled and manipulated.

For example, using this technique thin III–V semiconductor films have been direct-bonded to foreign substrates, such as processed silicon wafers. The mechanical flexibility of ELO films allows a perfect conformation of the films to the substrate topography, which creates a strong and complete bond. The ELO technique then, produces a monolithic-like epitaxial thin film on an engineered substrate. Prior to lift-off, various devices can be fabricated on the films while still on their mother substrates. The ELO technique stands somewhere intermediate between a hybrid approach, such as flip-chip solder bump mounting, and a fully monolithic approach, such as direct hetero-epitaxy; it combines, however, the advantages of both. ELO is a true thin-film technology, allowing thin-film metal wiring which passes back and forth over the edge of a thin III–V film and onto a silicon micro-chip substrate. At the same time, the thin film is grown lattice-matched and essentially homo-epitaxially. Material quality, of the utmost importance for minority carrier devices such as light emitters, is never compromised. Advantages of the ELO technology over hybrid flip-chip technology include low packaging capacitance and high packing density. For high speed micro-circuits, wiring capacitance must be very low. The penalty is not merely the burden of added power dissipation. Since the series resistance of metal interconnects is not negligible, the RC time constant will ultimately act to limit the speed of optoelectronic micro-circuits irrespective of power dissipation problems, severe as they might be. The ultimate achievable packing density is somewhat scaled with respect to the working dimension of technologies. Therefore, the ELO may offer more in this aspect than the solder bump technique.

ELO films grafting on processed silicon micro-circuits requires consideration of the ultra-fine scale roughness of the deposited oxide surfaces of the micro-chip. Surface roughness interferes with the quality of the Van der Waals or metallurgical bond.

Sequential Hybridization Under DC Electric Field

To increase the probability of hybridization, a second method is to introduce each device group separately and to confine the specialty devices within regions near the positively biased pads. This confinement can be done under the influence of a DC electric field by applying a suitable positive voltage to the pads. The effect of the electric field can then be viewed as increasing the ratio of the areas, or equivalently increasing the device density, N, in the above equation. However, in this case each device group must be introduced sequentially, so the unwanted device groups do not screen the right devices from reaching the pad.

Hybridization Under an AC Electric Field

The disadvantage of the sequential hybridization is that it increases the cost of manufacturing as the types of specialty devices is increased. An alternative method is to introduce all device types concurrently into the solution, to apply an initial DC voltage to create a distribution of the devices around each pad, and then to apply an AC voltage at a suitable frequency to eliminate the screening effect of the unwanted devices types. The effect of the AC field can be seen as a stronger stirring mechanism.

Metallurgical bonds

Figure 34:
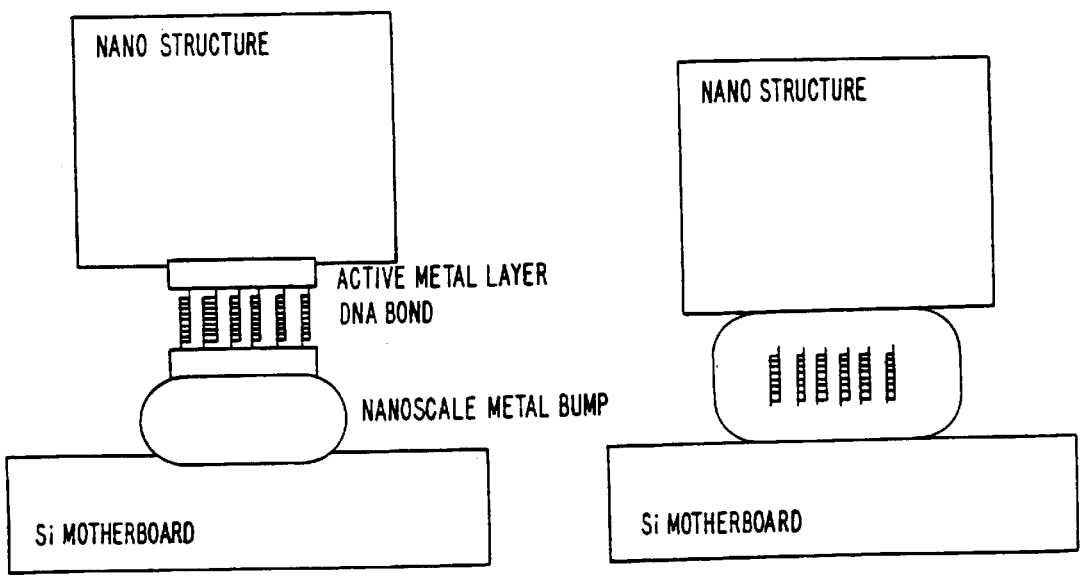
FIG. 34 shows a cross-sectional view of nanostructures held in place via a DNA bond (left-hand side) and nanostructure held by a metallurgical contact after a high temperature cycle (right-hand side).

After the hybridization process the specialty devices are held in their proper places through the formation of the double-stranded DNA structure which has very high bonding strength. The entire assembly is then cleaned by rinsing and then dried. At this point there is no electrical contact between the motherboard and the specialty devices. The DNA bond strength remains in the solid state and serves to keep the devices in place. One method to achieve a metallurgical bond with ohmic contact is to use conductive materials on the pads and devices that can be bonded together eutectically at low temperatures. A second method is to use metals with low melting temperatures like solder or indium under a metal layer that is active for DNA attachment. In this case the bumps must be made in nanometer dimensions. While the device are held in place by the DNA bonds, in both cases the application of heat will result in the formation of a metallurgical bond and an ohmic contact. The DNA polymer will remain within the bond but may only contribute to an increased contact resistance depending on the initial DNA loading factor used. FIG. 34 shows a the process described above.

Alignment and Orientation of the Specialty Devices

One of the critical issues that needs to be addressed in the self-assembly approach is the accuracy with which the specialty devices can be aligned to the pads on the motherboard. We will first assume that the specialty devices have a circular base such that the process is rotation invariant. In this case, it is expected that if the pad diameter is d, an alignment accuracy of d/2 could be achieved with the DNA bonding process. Devices that are misaligned with more than d/2 misalignment will not form a strong bond during the hybridization process and would not be held in place during the heating and cooling cycles of the hybridization process. In addition, if the nano-bump technology outlined in the previous section is employed, after the high temperature cycle for forming the metallurgical bonds, the devices may be self-aligned to the pads in a similar fashion as with the C4 technology used for flip-chip bonding.

Figure 35:
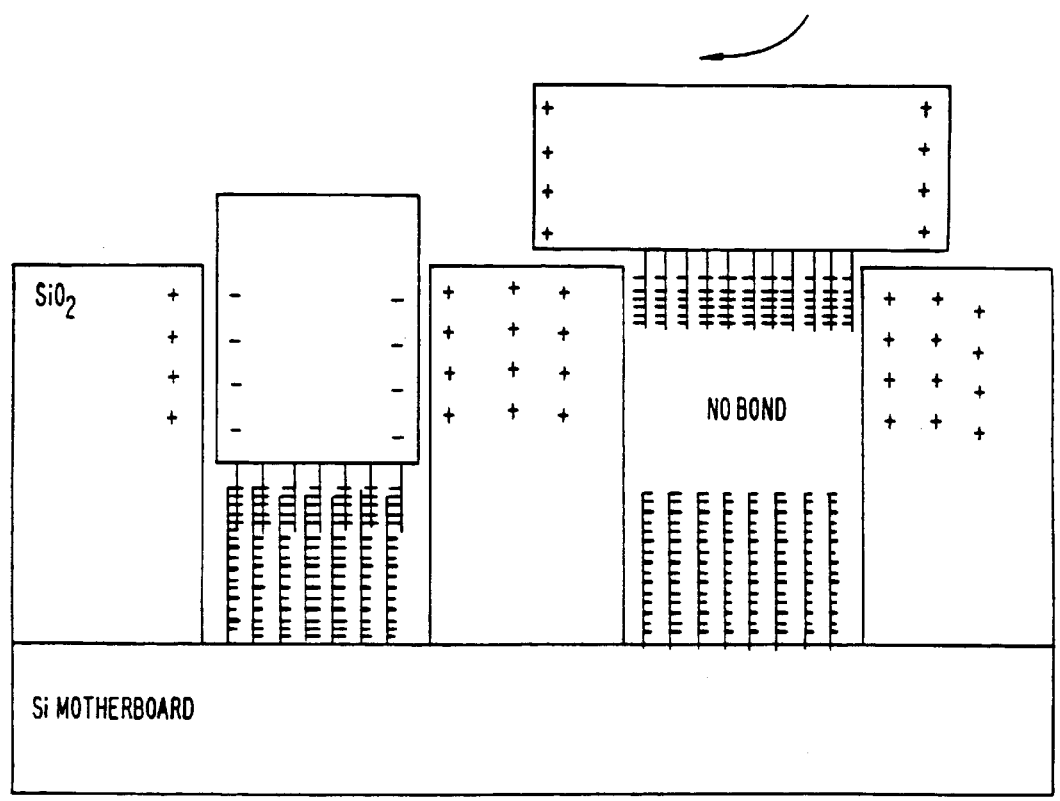
FIG. 35 shows a cross-sectional view of an apparatus for the orientation of specialty devices prior to hybridization by physical masking and charge guiding.

A more difficult issue arises if the specialty device do not have a circular symmetric base and need to be placed with a certain orientation on the pads. Two different approaches for bonding with the proper orientation may be used. As a first approach, properly patterned silicon dioxide layers are used to physically mask out specialty devices with the wrong orientations as shown in FIG. 35. The devices will fit onto the pads only if they possess the right orientation. Another approach to orient the device is to use coulombic forces prior to the hybridization of DNA. By ion implantation, or e-beam lithography exposure an opposite sign charge build-up can be realized in certain locations on the pads and on the devices. These charge patterns guide the devices to their proper orientations. As can be seen in FIG. 35, both approaches can be used together to provide DNA bonding with proper orientation of the specialty devices.

Process For Electric Field Orientation Synthesis of Nanospheres and Sub-micron Devices Electric field synthesis is preferably used for producing nanostructures or microstructures (e.g., nanospheres, nanoparticles, sub-micron and micro scale devices) with multiple DNA surface identities. These multiple surface identities can be in the form of specific DNA sequences which are located at different co-ordinates on the particle surface. These co-ordinates can be, for example, polar or tetrahedralin nature, and impart potential self-assembly properties which allow the nanostructures to form 2 and 3 dimensional photonic and electronic structures (such as the photonic band gap structures). FIG. 36 (upper) shows a generalized diagram of a the nanosphere (20 nm diameter) with multiple DNA sequence identities in polar and equatorial positions. FIG. 36 (lower) also shows some simple structures that could be formed by hybridizing the nanospheres together.

Figure 37:
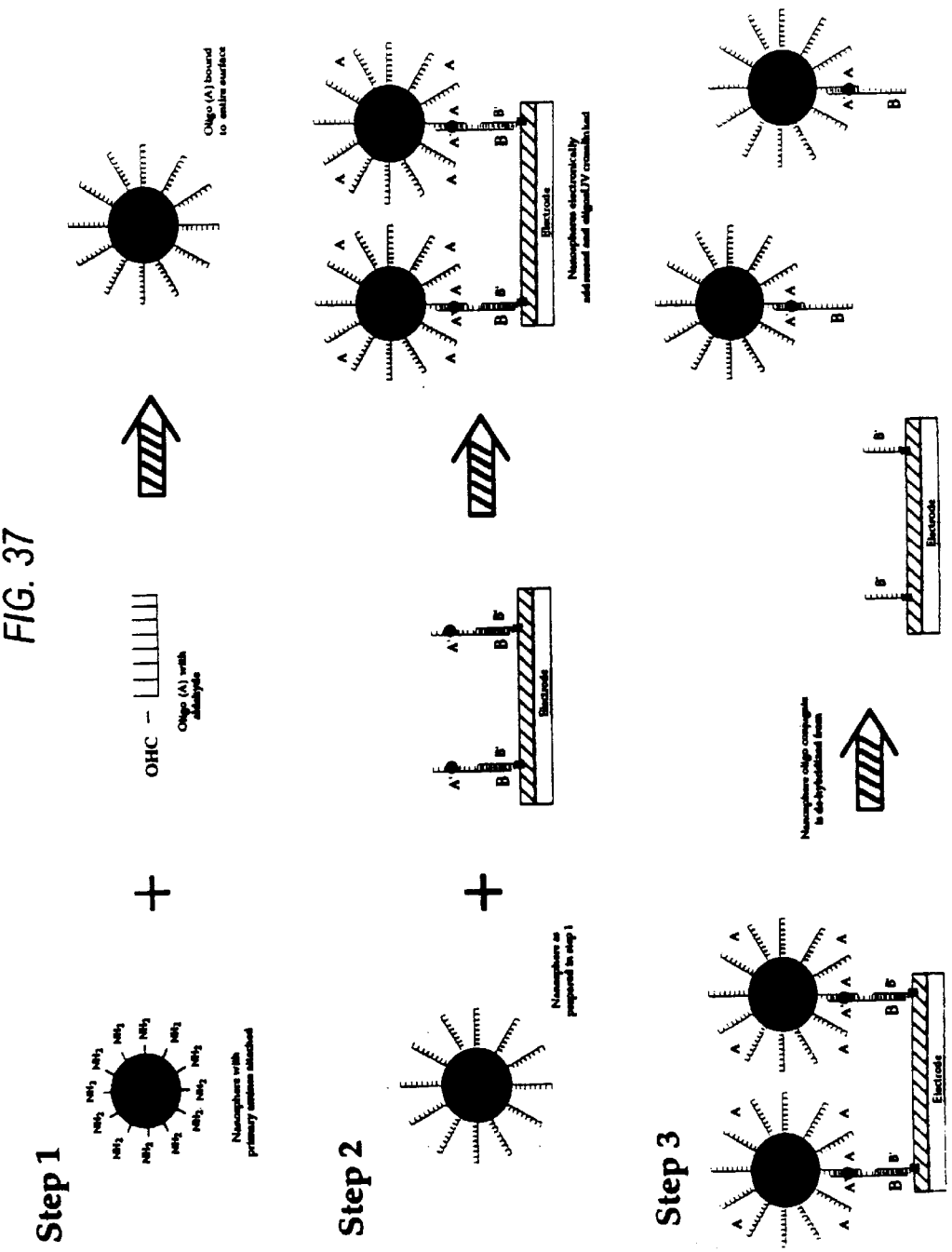
FIG. 37 shows the steps in a process for electric field orientation of devices.
Figure 38:
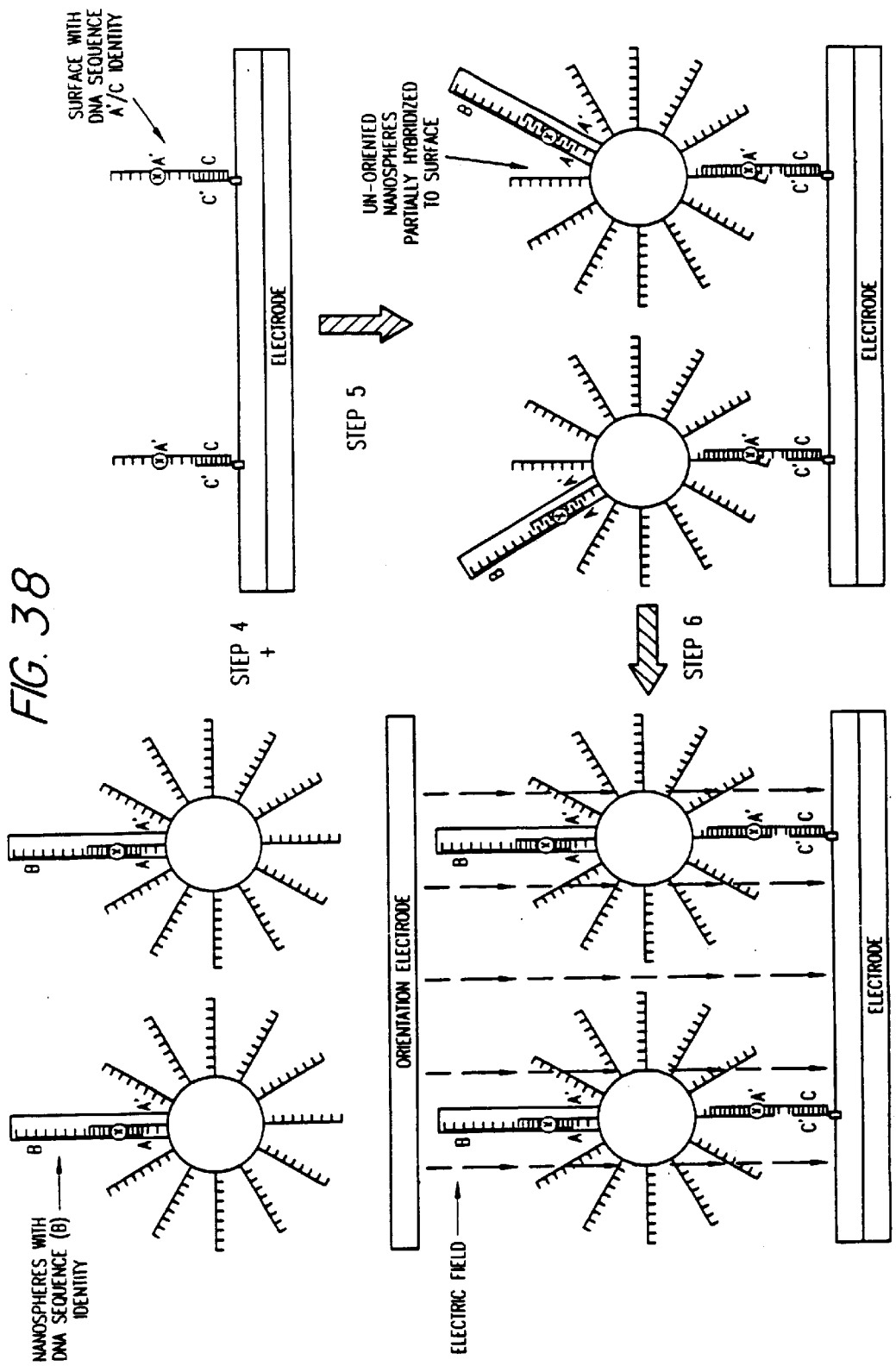
FIG. 38 shows further steps in the electric field orientation process.

FIG. 37 shows the initial steps for producing such nanostructures. In step (1), a suitably functionalized nanosphere (with amine groups) is reacted with aldehyde modified oligonucleotides with sequence identity (A). Identity (A) refers to a unique sequence of bases in the DNA; for example a 20-mer oligonucleotide with a 5'-GCACCGATTCGAT ACCGTAG-3' sequence (SEQ ID NO: 1). In step 2, the oligo (A) modified nanospheres are now hybridized to a microlocation surface (with an underlying electrode) which has a complementary A' sequence (5'-CTACGGTATCGAATCGGTGC-3') (SEQ ID NO: 2). The (A') sequence contains a crosslinker agent (psoralen) and extends into a secondary sequence with (B) identity (5'-TTCAGGCAATTGATCGTACA-3') (SEQ ID NO: 3), which was in turn hybridized to a (B') DNA sequence (5'-TGTACGATCAATTGC CTGAA-3')(SEQ ID NO: 4) covalently linked to the surface. In step 3 the hybridized nanospheres are now given a short exposure to UV irradiation which causes the psoralen moiety within the (A/A') hybridized sequence to covalently crosslink. The nanospheres are now de-hybridized (passively or electronically) from the surface. The nanospheres now have a (B) DNA sequence identity imparted to a polar position on the structures. FIG. 38 shows the continuation of the processing scheme. In steps 4 and 5, the (B) DNA sequence identity modified nanospheres are now "partially hybridized" to a new microlocation which in turn has been hybridized with a (C-A') sequence, to a complementary C' sequence which is covalently linked to the surface. The (C) sequence is different form the (A) and the (B) DNA sequences. The (B) DNA sequence nanobeads partially hybridize to the surface via the (A/A') DNA sequences, however they are not oriented in any particular fashion on the surface. Because the (B) DNA nanospheres have a non-uniform negative charge distribution on their surface (due to the extra charge from the (B) DNA, they can be oriented in an electric field. In step 6, a secondary electrode is positioned above the lower electrode, and an electric field strength is applied which is strong enough to orient the nanospheres, but does not de-hybridize them from the surface. While FIG. 38 shows the nanospheres in a polar orientation, in terms of the (B) and (C) sequences; the relative positioning of the electrodes can produce electric fields which yield other angles for the relative position of the (B) and (C) DNA sequences. When the nanospheres are in their correct alignment, they can be completely hybridized (A'-C/C'), by lowering the temperature, and then exposed to UV irradiation to crosslink the (A/A') sequences. Upon de-hybridization, this produces a nanosphere with (B) and (C) DNA sequences with relative polar (north and south) positions. We believe that repeating the process two more times can produce nanospheres with (B), (C), (D), and (E) DNA identities in polar/equatorial or tetrahedral coordinates.

Multi-Step and Multiplex Synthesis and Fabrication Techniques and Devices

Figure 39:
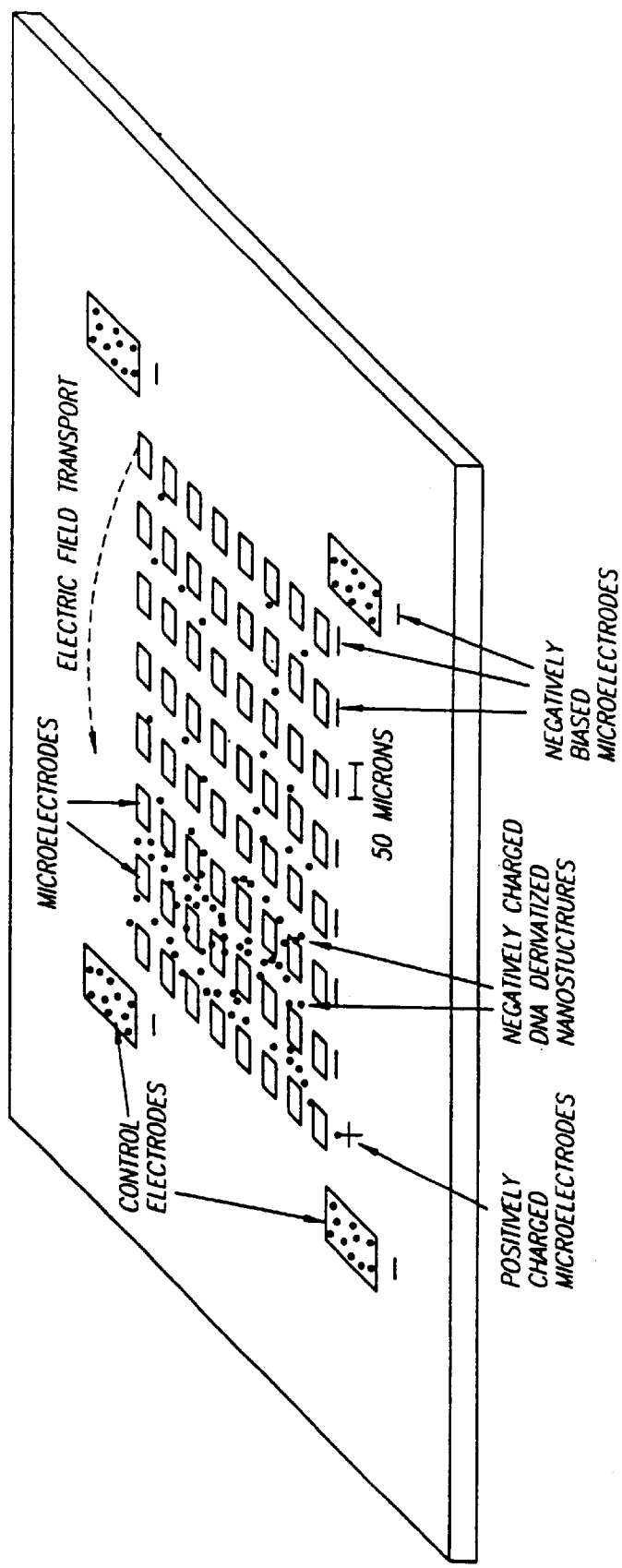
FIG. 39 shows a perspective view of nanostructure transport and assembly on a microelectronic array device.

Various techniques and devices can be used to carry out multi-step and multiplex synthesis and fabrication. FIG. 39 shows a microelectronic array device with 64 microelectrodes arranged in an 8×8 matrix, and four larger control electrodes just outside the matrix. Electrode structures on the device can range in size from ~1 micron to several centimeters or more in large scale or macroscopic versions of these devices. Permeation layers and/or template materials may be placed over such devices which would allow the devices to be used to carry out multi-step and multiplex synthesis reactions and fabrication steps on substrate materials. Thus, devices can be used for multi-step and multiplex reactions and fabrication on "themselves"; as well as manufacturing devices, which produce the assembled systems on various substrate materials. We define "multi-step" processes as these which have more than one synthesis or fabrication step at one or more locations on the device; and "multiplex" as processes involving the synthesis or fabrication of different components on different locations on the device.

FIG. 40 shows the process by which multi-step transport and positioning of nanospheres or nanoparticles can be carried out using such devices. In this sequence of figures, negatively charged nanostructures (type 1) are transported and concentrated from the bulk solution onto specific microlocations on the left side of the array. This is achieved by biasing the microlocations positive, relative to the control electrodes biased negative. The negatively charged type 1 nanostructures within the electric field are transported and concentrated (electrophoretically) at the specific microlocations. The type 1 nanostructures can be various devices or structures which have specific DNA sequences which allows them to hybridize at other specific locations on the device itself or to other nanostructures which contain complimentary DNA sequences.

In the next step, type 2 nanostructures are transported and concentrated at specific microlocations on the right side of the device. In the next steps, the type 1 nanostructures are transported to specific microlocations at the center of the array which have complimentary DNA attached. The type 1 nanostructures are transported to specific microlocations at the center of the array which have complimentary DNA attached. The type 1 nanostructure hybridize and become specifically attached to these locations. The type 2 nanostructures are now transported to the same center location, as the type 1 nanostructures. The type 2 nanostructures are now transported to the same center location as the type 1 nanostructures. The type 2 nanostructures contain attached DNA sequences which are complimentary to the type 1 nanostructures. The type 2 nanostructures hybridize and become a bound layer over the type 1 nanostructures.

Figure 41:
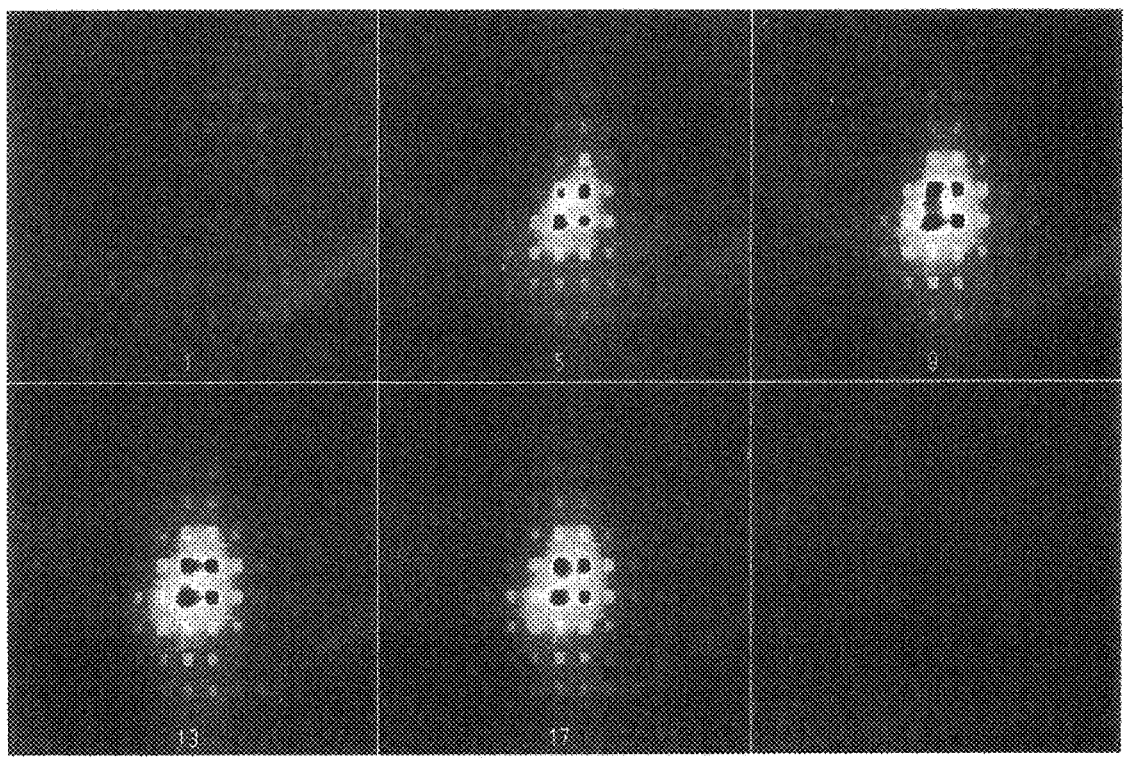
FIG. 41 shows images of an 8×8 array.

This sequence of steps in FIG. 40 is meant to depict only one of numerous multi-step and multiplex fabrication scenarios which can be carried out with these devices and self-assembling nanostructures, submicron and micron sized structures to which specific DNA sequences are attached. We refer to these processes as electric field assisted self-assembly of DNA derivatized structures. By way of example, FIG. 41 shows a sequence of photos which demonstrate the transport of 200 nanometer sized fluorescent nanospheres to selected microlocations on an 8×8 microelectrode array device. The microlocations are 50 m×50 m in size. The negatively charged 200 nm fluorescent nanospheres are rapidly transported and concentrated onto the positively charged microlocations. In other experimental work, nanospheres have been moved from one location to other locations on the device; and it is possible to form various patterns or arrangements of nanostructures on these devices.

Positioning and Orientation of Large Structures

Figure 42:
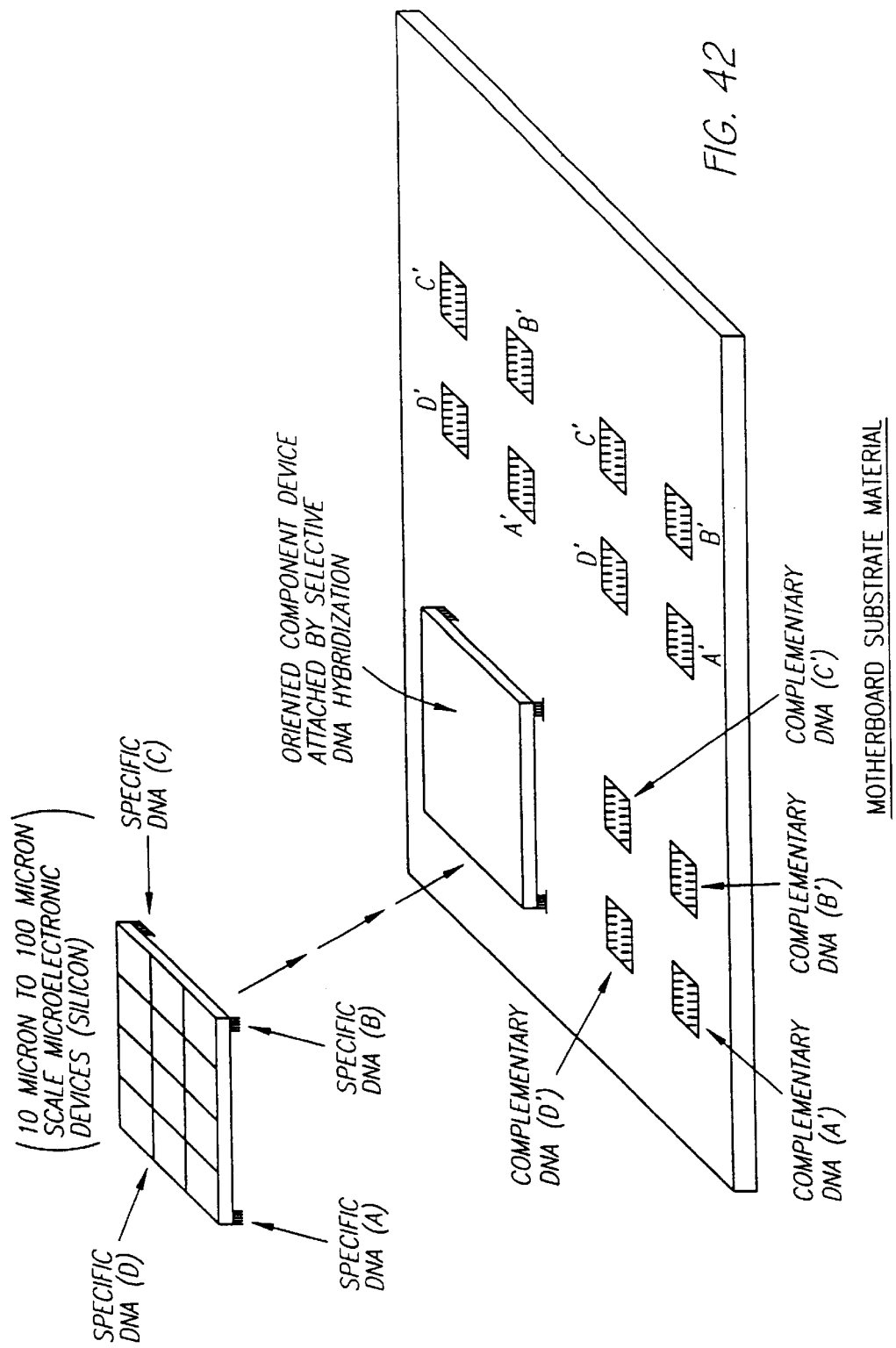
FIG. 42 shows an apparatus for attachment and orientation of larger sized devices onto a substrate or motherboard.

One useful application of this invention involves the attachment and orientation of larger (10–100 micron) sized devices onto substrate or motherboard materials. This process is shown in FIG. 42. In this example, a device is selectively derivatized with four different DNA sequences, and the motherboard is selectively derivatized with the four complimentary sequences. The devices are then allowed to hybridize and attach to the motherboard substrate by the processes which were described in earlier sections on passive and active electric field methods for hybridization.

Nanofabrication Within Microelectronic Parameters

Figure 43:
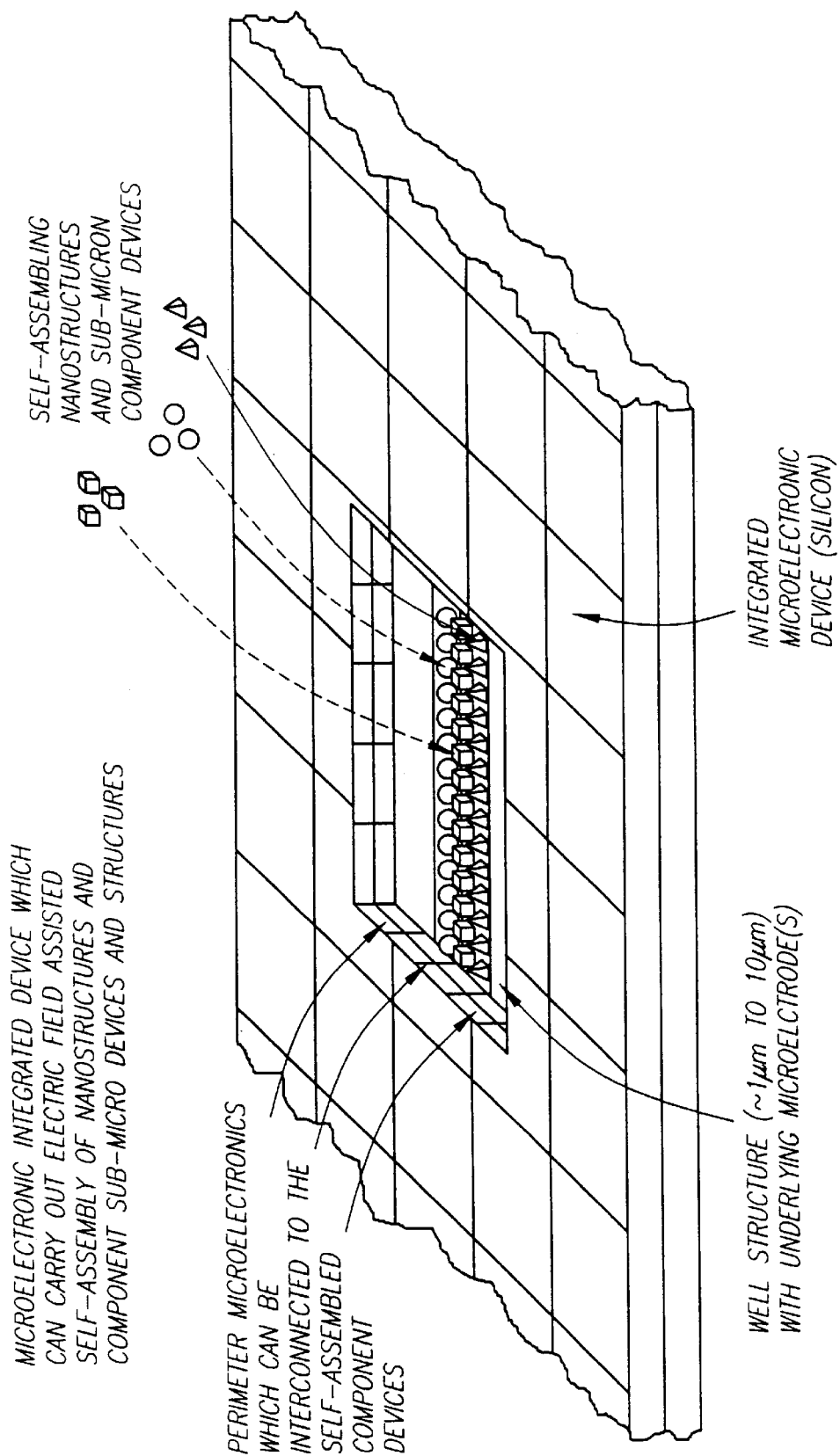
FIG. 43 shows an apparatus for fabrication of nanostructures.

Within the scope of this invention are applications which involve the nanofabrication of arrangements of nanostructures and sub-micron devices wtihin parameters of microelectronic, optoelectronic, and optical components. In these cases, microelectronic deivces are designed and built by classical procedures, but contain areas which are designed for self-assembly of nanostructures and sub-micron cmponents. By way of example, FIG. 43 shows one such device. In this example, a microelectronic device built in silicon using classical photolithographictechniques, has a well structure with an underlying micro microelectrode. This microelectrode is now used to carry out the electric field assisted self-assembly of various nanostructures and sub-micron components within the parameter of the microelectronic components. This technique allows interconnection between the microelectronic components and the nanoscale components, as well as the creation of much denser integrated devices including arrangements of multiple layers (3D fabrication) of components. Thus, this invention is considered a way to synergize both classical microelectronics (optoelectronic) fabrication techniques, with self-assemblying nanofabrication techniques.

Nanofabrication Within Nanoscale Parameters

Figure 44:
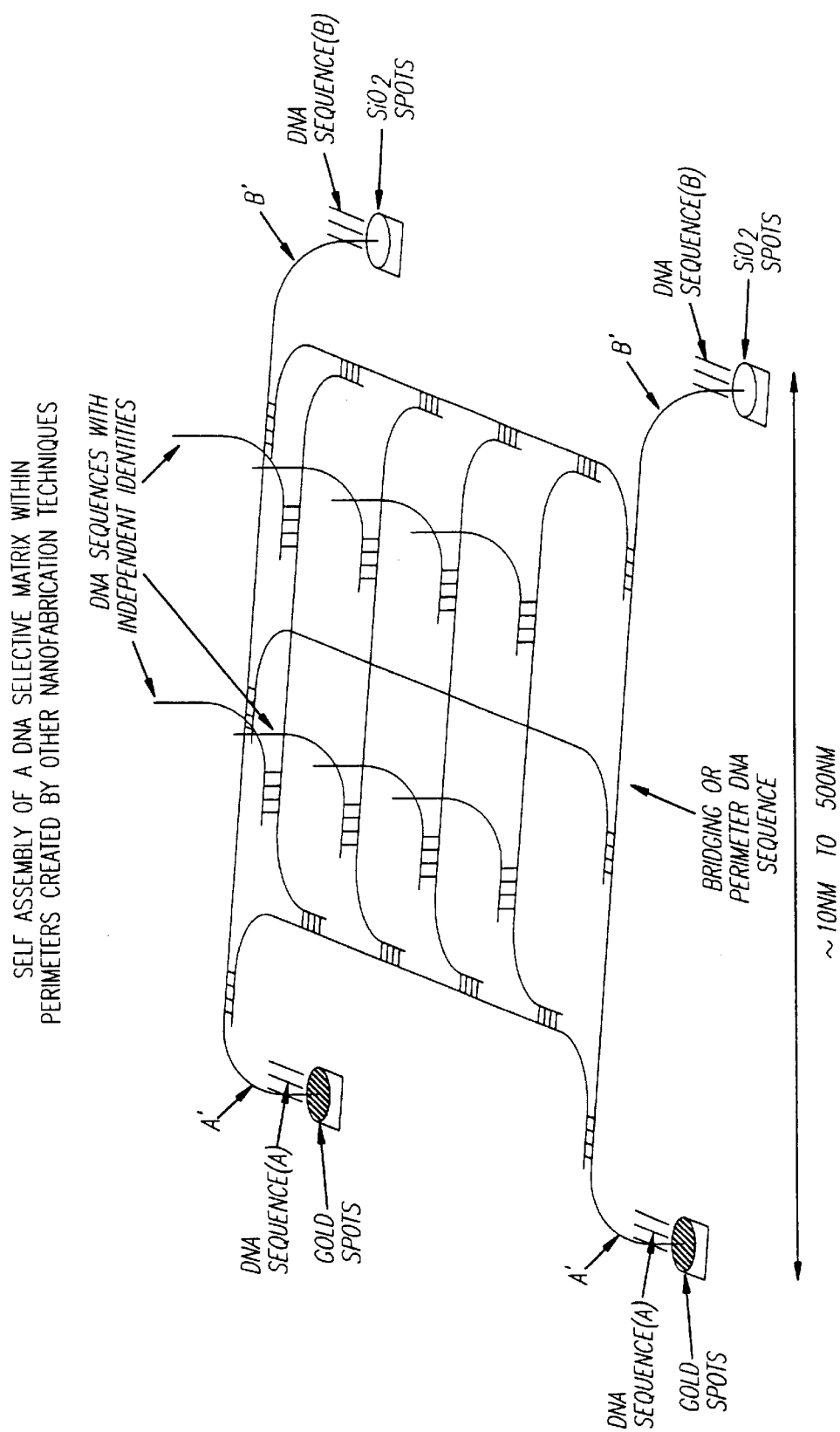
FIG. 44 shows an apparatus for nanofabrication of a nanoscale device.

Within the scope of this invention are techniques which allow the nanofabrication of the matrix of selective binding DNA sequences to be assembled with a group of nanoscale or sub-micron positions which have been deposited by atomic force, microscope, e-beam, or other sub-micron fabrication techniques. FIG. 44 shows an example of this methodology. In this example, four sub-micron attachment structures are deposited onto a suitable substrate material. Two of the structures are of mataerial which can be selectively activated for subsequent attachment of DNA sequences (i.e., gold for thiol attachment chemistry). The other two, of a material which can be selectively activated for another specific attachment chemistry (i.e., silicon dioxide for silane aldehyde/amine attachment chemistry). From these positions two different DNA sequences can be attached. In further steps, complimentary DNA sequences are hybridized which span the two different locations forming a square parameter. From proper position of other DNA sequences can be hybridized to the parameter DNA, ultimately forming a matrix structure which has selective hybridization sites within the matrix. From these types of matrix nanostructures (with selective DNA identities) a variety of two and three dimensional nanofabrications can be carried out.

Methods and Apparatus for Optical Writing

Figure 6:
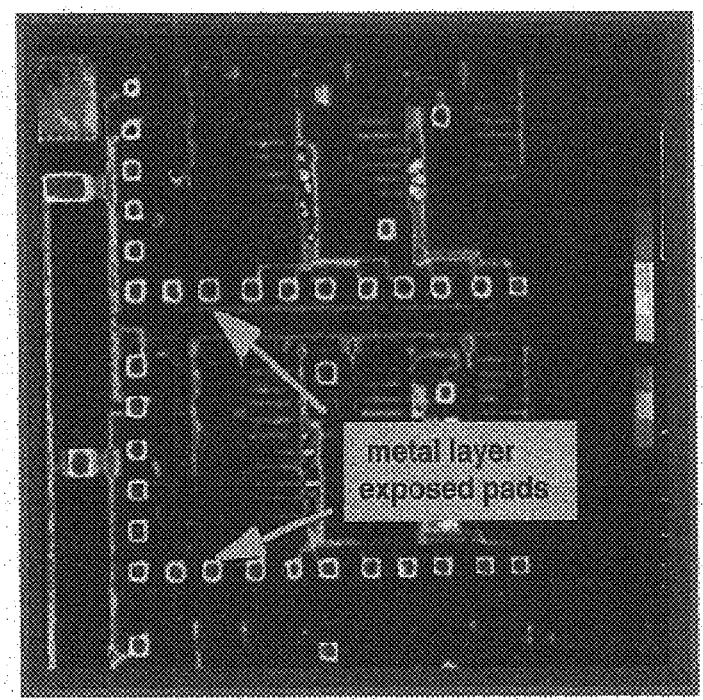
FIG. 6 shows a plan view of a structure for selective attachment of fluorescent DNA sequences to aluminum pads on silicon VLSI chips.

DNA optical storage involves the design and synthesis of chromophoric DNA polymers which absorb light energy at a single wavelength and re-emit at predetermined multiple wavelengths. Our work shows that DNA polymers can be attached in a self-organized manner to solid surfaces and made into unit cells that have the designed functionality. We demonstrated that DNA polymers attached to solid surfaces could exhibit multiple chromophoric responses, photonic energy transfer, and quenching. FIG. 6 and FIG. 7 show results related to attachment of fluorescent DNA polymers to silicon dioxide and aluminum surfaces and UV writing (imaging) into monolayers of DNA on the surface of these substrates.

UV Write Mechanism for DNA Optical Storage

Four different mechanisms exist by which information can be written into DNA substrate materials: i) spatial UV inactivation of thymidines within DNA sequences; ii) spatial UV inactivation of fluorophores and chromophores; iii) spatial UV inactivation or activation of quencher chromophores; and iv) spatial UV activation or inactivation of subsequent hybridization by crosslinking (e.g., psoralens).

Figure 8A:
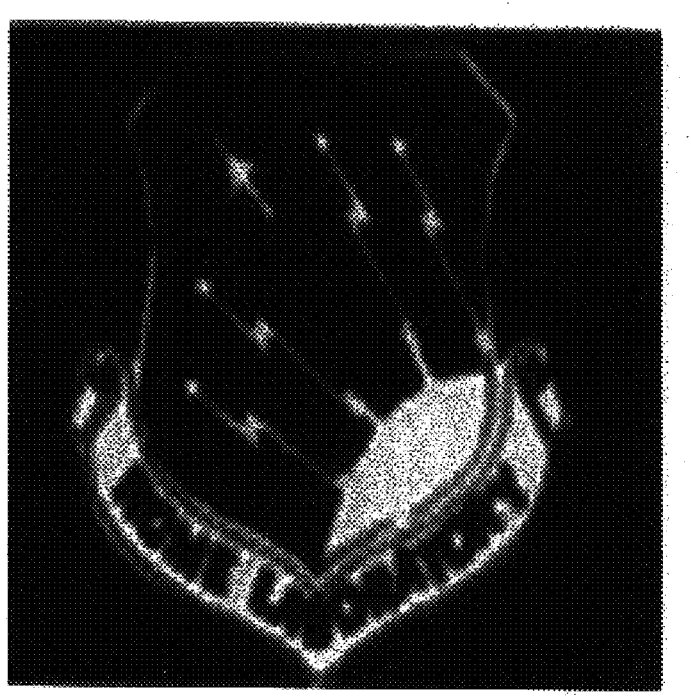
FIG. 8A is a plan view of a UV image mask write followed by hybridization into DNA optical storage material.
Figure 8B:
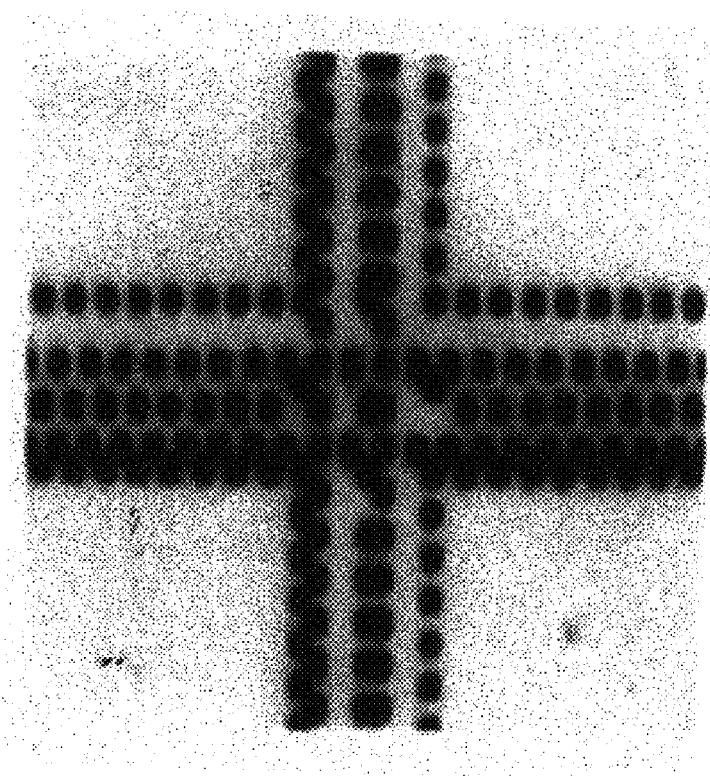
FIG. 8B is a plan view of a UV image mask write into DNA optical storage material (10 micron resolution).

FIG. 8a and b shows UV write/hybridization results using a logo mask and a four color write mask. These represent images that are produced in monolayers of DNA on silicon substrates to which complementary fluorescent DNA sequences are hybridized.

UV/psoralen Write Process—Step 1

Regarding the UV/psoralen write process, FIGS. 9 thru 19, schematically show the complete process for preparing a "four identity DNA substrate material".

This process imparts multiple DNA identities in substrate materials using psoralen crosslinking agents. DNA intercalated psoralen compounds when exposed to low-energy UV light (365 nm) are able to covalently crosslink the DNA strands together. Linking DNA strands together with psoralen allows creation multiple identities on substrate surfaces.

Figure 9:
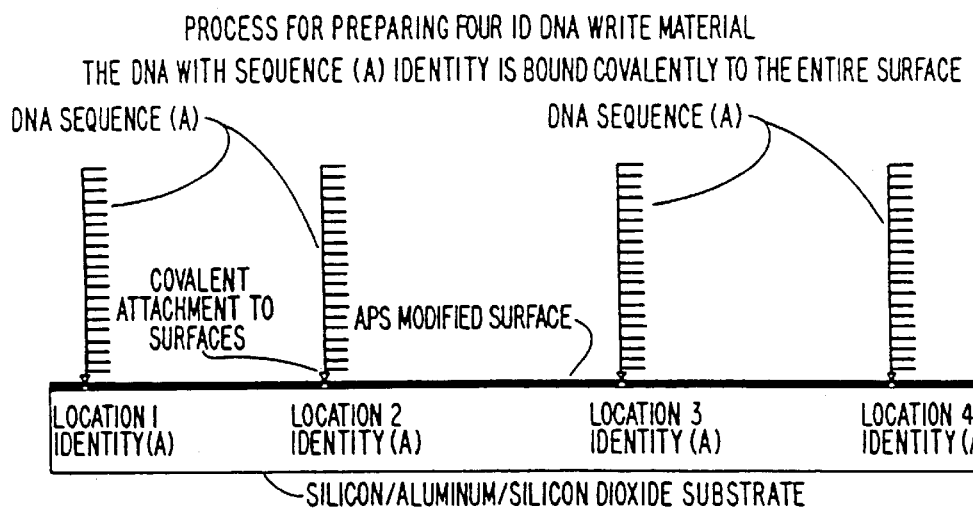
FIG. 9 is a cross-sectional view of an apparatus and method for preparing multiple write materials.

FIG. 9 shows DNA sequences with identity (A) covalently attached to the Silicon/Aluminum/Silicon Dioxide substrate surface. The chip surface is first reacted with aminopropyltriethoxysilane (APS) reagent, which provides amine groups on the substrate surface for attaching the DNA sequences. The capture DNA sequences (A) are functionalized in their terminal position with a ribonucleoside group which is subsequently oxidized to form an amine reactive dialdehyde group. The DNA (A) sequences can now be covalently coupled to the amine groups on the APS functionalized substrate surface. For purposes of illustration the figures show four individual DNA strands as a way to depict the four potential write identity quadrants (refereed to as locations in the figures). In the actual material there are from ~$2.5 \times 10^4$ to $2.5 \times 10^5$ DNA strands per quadrant (quadrant size is preferably about 250 nm square).

Figure 10:
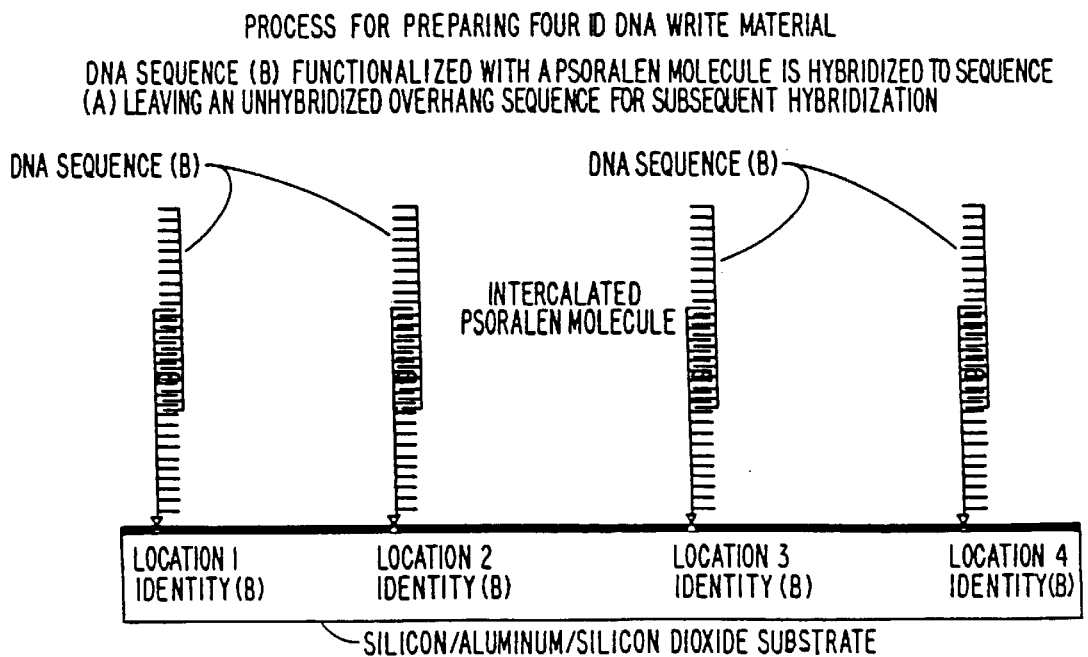
FIG. 10 is a cross-sectional view of a step in the process for preparing DNA write materials.

FIG. 10 shows the write identity process is initiated by hybridizing a (B) identity psoralen modified DNA sequence that is also partially complementary to the (A) identity capture sequence existing in all four quadrants (locations). The psoralen molecules intercalate within the hybridized double-stranded DNA.

FIG. 11 shows a UV mask is now used to block quadrant 1, while quadrants 2, 3 and 4 are exposed. The unmasked quadrants (2, 3 & 4) are irradiated with low-energy UV light (365 nm). The UV exposure causes the intercalated psoralen molecules within the hybridized double-stranded DNA to covalently crosslink the strands.

FIG. 12 shows the entire surface is now subjected to a dehybridization process. The non-crosslinked (B) identity DNA sequence in quadrant 1 is removed, leaving the (A) identity DNA sequence in that position. Quadrants 2, 3 & 4 now have the (B) identity DNA sequence in their positions.

Figure 13:
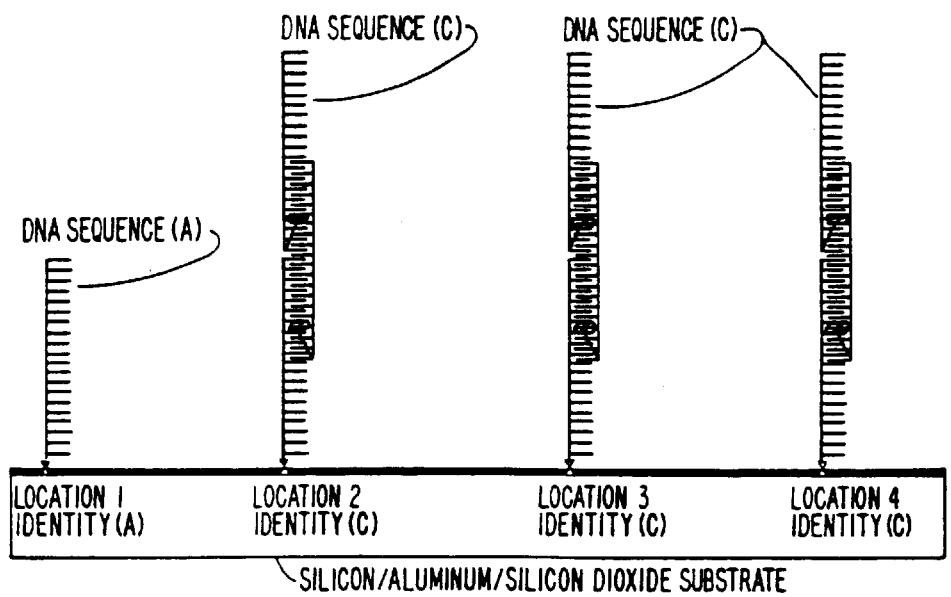
FIG. 13 is a cross-sectional view of a step in the process for preparing DNA write materials.
Figure 14:
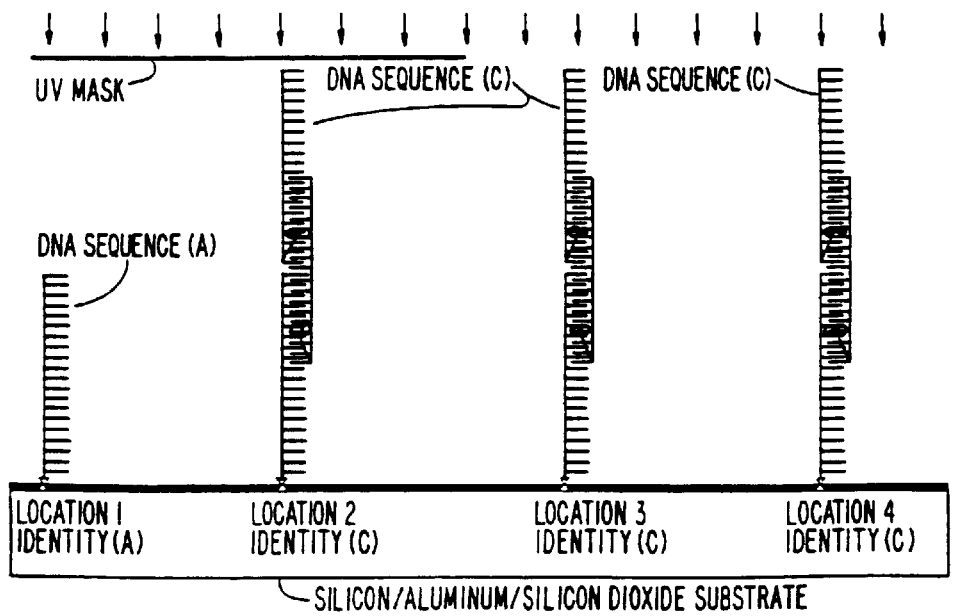
FIG. 14 is a cross-sectional view of a step in the process for preparing DNA write materials.
Figure 15:
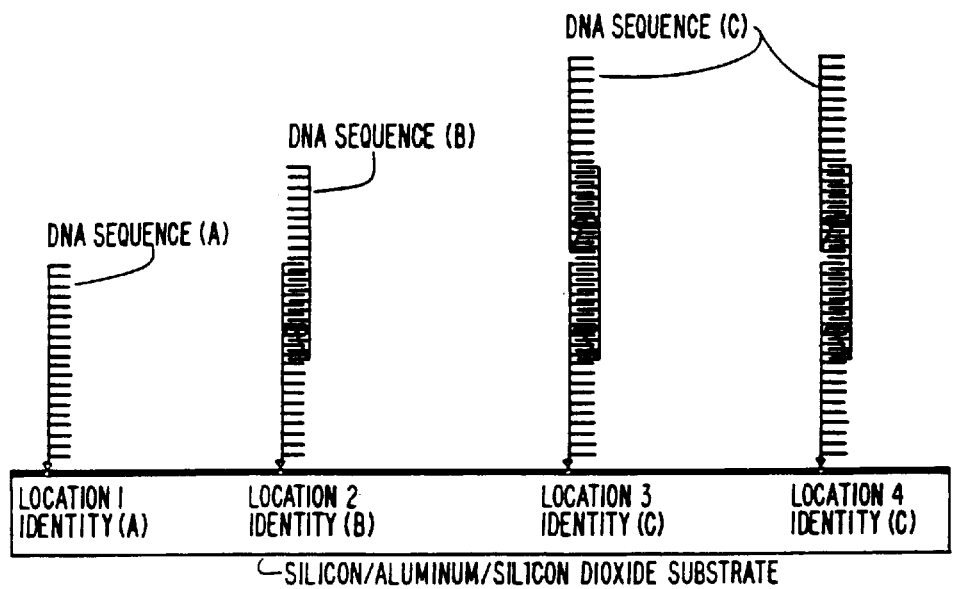
FIG. 15 is a cross-sectional view of a step in the process for preparing DNA write materials.
Figure 16:
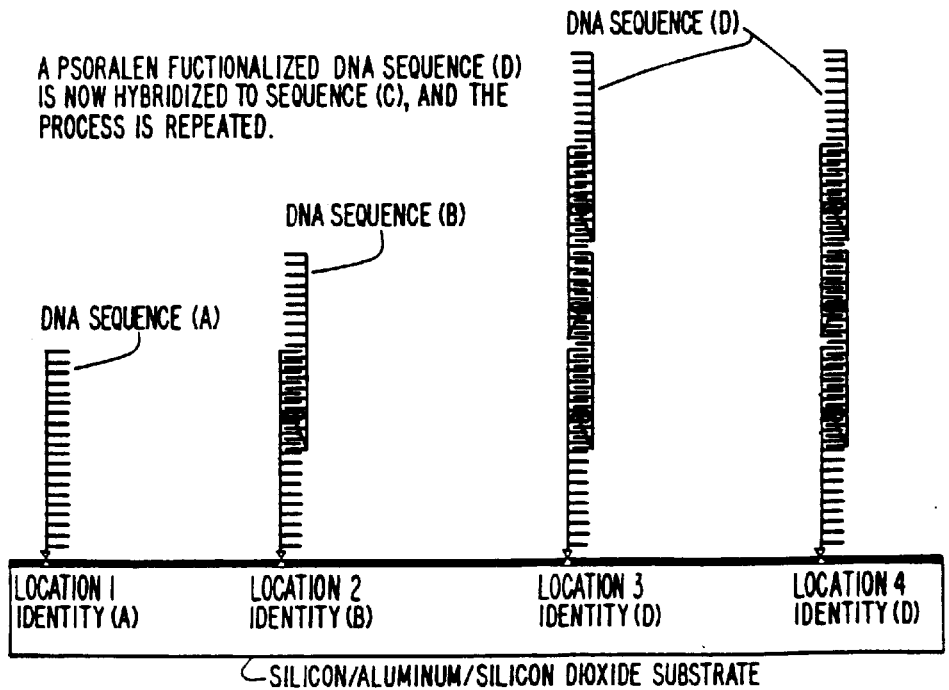
FIG. 16 is a cross-sectional view of a step in the process for preparing DNA write materials.
Figure 17:
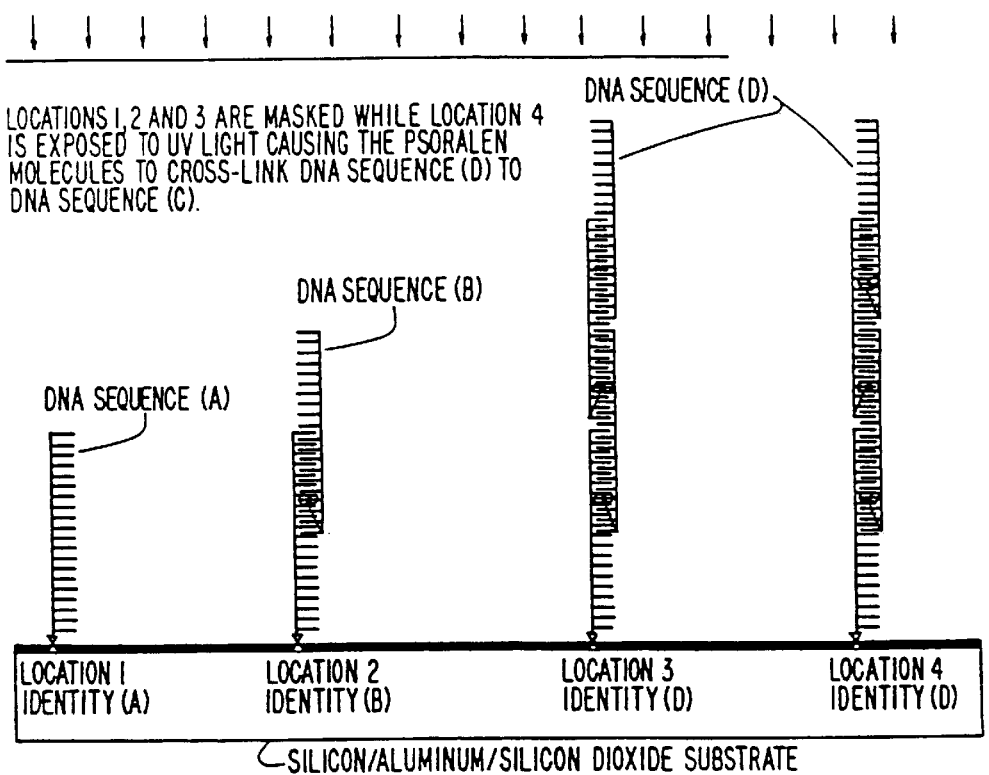
FIG. 17 is a cross-sectional view of a step in the process for preparing DNA write materials.
Figure 18:
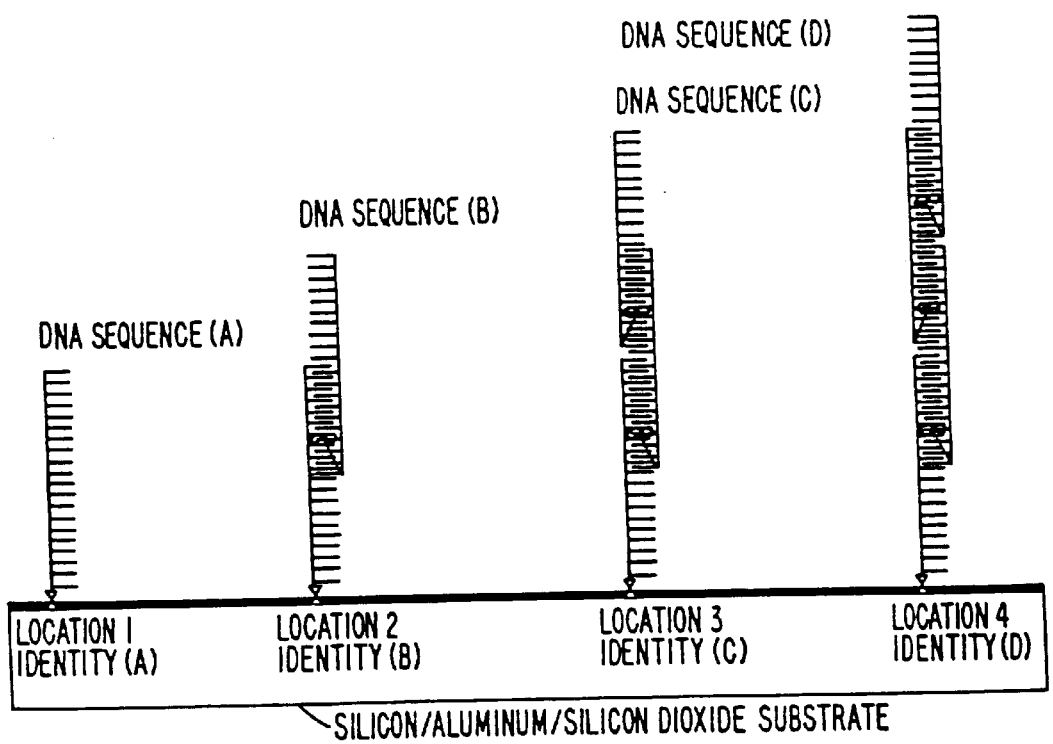
FIG. 18 is a cross-sectional view of a step in the process for preparing DNA write materials.

FIG. 13 shows the process is now repeated with a (C) identity DNA sequence, containing the partial (B) identity DNA complement, being hybridized to the (B) sequence in quadrants 2, 3 and 4.

FIGS. 14 thru 18 depict essentially the repetition of the processes shown in FIGS. 9 thru 13. When completed, the final material contains four separate DNA identity sequences (A, B, C, & D) each located in a separate quadrant.

Figure 19:
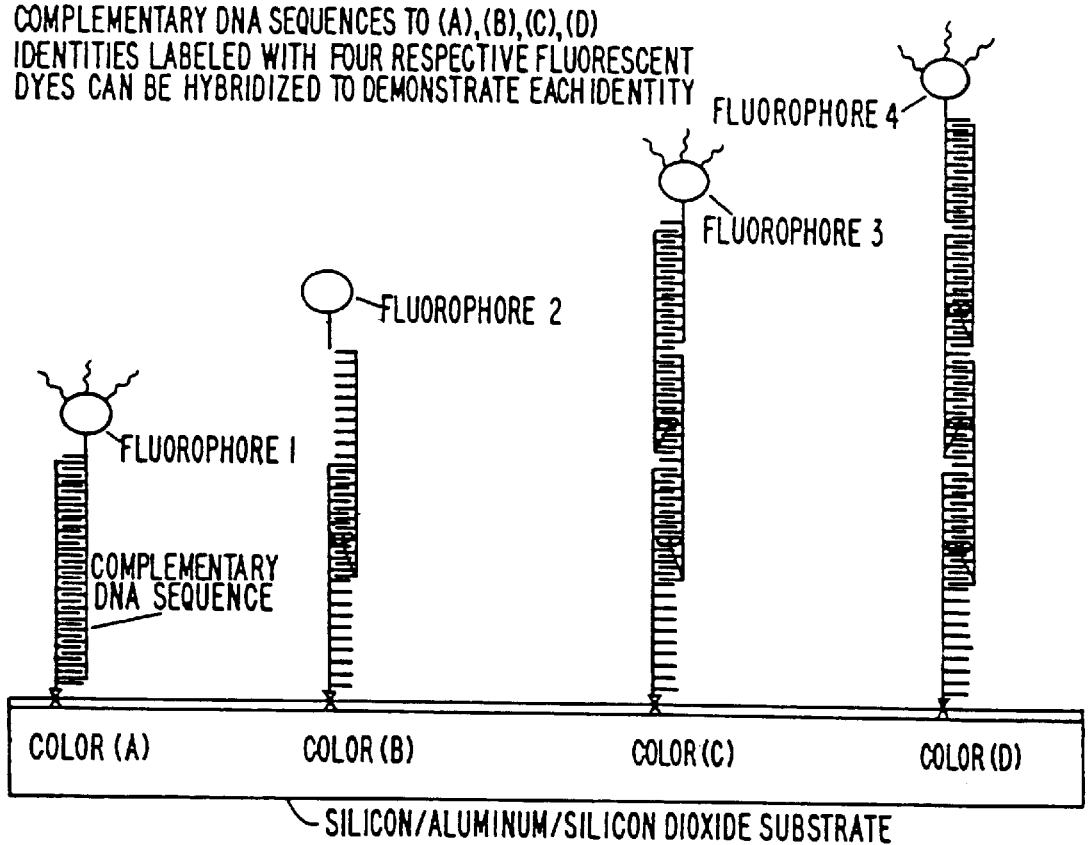
FIG. 19 is a cross-sectional view of a step in the process for preparing DNA write materials.

FIG. 19 shows, at this point, where one can check the specificity of the four DNA sequences (A, B, C, & D) by hybridizing the four fluorescently labeled complementary sequences to the surface. Each quadrant should now produce its specific fluorescent color.

UV/psoralen Write Process—Step 2

Figure 20:
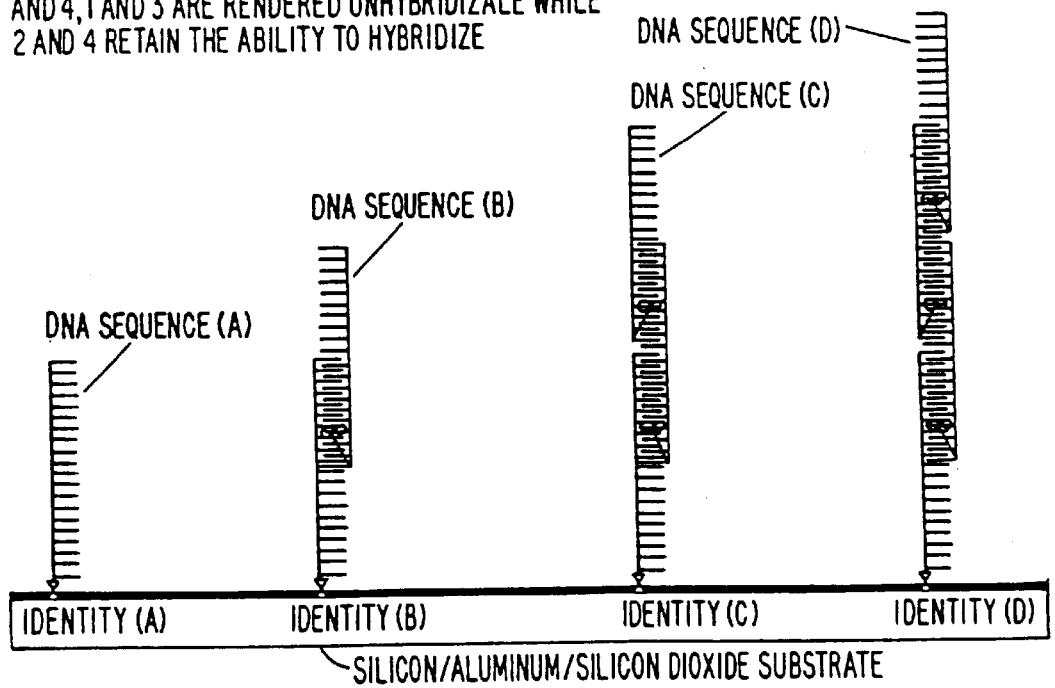
FIG. 20 is a cross-sectional view of a step in the process for preparing DNA write materials.

The actual information UV write process (to the four DNA identity substrate) is carried out by another masking and UV exposure procedure (see FIGS. 20, 21, and 22). In this case, a higher energy UV irradiation (254 nm) is used to render the DNA in the UV exposed regions non-hybridizable. When DNA is exposed to this higher energy UV light, the thymidine bases within the DNA sequence dimerize and prevent any further hybridization from occurring. This procedure can thus be used to inactivate the individual quadrants or "turn them off". When the fluorescently labeled complementary DNA sequences are hybridized to the material, only the quadrants with hybridizable complementary DNA sequences will have the appropriate fluorescent color. This is the mechanism by which data can be selectively written into DNA.

FIGS. 20 & 21 show turning "On" the B and D identities, and turning "Off" the A and C identities. Before the UV write process is started, the specific A, B, C, & D sequences in all four quadrants 1, 2, 3, & 4 are hybridizable. The write process is initiated by masking quadrants 2 and 4, and exposing the surface to the high-energy (254 nm) UV irradiation. Quadrants 1 and 3 are now effectively inactivated or made unhybridizable by UV exposure, while the DNA sequences in 2 & 4 remain hybridizable.

FIG. 22 shows how the material can now be hybridized with the fluorescent DNA complements to all four DNA identities, however, only the fluorescent DNA complements to the B and D identities will effectively hybridize and produce the final fluorescent colors. The UV write process being completed, the material now has two distinct fluorescent colors in the B and D quadrants, and no fluorescent colors in the A and C quadrants.

Experimental Demonstration of Two Color DNA Write Process

Figure 23A:
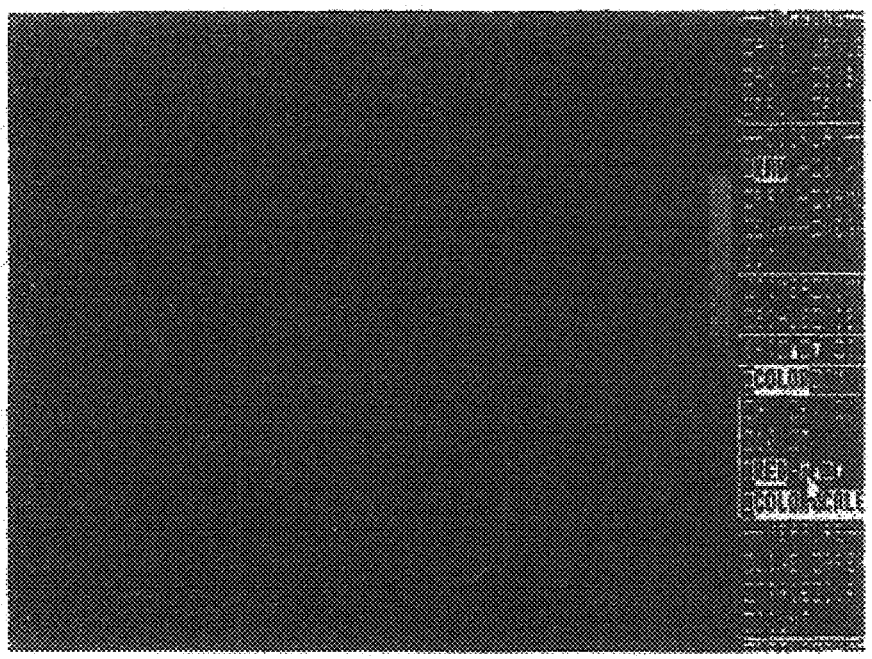
FIG. 23A is a planned image of the background fluorescence for APS-reacted silicon substrate surface before DNA attachment.
Figure 27A:
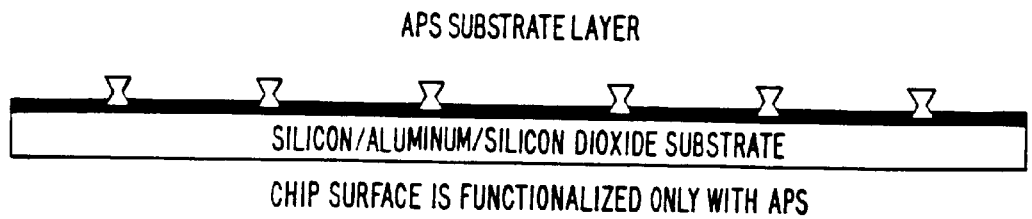
FIGS. 27A–C are cross-sectional views of apparatus and method steps for forming fluorescently labeled sequences.

We have demonstrated two color write using the psoralen/UV process. The series of process and write steps are described below in the text. FIGS. 23A & B, 24 A&B, and 25 A&B show the actual photographs of the substrate and fluorescent write materials. FIGS. 27A, B&C, and 28A, B&C, provide further schematic descriptions of the process.

Figure 23B:
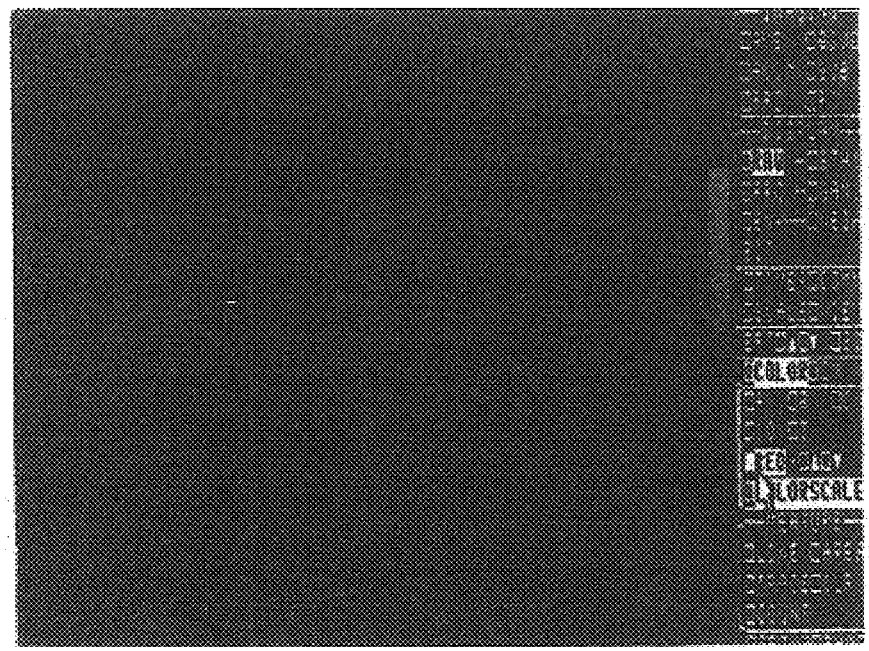
FIG. 23B is a planned image of the background fluorescence level after capture DNA is bound to the APS-reacted substrate.
Figure 27B:
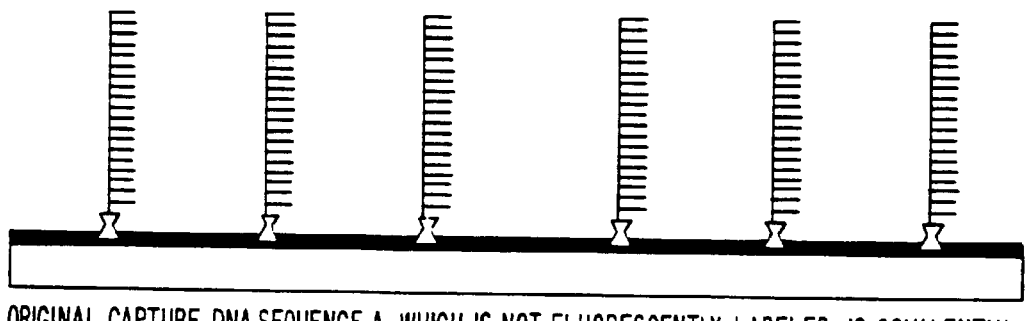
Figure 27C:
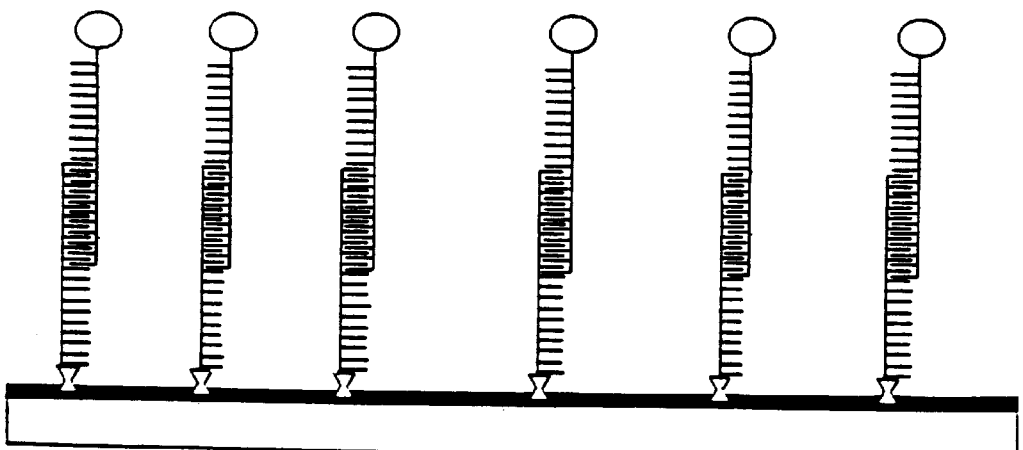

Step 1: A control chip surface (Silicon Dioxide/Aluminum/Silicon)was treated with Aminopropyltriethoxysilane (APS). FIG. 23-A shows the chip surface appears basically black, because of the relatively low level of background fluorescence. FIG. 27-A is a schematic representation of the material at this point of the process. All photographs were taken using the Jenalumar Epi-fluorescentmicroscope/Hammamatsu Intensified CCD Camera/Argus Ten Imaging system.

Step 2: A second control chip surface (APS reacted) was then reacted with the DNA (A) identity capture sequence that contains the proper base composition for subsequent psoralen crosslinking. The DNA (A) sequence has a ribo group on the 3' end that is oxidized to a dialdehyde, this reacts with the amine groups on the surface to covalently attach the DNA. FIG. 23-B shows a photograph of the substrate surface with the DNA (A) present, but without any fluorescent complementary DNA present. The chip surface still appears black, because of the relatively low level of background fluorescence. FIG. 27-B is a schematic representation of the material at this point of the process.

Figure 24A:
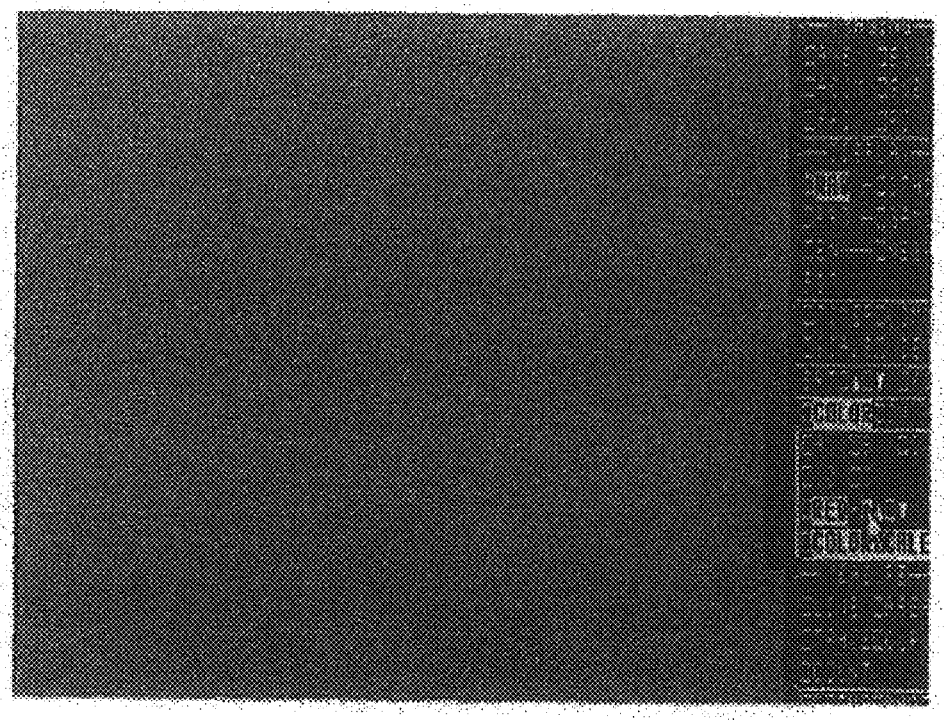
FIG. 24A is a planned image of a chip treated with APS and capture DNA and then hybridized with a Bodipy Texas Red labeled complementary probe sequence across the entire chip surface.
Figure 24B:
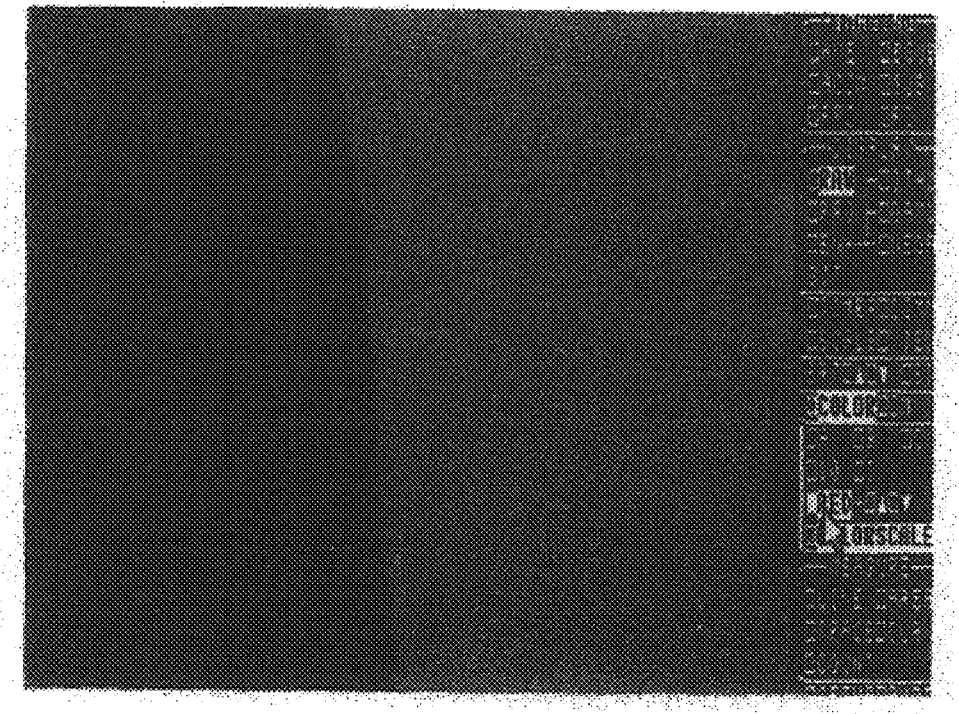
FIG. 24B is a planned image of the chip surface after hybridization of a fluorescent Bodipy Texas Red labeled complementary probe to the non-psoralen cross-linked identity on the right side of the chip surface.

Step 3: A third control chip surface which has been APS reacted and has the DNA (A) capture sequence attached, is hybridized with a Bodipy Texas Red fluorescently labeled complementary sequence. FIG. 24-A now shows the entire chip surface producing intense red fluorescence. FIG. 27-C is a schematic representation of the material at this point of the process.

Step 4: A fourth chip is treated with APS and (A) identity DNA capture sequence is then bound to the surface as in Step 2.

Step 5: The complementary (B) identity sequence, with a psoralen molecule attached, is then hybridized to the (A) identity sequence over the entire surface.

Step 6: One half of the chip surface is masked, while the other half is exposed to low-energy (365 nm) UV light. This causes the covalent crosslinking of the (A) identity DNA sequence with the (B) identity DNA sequence.

Step 7: The surface is then treated with a 0.1 normal Sodium Hydroxide solution to remove (dehybridize) the non-crosslinked DNA from the masked side of the chip. At this point one half of the chip is covered with covalently linked (B) identity DNA sequence, and the half contains the original (A) identity DNA sequence.

Figure 28A:
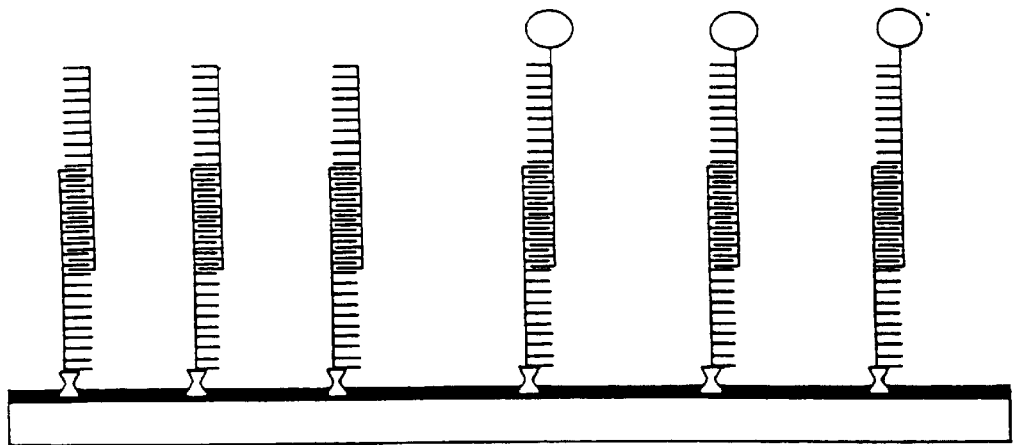
FIGS. 28A–C are cross-sectional views of apparatus and method steps for providing multicolor images.
Figure 28B:
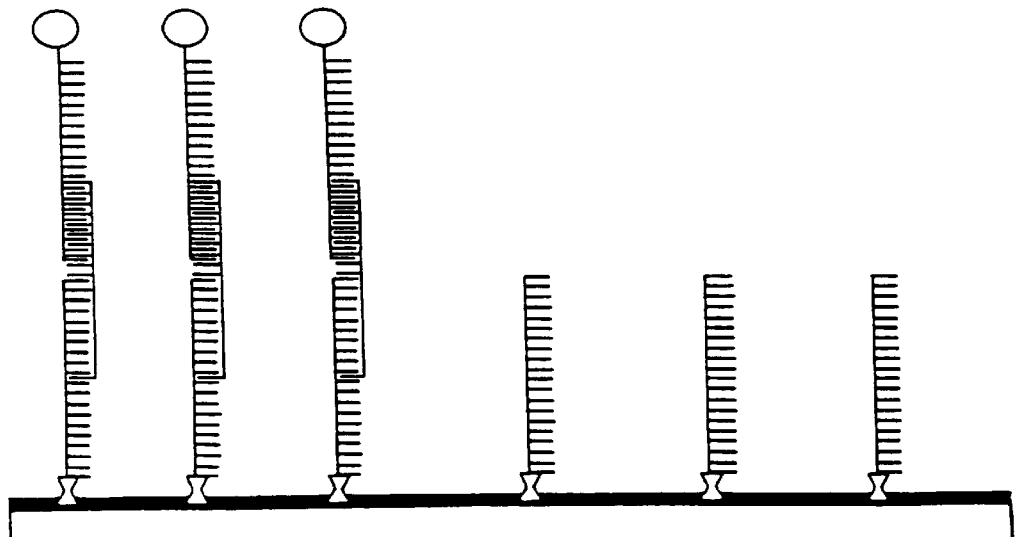
Figure 28C:
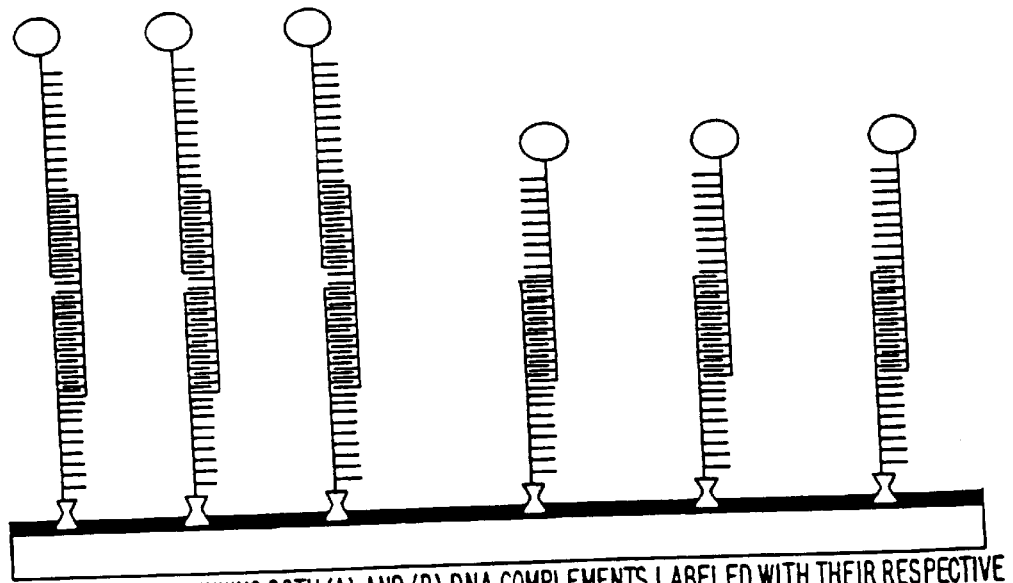
Figure 29:
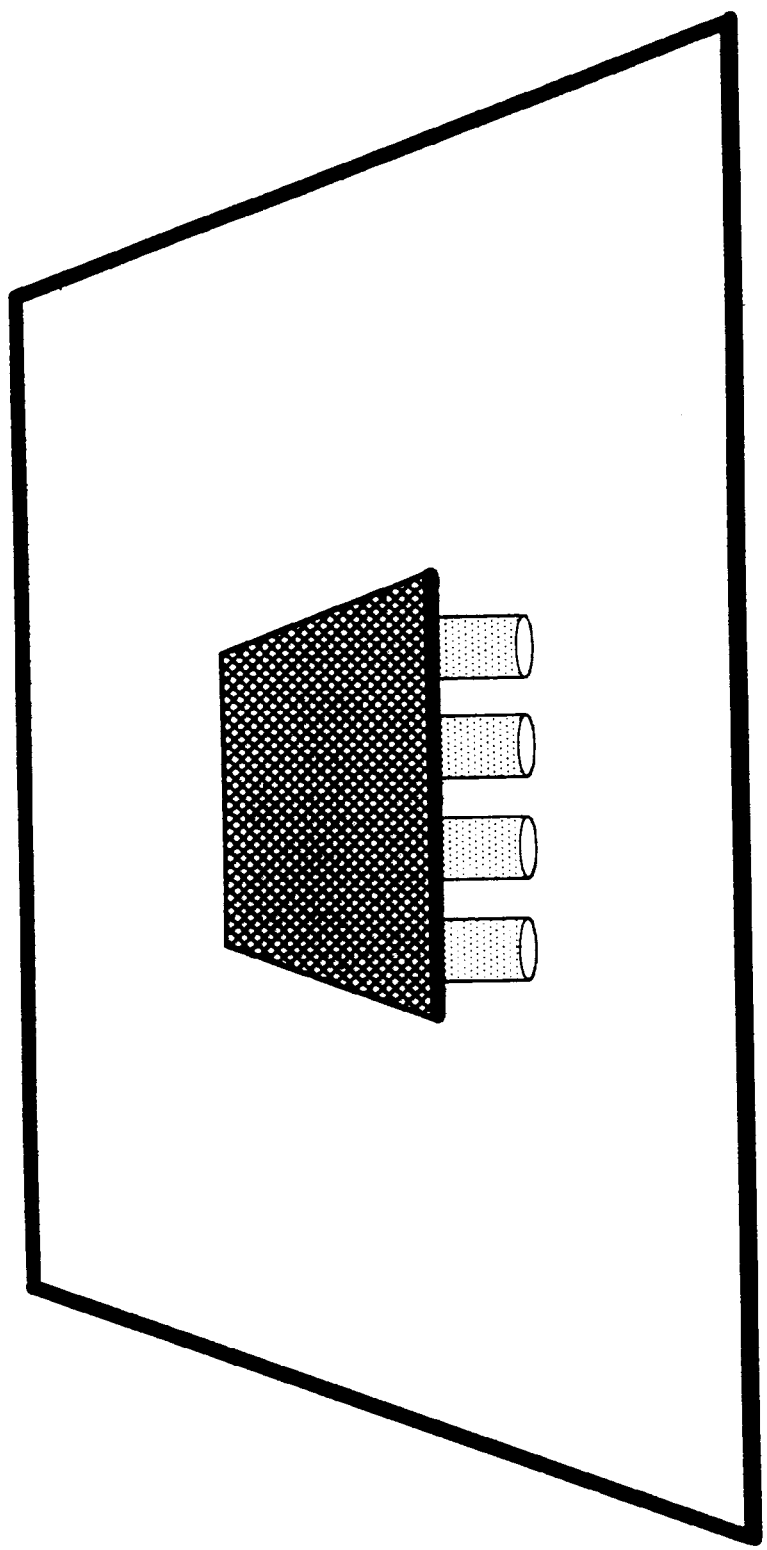
FIG. 29 is a perspective view of a flip-chip bonding arrangement which conserves the geometrical dimensions leading to the coupling of small dense arrays of specialty devices onto local regions of mother boards.

Step 8: A complementary (A) identity DNA sequence labeled with Bodipy Texas Red fluorescent dye (excitation maximum 595 nm and emission maximum 626 nm) is now hybridized to the chip. The complementary fluorescent (A) identity DNA sequence hybridizes only to the half of the chip surface containing the (A) identity capture sequence (FIG. 24-B). FIG. 28-A is a schematic representation of the material at this point of the process. Steps 4 thru 7 are repeated on a fifth chip surface.

Figure 25A:
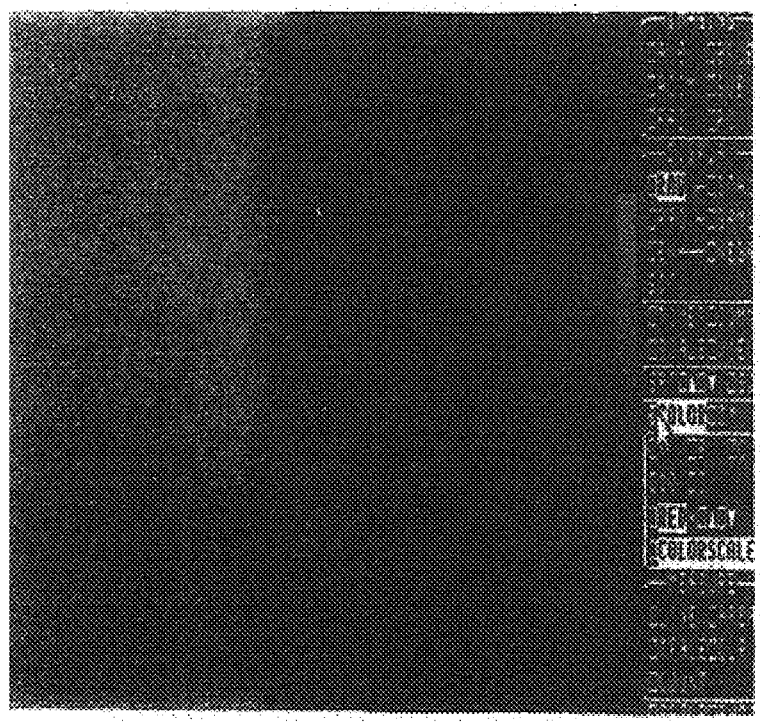
FIG. 25A is a plan image of the chip surface after hybridization of a fluorescent Bodipy Orange (b) complimentary probe to the (b) sequence identity on the left side of the chip surface.
Figure 25B:
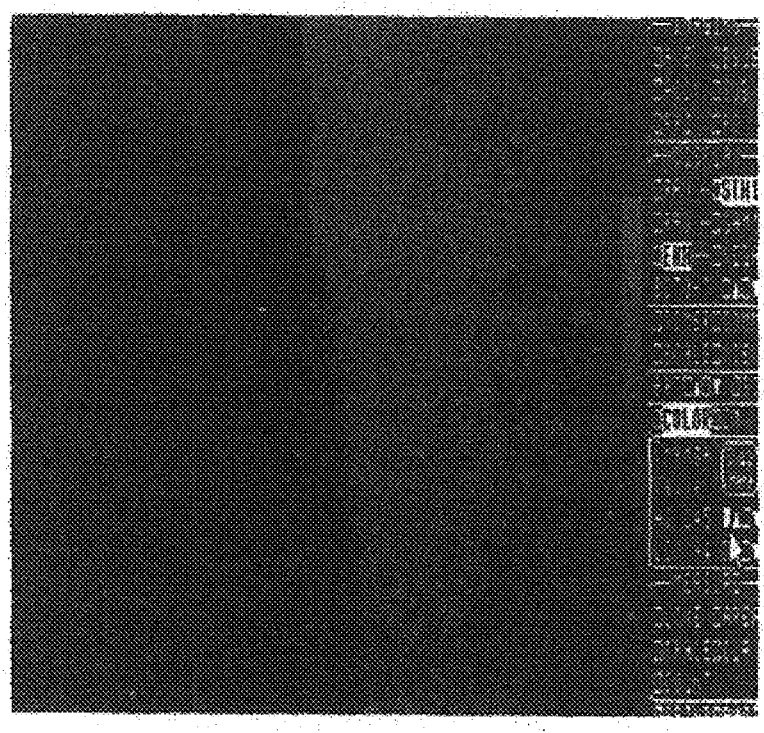
FIG. 25B is a plan image of the chip after both cross-linked (B) and non-cross-linked (A) sides are hybridized with their respective fluorescently labeled complimentary DNA (A) and (B) probes.

Step 9: A Bodipy Orange fluorescent dye (excitation maximum 558 nm and emission maximum 568 nm) labeled sequence complementary only to the (B) identity sequence is then hybridized across the whole chip. This DNA sequence hybridizes only to the half of the chip containing the (B) identity (FIG. 25-A). FIG. 28-B is a schematic representation of the material at this point of the process.

Step 10: A sequence complementary only to the (A) identity capture sequence, labeled with Bodipy Texas Red fluorescent dye is hybridized to the fifth chip. Again this fluorescently labeled DNA attaches only to the half of the chip containing the (A) identity. The chip now contains both identities with their corresponding colors (FIG. 25-B). FIG. 28-C is a schematic representation of the material at this point of the process. With the results showing exclusive hybridization of two distinct sequences to two separate parts of a chip surface (FIGS. 24-B, 25-A & 25-B), we are reasonably confident that the above protocol is indeed capable of producing multiple identities on silicon substrate surfaces.

Experimental Demonstration of 160 nm Nanosphere Binding To Substrate

Figure 26A:
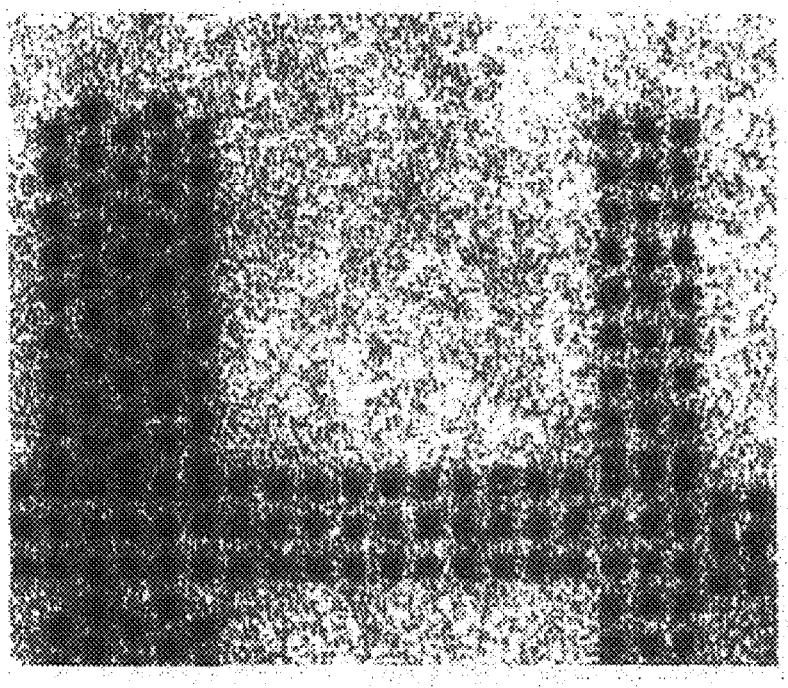
FIG. 26A is a plan image of 160 nanometer beads (white spherical features) electrostatically bound to a DNA polymer layer covalently bound to a silicon dioxide derivatized surface with partial specificity, having 10 micron square dark features where the DNA field has been UV inactivated, the nanospheres not binding in these areas.
Figure 26B:
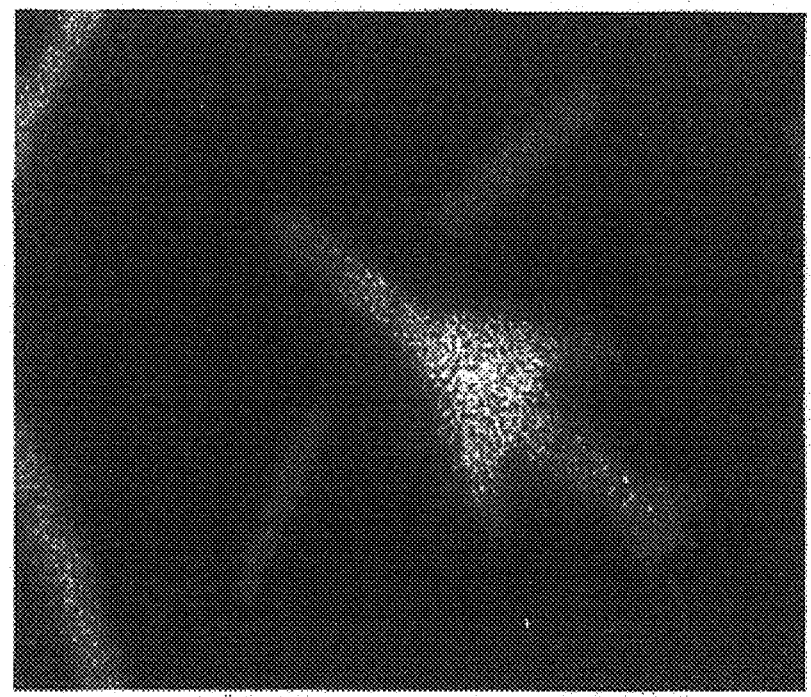
FIG. 26B is a plan image of a pattern image constructed with 160 nanometer beads (white spherical features) wherein the nanospheres are electrostatically bound to a DNA polymer layer covalently bound to silicon dioxide derivatized surface with partial specificity, the dark areas showing areas where the DNA field has been UV inactivated, the nanospheres not binding in these areas.

FIGS. 26A and 26B show results on attaching 160 nm DNA Derivitized fluorescent nanospheres to a DNA Derivitized Derivatized silicon dioxide surface. The nanospheres are bound to the image sections with the active DNA, as opposed to the DNA in-activated sections. The binding is believed to be due to electrostatic as well as to hybridization interactions.

Low Density Optical Memory Applications

A number of important applications of DNA based optical data storage and memory are possible in areas regarding incorporation into documents, currency, labels, and other items. The use of fluorescent energy transfer and chromophoric DNA based mechanism for these "low density" application would have advantages over bar codes and other methods in use becuase of the extreme difficulty in attempting to counterfeit such information or coding.

A Photo-Electronic Optical Memory Write Svstems and Devices

Figure 45:
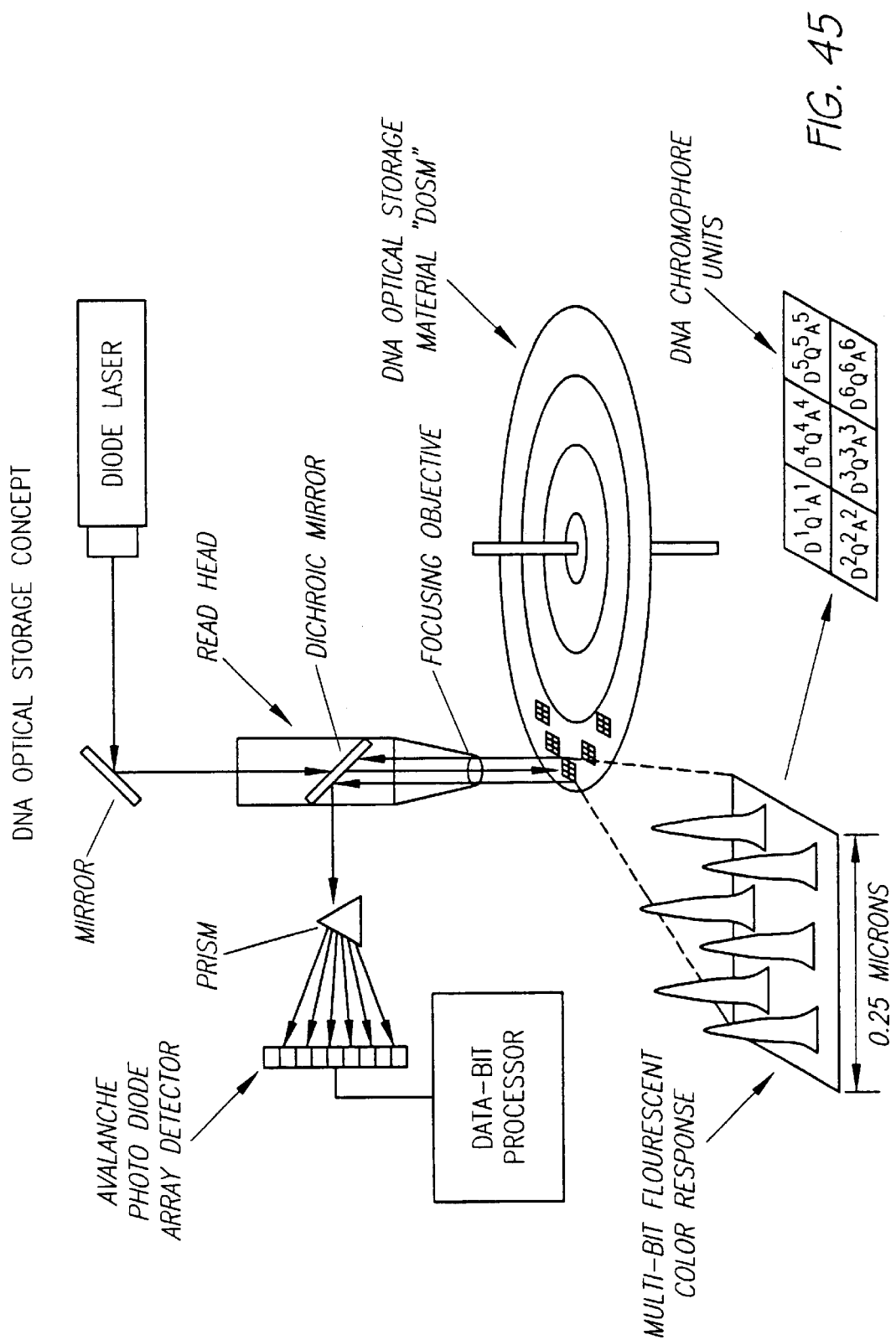
FIG. 45 shows a perspective view of a DNA optical storage system.

DNA polymers may be used for many photonic and electronic applications. One of the main applications using DNA polymers are for high density optical data storage media. In this application, chromophoric DNA polymers absorb light energy at a single wavelength and re-emit at predetermined multiple wavelengths. (See FIG. 45). In one aspect, these inventions relate to a method called photo-electronic write process. This process involves using spatial light addressing to a photoactive substrate material which creates microscopic electric fields, which then affect the selective transport and attachment of charged chromophoric (color) DNA's to these selected locations.

Principles of Operation

Figure 46A:
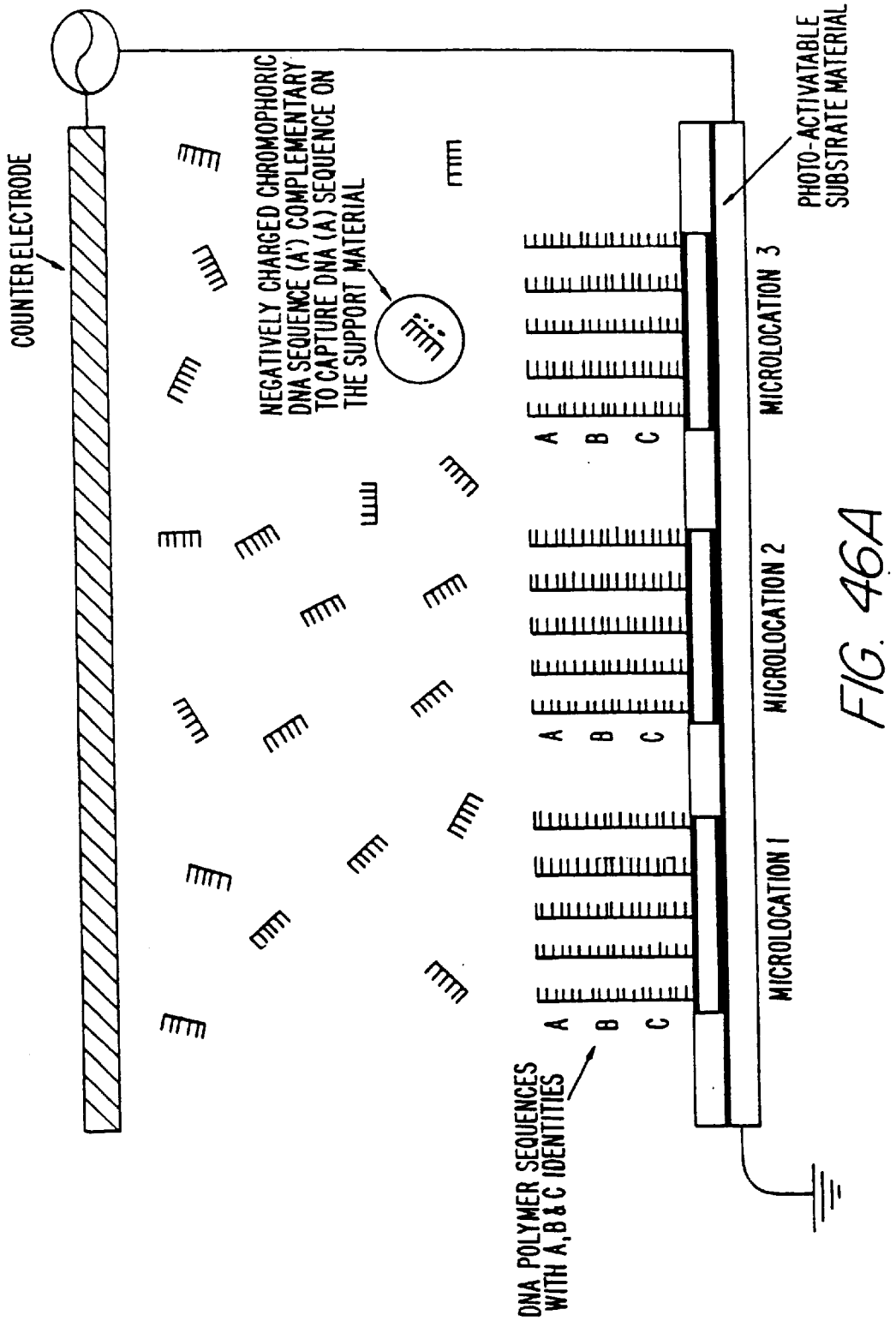

The basic principle involved in the photo/electronic write process is shown in FIGS. 46A and 46B. The proposed write substrate would be a photoelectronic activated matrix material (e.g., a photoconductive film) onto which DNA polymer sequences would be attached. Each of these DNA sequences would have multiple identities. For the sake of illustration, 46A shows three photoactivated sites, which contain DNA sequences with three identities (A, B, & C). A solution containing chromophoric DNA with complementary identity (A') would be exposed to the substrate material, and a counter electrode would be positioned over the solution and lower substrate material. The specific microlocations on the substrate material can now be activated by spatial light addressing which would cause a charge to develop in the material at that location (see FIG. 46B). The production of a charge produces an electric field in the solution which causes the attraction of oppositely charged molecules to the location, or will repel molecules of the same charge identity. Natural DNA would contain a net negative charge, and will migrate to a positively charged location. Synthetic DNA's can be made with net negative charge, net positive charge, or in a neutral state. FIG. 46B shows the light activation of the center microlocation 2, with chromophoric DNA (A') migrating to this location and then binding (hybridizing) to the DNA (A) identity sequence position. When the electric field strength is high enough, the transport and concentration of the DNA chromophore units is extremely rapid; occurring in 1 to 2 seconds.

Figure 46C:
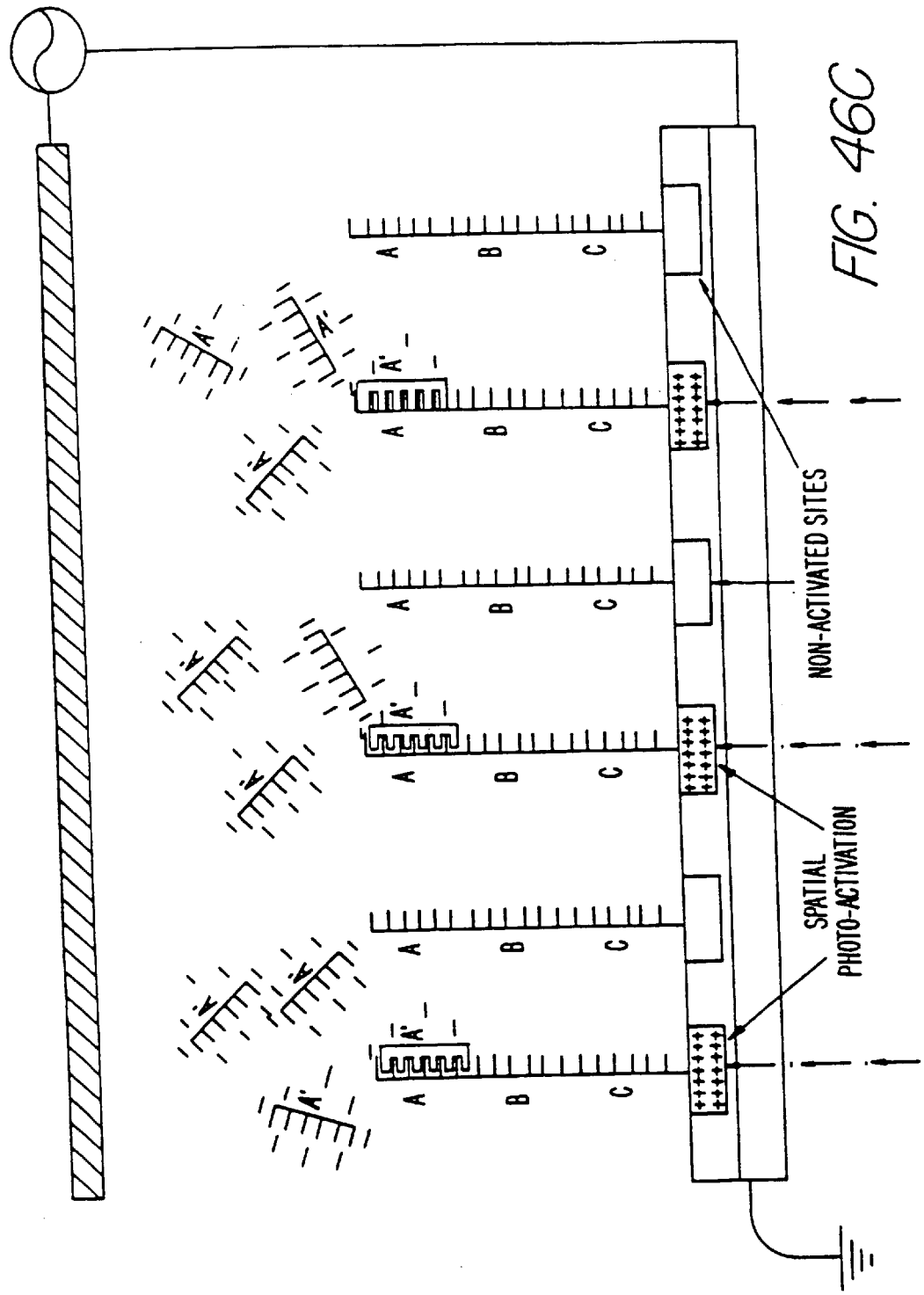
Figure 46D:
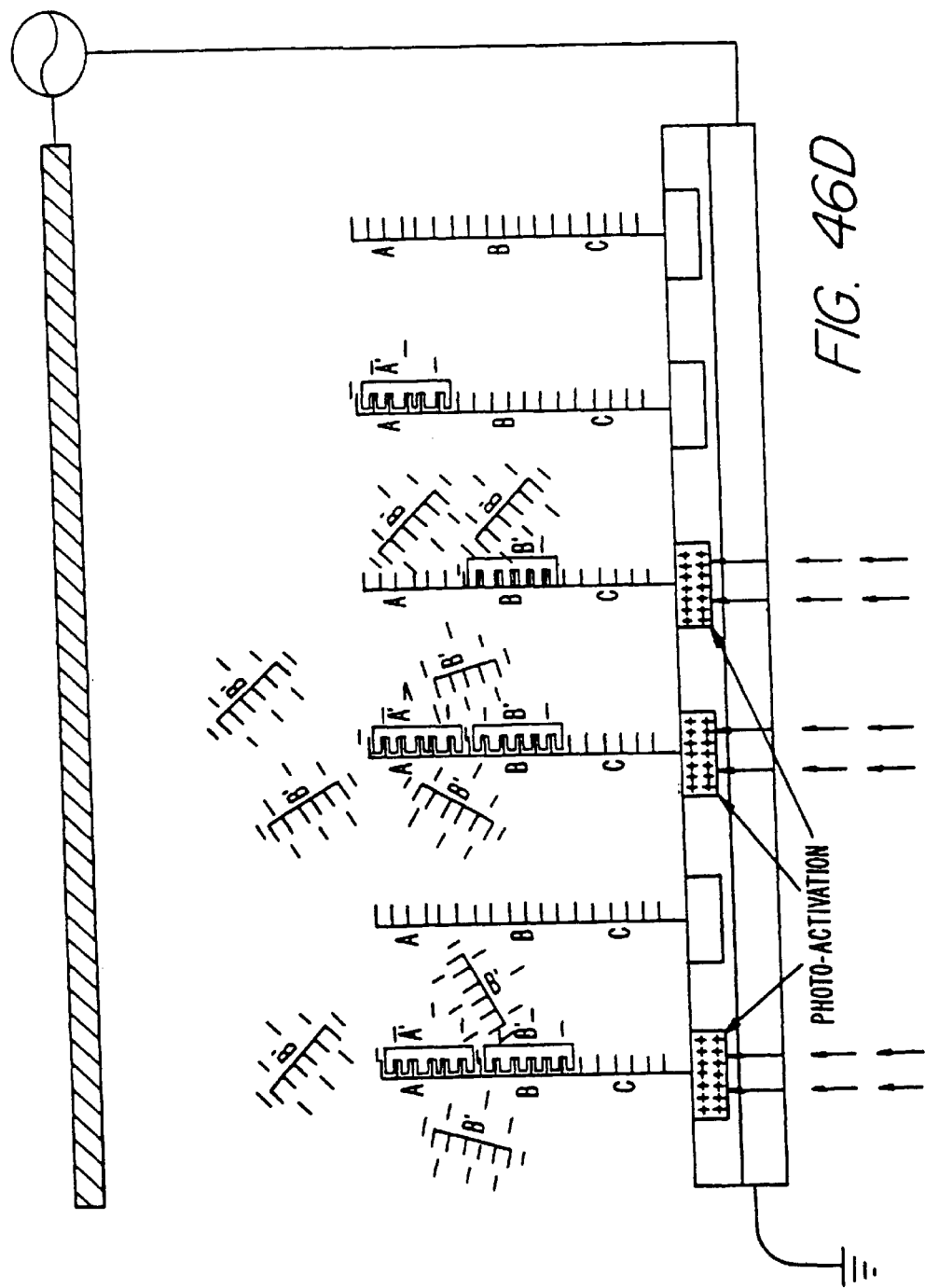
Figure 46E:
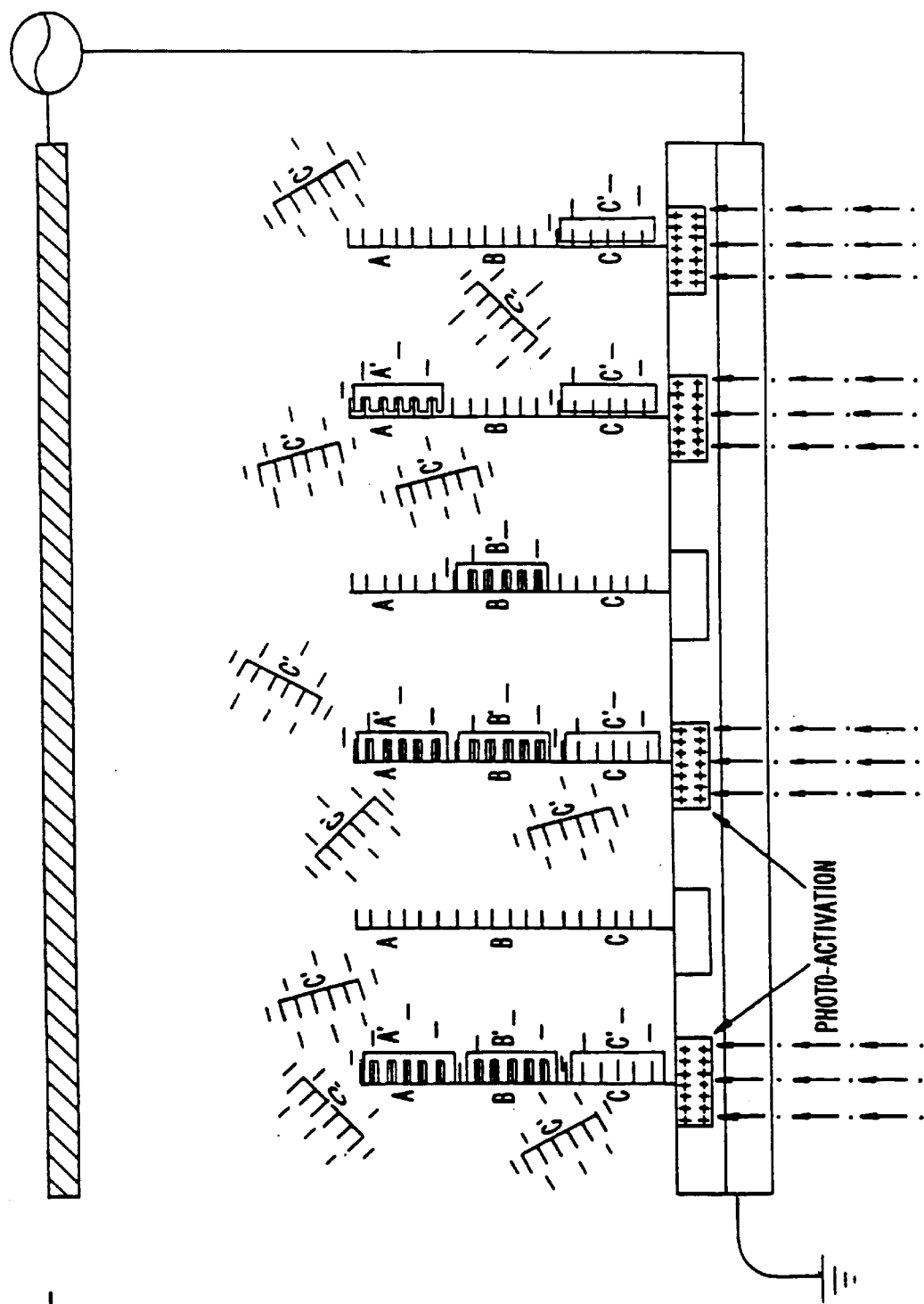
Figure 46F:
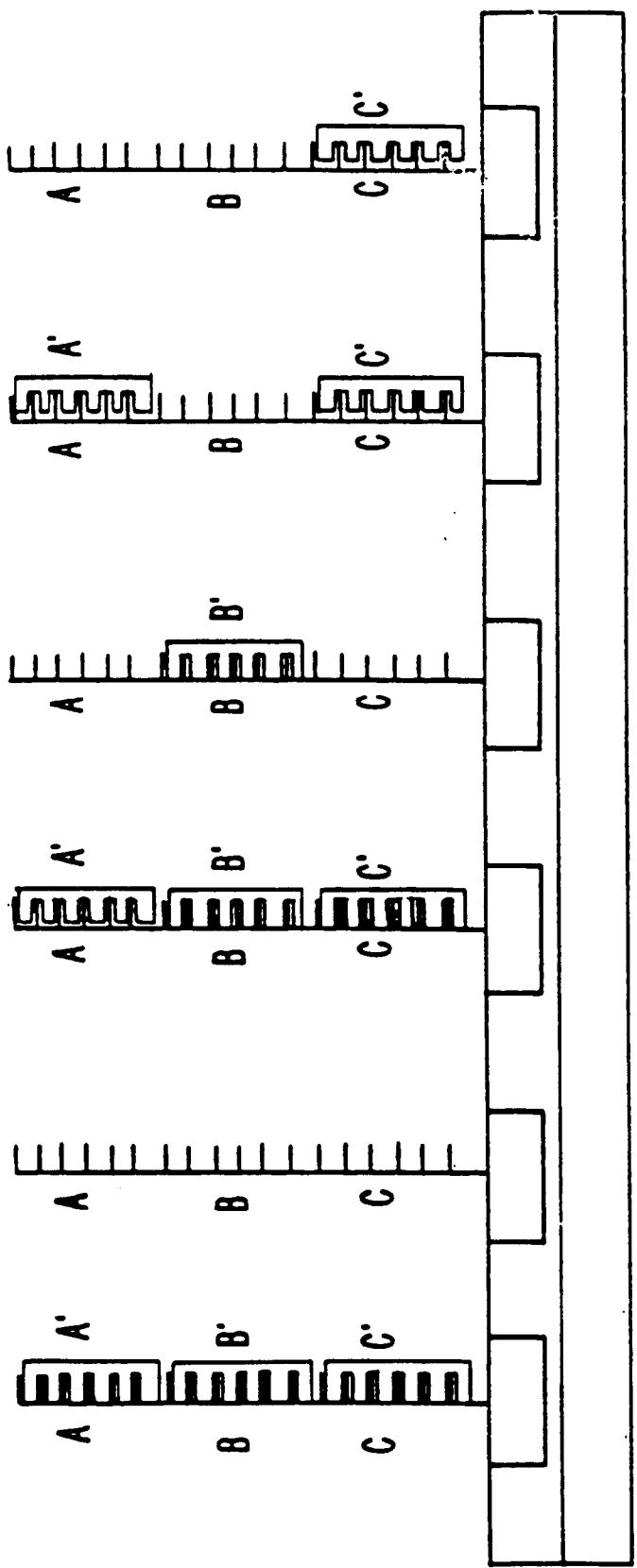

The process for producing multiple colors at a specific microlocations is shown in FIGS. 46C through 46F. FIG. 46C shows a group of six microlocations, each of which contains a DNA polymer with A, B, and C sequence identities (only one capture strand is shown in these figures). Spatial light addressing of positions 1, 3, and 5 is carried out. Chromophoric DNA A' sequences (red) are transported, concentrated, and hybridized selectively to these locations. FIG. 46D shows the process repeated for the next chromophoric DNA B' sequences (green). Spatial light addressing of positions 1, 3, and 4 are now carried out. Chromophoric DNA B' sequences are transported, concentrated, and hybridized selectively to these locations. FIG. 46E shows the process repeated for the next chromophoric DNA C' sequences (blue). Spatial light addressing of positions 1, 3, 5 and 6, are now carried out. Chromophoric DNA C' sequences are transported, concentrated, and hybridized selectively to these locations. The write process being complete, FIG. 46F shows the final optical material which now has chromophore DNA A'/B'/C' (red/green/blue) at microlocations 1 and 3, chromophoric DNA A'/C' (red/blue) at microlocation 5, chromophoric DNA B' (green) at microlocation 4, chromophoric DNA C' (blue) at microlocation 6, and no chromophoric DNA (no color) at microlocation 2.

In addition to the spatial light activation of photoconductive materials, other alternatives exist. For example, electrode array devices may be switched by spatial light addressing. In yet another example, electrode arrays may be switched by electronics.

Photowrite Systems of FIGS. 47–52 Experimental Section

I. Silicon substrate preparation. N-type single crystal silicon wafers of (100) and (111) orientation and resistivities ranging between 0.1–0.9 Ohm–cm and 1–4 Ohm–cm were received from various commercial sources. The wafers were provided with an ohmic back contact by deposition of either a 300 nm aluminum layer (thermal evaporation) or a 50 nm platinum (sputter deposition) layer followed by thermal annealing. Annealing steps were performed under nitrogen at 300 C for 1 hr for aluminum layers and at 500 C for 45 min for platinum layers. Amorphous silicon surfaces were obtained by sputter deposition of 50 nm silicon onto oxide stripped (buffered HF) n-type single crystal wafers with ohmic back contacts.

The following procedure for deposition of $Mn_2O_3$ layers was modified from the original procedure published by Kainthla et al.: Individual samples of single crystal or amorphous silicon with dimensions of about 1 $cm^2$ were cut from the respective wafers and sonicated in acetone followed by rinsing with isopropanol and water. (Alternatively, larger samples can be pre-scribed with a diamond scribe and broken into individual pieces after deposition of the $Mn_2O_3$ layer.) After drying, the samples were placed in plastic petri dishes and treated with buffered HF (2 min) to strip the native oxide layer. Immediately after thorough rinsing with deionized water the sample surfaces were sensitized by exposure (2 min) to an aqueous solution containing 1 wt % $SnCl_2$ (Aldrich) and 4 vol % HCl. This step was followed by rinsing with 4 vol % HCl and deionized water. The sensitized surfaces were then decorated with Pd islands by immersion (2 min) in an aqueous solution containing 1 vol % HCl and 0.05 wt % $PdCl_2$ (Aldrich). Traces of $Sn^{4+}$ were removed by soaking in 5% HCl for 5 min followed by rinsing with deionized water. The deposition of the $Mn(OH)_2$ layer was performed by adding a freshly prepared aqueous solution containing 0.25 M $NH_4Cl$, 0.1 M $NH_4OH$ and 0.03 M $MnCl_2$ to the samples in the petri dish. Upon addition of the solution the petri dishes were placed on a shaker table for 10 min to allow vigorous stirring. A light brownish precipitate was observed to form within 30–60 sec. After completion of the deposition reaction, the samples were rinsed thoroughly with deionized water and dried in air. At this point, the sample surfaces have a slightly structured, brown-grayish appearance. The thermal conversion of $Mn(OH)_2$ into $Mn_2O_3$ was accomplished by heating the samples on a heating block in high vacuum ($10^{-5}$ to $10^{-6}$ torr) to 250 C for 15 min. The samples were left overnight to cool down to room temperature.

II. Permeation layer and DNA Oligonucleotide Synthesis. Preparation and spin deposition of the strepativridin loaded agarose permeation layer, as well as the synthesis of biotinylated and fluorescence labeled DNA oligonucleotides have been described previously.

Figure 47:
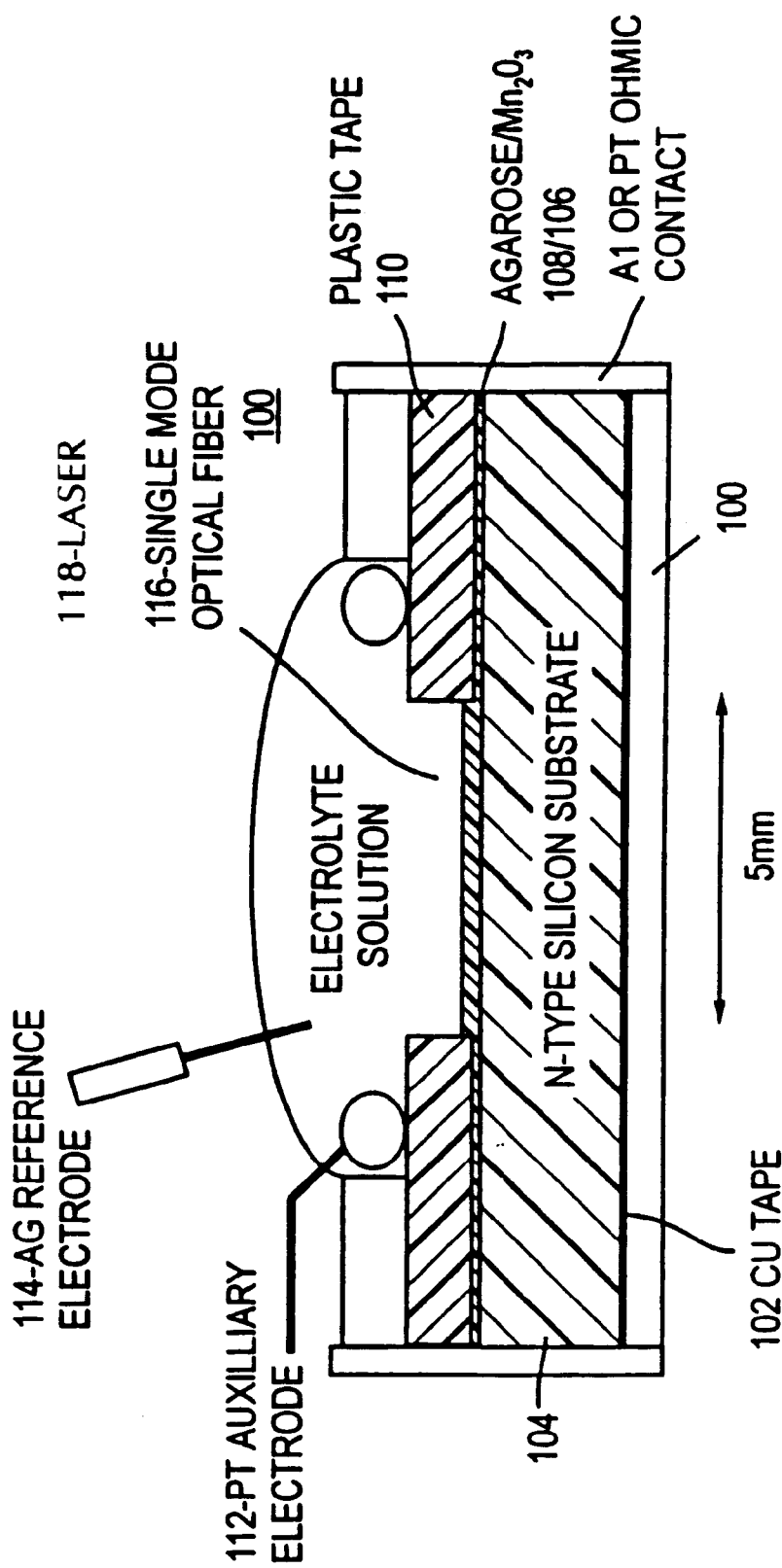
FIG. 47. Schematic cross-section of the electrochemical setup for photoelectrophoresis experiments.
Figure 48:
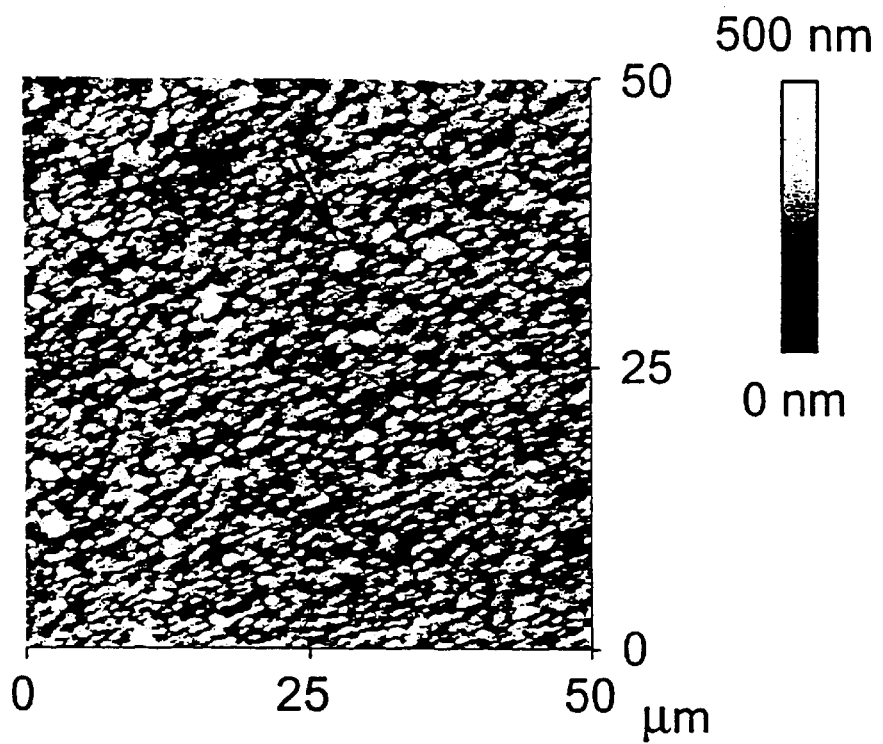
FIGS. 48A and B. Tapping mode AFM images of a $Mn_2O_3$ film deposited onto single crystal n-type silicon. The film thickness of this sample is approximately 270 nm with a medium roughness of 50 nm. a) Low-resolution image showing the oriented granular structure of the $Mn_2O_3$ film. Arrows indicate larger precipitates on the surface. b) High-resolution surface plot of the same sample.
Figure 48:
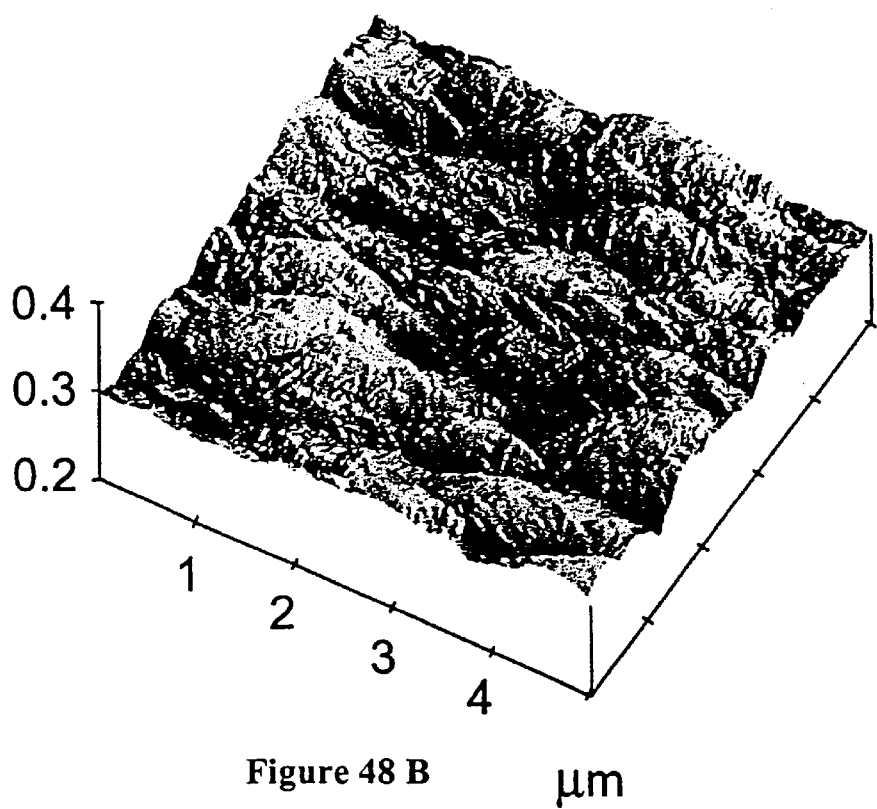
Figure 51:
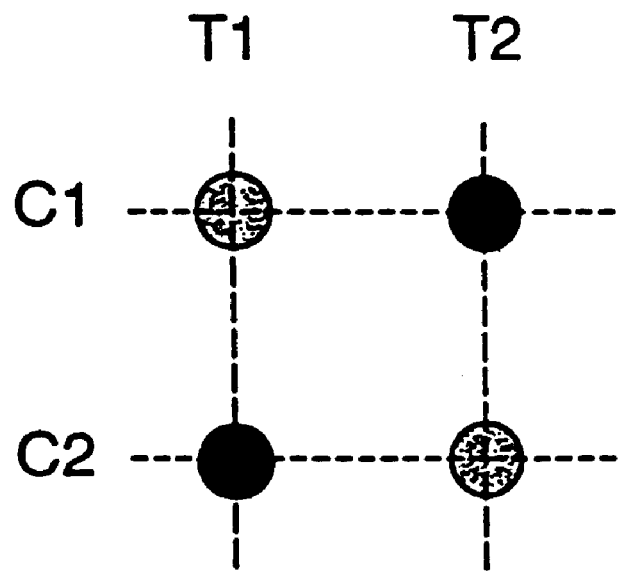
FIGS. 51A and B. Electronic DNA hybridization a) Schematic illustration of the process used for photoelectrophoretic transport and electronic hybridization of fluorescence labeled DNA oligonucleotides (C1, C2=capture oligonucleotides; T1, T2=target oligonucleotides). b) Fluorescence image of two sets of two spots with capture strands C1 and C2 after electronic hybridization with fluorescence labeled target strands T1 and T2. Fluorescence signals are only observed at the two locations with complementary capture and target strands. Oligonucleotides were deposited by illuminating individual spots with 4 W at an applied potential of 1.5 V. Illumination times were 15 sec for capture strands and 10 sec for target strands.
Figure 51:
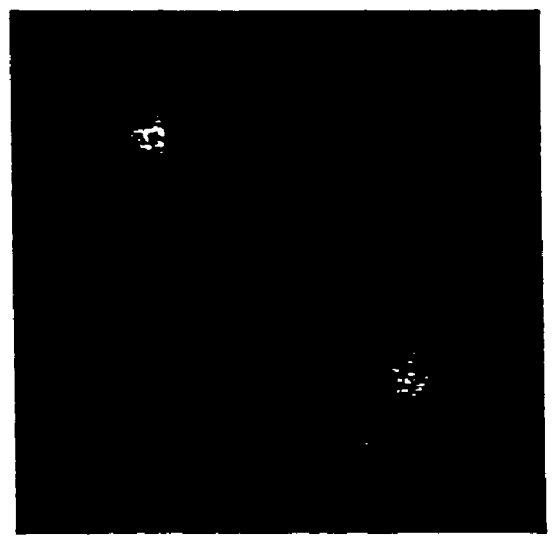

III. Experimental Setup FIG. 47 shows a cross-sectional view of a device capable of performing the photoelectric transport and hybridization of oligonucleotides of the present invention. An electrochemical cell 100 was constructed by first attaching a stripe of conducting material 102, preferably copper tape to a glass slide 100. A semiconductive substrate 104, such as an n-type silicon substrate, is disposed adjacent the conducting material 102. The $Mn_2O_3$ 106 and agarose coated silicon sample was then mounted onto the Cu tape using conducting silver paint. The active electrode area was defined by attaching a sheet 110 (e.g., a 2 mm thin piece of teflon sheet) with a circular opening to the sample. The electrode area exposed to the light measured about 0.25 $cm^2$. The electrochemical cell was completed by placing a circular Pt auxiliary electrode 112 and a Ag quasi-reference electrode 114 above the sample surface. Sample illumination for photoelectrophoretic transport and hybridization was accomplished by an optical fiber 116, preferably a single-mode optical fiber (Oriel) that was mounted on a motorized micromanipulator stage (Eppendorf 5171) and coupled to a laser 118 such as a 8 mW 630 nm HeNe laser (Research Electro Optics) that was attenuated by a filter wheel (New Focus). Photoelectrochemical stability measurements were performed by illuminating the whole sample area with a halogen light source (Bausch & Lomb).

IV. Instrumentation. Electrochemical experiments were performed either with a Pine AFRDE5 or an Autolab PGSTAT10 potentiostat system. Fluorescence signals were measured either on a high-resolution fluorescence scanner (Avalanche, Molecular Dynamics) or on a cooled CCD camera (Princeton Instruments). Surface morphologies and film thickness were recorded with a commercial atomic force microscope (Nanoscope III, Digital Instruments).

V. Assay procedure. A solution containing 50 nM of a DNA oligonucleotide in 50 mM of L-histidine (electrolyte) was pipetted into the electrochemical cell. The single mode optical fiber (not illuminated) was then placed above the sample surface and a constant electrochemical potential was applied to the cell (typically 1.5–2 V vs. $Ag/Ag^+$). Transport and/or hybridization of the DNA oligonucleotides were induced by illuminating the sample surface for 5–60 seconds with a light power of 4–80 W. In between runs with different DNA oligonucleotides, the cell was rinsed three times with 50 mM L-histidine. At the end of hybridization experiments, an additional rinse with 0.1 M phosphate buffer pH 7.4 containing 1% sodium dodecyl sulfonate was performed to reduce non-specific background.

Bead transport experiments were performed with thoroughly washed 1 m diameter carboxylated polystyrene beads (Bangs) in 50 mM L-histidine.

Results and Discussion

I. Silicon surface preparation

The original procedure for surface protection of n-type single crystal silicon surfaces with $Mn_2O_3$ layers published by Kainthla et al. (Kainthla, R. C.; Zelenay, B.; Bockris, J. O. M. *j. Electrochem. Soc.* 1986, 133, 248–253) involved a stain etch pretreatment ($HF:HNO_3:HCl$) followed by electrochemical deposition of a Pd monolayer and deposition of a $Mn(OH)_2$ precursor film from solution. The $Mn(OH)_2$ film was then converted into $Mn_2O_3$ by heating in high vacuum. Kainthla et al. developed the $Mn_2O_3$ system for photovoltaic applications where long-term stability and high current densities are desired. However, we were interested in a platform with good short-term stability that supports high current densities and provides good lateral resolution. The last point raised concerns that insufficient control over the thickness of the Pd seed layer would produce excessive lateral conductivity and consequently poor resolution. We also found that the electrodeposition of Pd seed layers on silicon substrates was problematic in general, thus leading to large variations in surface stabilization by $Mn_2O_3$ films. For this reason, we decided to deposit the Pd seed layers chemically, rather than electrochemically. Procedures to accomplish this are well known and have been used for many years to catalyze electroless plating of a variety of metals. See, e.g., Paunovic, M.; Schlesinger, M. "*Fundamentals of Electrochemical Deposition*"; Electrochemical Society; 1982.

In short, the surfaces to be plated are sensitized in a first step by adsorption of $Sn^{2+}$ ions. In a second step, the $Sn^{2+}$ ions are used to reduce $Pd^{2+}$ to metallic Pd, thereby producing a submonolayer of Pd. This change in deposition of the Pd monolayer allowed us also to omit the recommended but undesirable stain-etch pretreatment that was part of the original procedure by Kainthla et al.

A further modification involved the actual $Mn(OH)_2$ deposition step. It was observed that the use of 1.4 M $NH_4OH$ leads to immediate precipitation of $Mn(OH)_2$ and not to a gradual formation of a light brown precipitate as described in the original paper. This rapid precipitation was found to introduce further irreproducible behavior that we were able to avoid by decreasing the $NH_4OH$ concentration to 0.1 M. The resulting surfaces still displayed a certain degree of visual inhomogeneity but had very reproducible photoelectrochemical characteristics.

FIGS. 48A and B show two tapping mode atomic force images of a typical $Mn_2O_3$ surface at 50 $\mu$m and 5 $\mu$m full scale, respectively. The surface has a granular structure with an average grain size of approximately 2 $\mu$m and a mean roughness of 50 nm (with a small number of larger precipitates). The grains exhibit a preferred orientation probably caused by fluid flow during solution deposition of the $Mn(OH)_2$ precursor film. Film thickness' obtained from step height measurements ranged from 250 to 350 nm. This is at least a factor of ten more than the thickness reported by Kainthla et al. The difference reflects the increased deposition rate of Mn(OH)$_2$ that is caused by the lower concentration of NH$_4$OH used in our procedure.

II. Photoelectrochemical Behavior

Previous work on microelectrode arrays has shown that 50 mM L-histidine in water is an ideal electrolyte for DNA oligonucleotide transport and electronic hybridization. Its low conductivity (<100 S/cm) allows for efficient electrophoretic transport of oligonucleotides at low current densities. In addition, the buffering capacity and the specific charge of histidine actively promote hybridization of the oligonucleotides during electronic assays. Consequently, all photoelectrochemicalmeasurements in this work were performed in solutions of 50 mM L-histidine.

Typical cyclic voltammograms of Mn$_2$O$_3$ coated silicon electrodes before and after deposition of the agarose permneation layer are shown in FIGS. 49A and B, respectively. The two sequences of consecutive scans show that Mn$_2$O$_3$ coatings deposited with our modified procedure stabilize the silicon surface against photocorrosion. That is, after an initial decrease of about 5–20%, photocurrents are stable for hours of continuous operation (>12 hrs). While we do not wish to be bound by this theory, the initial loss is probably due to rapid passivation of unprotected electrode areas such as pinholes. Dark current levels are typically 10 to 50 times smaller than photocurrents but tend to increase after deposition of the agarose permeation layer. Mn$_2$O$_3$ coated thin film amorphous silicon electrodes displayed very similar cyclic voltammograms compared to single crystal silicon electrodes. However, the amorphous silicon electrodes exhibited better performance in photoelectrophoresisexperiments, as will be discussed below.

III. Photoelectrophoretic Transport and Hybridization of DNA Oligonucleotides

The ability to photoelectrophoretically transport DNA oligonucleotides to specific locations on an agarose coated silicon substrate depends both on the ratio between photocurrent and dark current and on the degree of lateral diffusion of the photocurrent. Thus, a large dark current leads to reduced contrast between illuminated and non-illuminated areas and eventually to a reduced signal to background ratio during fluorescence detection. Lateral diffusion of the photocurrent on the other hand, reduces the spatial resolution that is otherwise limited by the spot size of the illumination source.

In general, dark current levels can be minimized by careful preparation of the semiconductor surface (avoiding large numbers of surface traps) and by working with a semiconductor with low to moderate conductivity. Photocurrent diffusion depends on the minority carrier diffusion length within the semiconductor depletion zone and, specifically for this platform, on the lateral electrical conductivity within the Pd and Mn$_2$O$_3$ layers. Minority carrier or hole diffusion lengths can be reduced to a few microns by using highly doped silicon substrates, however, this comes at the expense of higher dark currents. Minimal minority carrier diffusion lengths can also be achieved by using amorphous silicon substrates. The conductivity across the Pd layer is minimal as long as its thickness does not exceed a few monolayers. A much more difficult task is to assess how deposition and heating parameters affect the electrical and electrochemical properties of the Mn$_2$O$_3$ layers. The literature value for room temperature resistivity of dry, crystalline Mn$_2$O$_3$ is 10–100 Ohm–cm.

First studied was Mn$_2$O$_3$ protected single crystal silicon with 1–4 Ohm–cm resistivity coated with a layer of streptavidin-agarose. The DNA oligonucleotides (capture probe sequence C1, Table 1) were both biotinylated and fluorescence labeled (BTR 493/503 nm). Illumination of the electrode surface with 40–80 W for 15–120 seconds at an applied potential of 1.5 V resulted in easily detectable fluorescent spots. These spots did not wash off during rinsing as compared to non-biotinylated oligonucleotides, demonstrating that the biotinylated oligonucleotides were not only photoelectrophoretically transported to the illuminated locations but also bound to the streptavidin present in the agarose.

However, large variations in spot size and fluorescence intensity were observed for experiments run under identical conditions, and in some cases, no fluorescent signal was detected at all even though substantial photocurrents were generated. Since there was no clear correlation between photocurrents and detected fluorescence levels, it was suspected that the surfaces exhibited variable degrees of photocurrent spreading, preventing the detection of localized fluorescence signals. For this reason, silicon substrates with lower resistance and substrates with amorphous silicon coatings were investigated.

While a decrease in resistance (0.1 and 0.9 Ohm–cm) did not seem to enhance the reproducibility of DNA oligonucleotide binding, much improved results were obtained with amorphous silicon coated electrodes. For example, FIG. 50A shows an array of fluorescent oligonucleotide spots that was produced by successively illuminating nine individual locations on a streptavidin-agarose and Mn$_2$O$_3$ coated amorphous silicon sample. Although, there was still some non-uniformities in spot size and fluorescence intensity (40% standard deviation), fluorescent spots were reproducibly generated at any location on a given chip with signal to background ratios greater than 100. The average spot size was 45 $\mu$m, which is only marginally larger than the area illuminated by the optical fiber (the uncollimated light beam originating from the 8 $\mu$m diameter optical fiber is broadened to about 30 $\mu$m by scattering within the agarose layer). FIG. 50B shows the current transient recorded during formation of the array of fluorescent oligonucleotide spots. As can be seen, stability and reproducibility of the photocurrents recorded at different locations is excellent. Furthermore, the relatively low light levels and short illumination times sufficient to immobilize fluorescence labeled DNA oligonucleotides on amorphous silicon electrodes make it possible to use other fluorescent dyes with absorption maximums at higher wavelengths (e.g. BTR 588/616 or BTR 630/650). This was not possible under the conditions applied for single crystal silicon electrodes where severe photobleaching was observed for these dyes. At this point, it is not clear if the superior performance of the amorphous silicon samples is truly related to a reduction of the minority carrier diffusion length or to an improvement in the interface between the Mn$_2$O$_3$ layer and the underlying substrate.

In addition to photoelectrophoretic transport, electronic hybridization was investigated. In electronic hybridization one set of unlabeled oligonucleotides (capture strands) are first targeted to specific locations and anchored. A second set of fluorescence labeled oligonucleotides (target strands) is then targeted to the same locations and actively hybridized to the capture strands. In the example shown, two sets of biotinylated DNA capture probes (sequences C1 and C2, Table 1) were successively transported and anchored to four different locations on a streptavidin-agarose and Mn$_2$O$_3$ coated amorphous silicon substrate, as outlined in FIG. 51A. Two fluorescence labeled target strands (sequences T1 and T2) were then each transported to a location with complementary capture probes and a location with non-complementary capture probes. This step produced two clearly detectable fluorescence signals at the two locations with matching sequences (FIG. 51B). The ratio between signal and non-specific background was better than four.

Thus, this method allows for the detection of DNA oligonucleotides by electronic hybridization in an extremely short period of time which is a clear advantage over assays relying on passive hybridization. A further advantage is that a large number of different capture probes can be deposited in arbitrary patterns with arbitrary spot sizes in order to accommodate different kinds of sampling and imaging requirements.

IV. Photoelectrophoretic Transport of Beads

Figure 52:
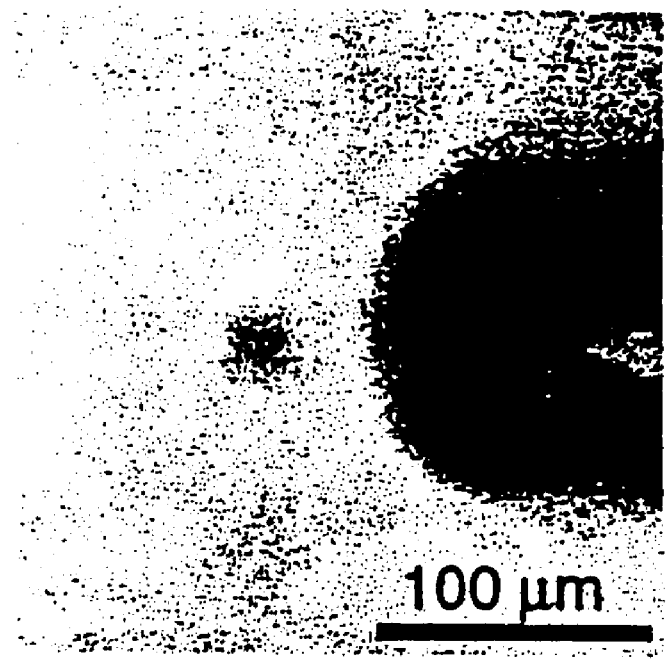
FIG. 52. Microphotograph of photoelectrophoretic bead accumulation on a $Mn_2O_3$ coated n-type single crystal silicon electrode. The accumulated 1 m beads appear as a dark spot next to the tip of the single mode optical fiber in the right half of the picture. Accumulation was performed by illuminating with 80 W for 1 min and scanning the applied potential between 0 V and 0.6 V (200 mV/sec).

As an expansion of the above methodology, we also performed photoelectrophoretic transport using negatively charged polystyrene beads on $Mn_2O_3$ coated single crystal silicon samples (1–4 Ohm–cm). FIG. 52 shows an example of localized bead aggregation induced by application of a scanned potential under illumination with the optical fiber. The diameter of the bead cluster is only slightly larger than the illuminated spot size of about 20 μm (no agarose), indicating minimal photocurrent spreading on this sample. The applied potential was scanned rather than kept constant because it was observed that the beads adhered to the surface unless the potential was periodically lowered to 0 V. By slowly changing the position of the optical fiber, beads can also be transported across the surface. Potentially, this may be useful for micropositioning applications performed in aqueous or non-aqueous environments.

TABLE 1

Sequences of DNA oligonucleotides

| Name | Sequence |
| --- | --- |
| C1 | 5'-Bio-GAGAGCACATGAG(*)C |
| C2 (ATA5) | 5'-GATGAGCAGTTCTACGTGG-Bio |
| T1 | 5'-TGATACGGTG(493)TCTCGACTCATGTGCTCTC |
| T2 (RCA5) | 5'-(493)CCACGTAGAACTGCTATC |

*= $NH_2$ or fluorescent dye
bio = Biotin
493: fluorescent dye with 493 nm absorption and 503 nm emission V. Conclusions We have shown that $Mn_2O_3$ stabilized n-type silicon photoelectrodes coated with a streptavidin-agarose permeation layer constitute a simple platform for rapid manipulation of DNA oligonucleotides by electronic hybridization. We have also shown that the same platform can be used for accumulation or transport of micron sized objects e.g. polystyrene beads, which could be ultimately employed in micropositioning or object sorting tasks.

We claim:

1. A device for effecting the photoelectric transport of charged materials in a liquid environment, comprising:
   a substrate having a first face and a second face, the substrate capable of generating a photocurrent;
   a conductor contacting at least a portion of the first face of the substrates
   a permeation layer supported on the second face, wherein the permeation layer comprises agarose;
   attachment entities coupled to the permeation layer; and
   a light source disposed to illuminate at least a portion of the substrate.

2. The device of claim 1 for effecting the photoelectric transport of charged materials in a liquid environment wherein the substrate is adapted to generate a photo-current.

3. The device of claim 1 for effecting the photoelectric transport of charged materials in a liquid environment wherein the substrate is adapted to generate a photo electrochemical current.

4. The device of claim 1 for effecting the photoelectric transport of charged materials in a liquid environment wherein the substrate is a semiconductor.

5. The device of claim 4 for effecting the photoelectric transport of charged materials in a liquid environment wherein the semiconductor is an n-type semiconductor.

6. The device of claim 4 for effecting the photoelectric transport of charged materials in a liquid environment wherein the semiconductor comprises silicon.

7. The device of claim 1 for effecting the photoelectric transport of charged materials in a liquid environment wherein the conductor contacting at least a portion of the first face of the substrate is a film.

8. The device of claim 7 for effecting the photoelectric transport of charged materials in a liquid environment wherein the film is a copper film.

9. The device of claim 1 for effecting the photoelectric transport of charged materials in a liquid environment further including a chemical layer supported on the substrate.

10. The device of claim 9 for effecting the photoelectric transport of charged materials in a liquid environment wherein the chemical layer includes $Mn_2O_3$.

11. The device of claim 10 for effecting the photoelectric transport of charged materials in a liquid environment further including a metal layer disposed between the substrate and the chemical layer.

12. The device of claim 11 for effecting the photoelectric transport of charged materials in a liquid environment wherein the metal layer disposed between the substrate and the chemical layer is palladium.

13. The device of claim 1 for effecting the photoelectric transport of charged materials in a liquid environment further including a containment structure disposed in fixed relation with the substrate.

14. The device of claim 13 for effecting the photoelectric transport of charged materials in a liquid environment wherein the containment structure includes a sheet like containment system having an aperture through the sheet.

15. The device of claim 14 for effecting the photoelectric transport of charged materials in a liquid environment wherein the sheet is a polytetrafluoroethylene sheet.

16. The device of claim 1 for effecting the photoelectric transport of charged materials in a liquid environment further including a optical fiber disposed between the light source and the device.

17. The device of claim 16 for effecting the photoelectric transport of charged materials in a liquid environment wherein the optical fiber is a single mode optical fiber.

18. The device of claim 1 for effecting the photoelectric transport of charged materials in a liquid environment wherein the light source includes a laser.

19. A device for effecting the photoelectric transport of charged materials in a liquid environment, comprising:
    a photoconductor substrate;
    a permeation layer supported on the substrate, wherein the permeation layer comprises agarose;
    attachment entities coupled to the permeation layer; and
    a light source disposed to illuminate at least a portion of the substrate.

20. The device of claim 19 for effecting the photoelectric transport of charged materials in a liquid environment, further comprising at least one conductor disposed above the photoconductor substrate.

21. The device of claim 20 for effecting the photoelectric transport of charged materials in a liquid environment, wherein the at least one conductor comprises an auxiliary electrode and a reference electrode.

22. The device of claim 21 for effecting the photoelectric transport of charged materials in a liquid environment, wherein auxiliary electrode is a Platinum electrode and the reference electrode is a Silver electrode.

23. The device of claim 19 for effecting the photoelectric transport of charged materials in a liquid environment, wherein the substrate is a semiconductor.

24. The device of claim 23 for effecting the photoelectric transport of charged materials in a liquid environment, wherein the semiconductor is an n-type semiconductor.

25. The device of claim 23 for effecting the photoelectric transport of charged materials in a liquid environment, wherein the semiconductor comprises silicon.

26. The device of claim 19 for effecting the photoelectric transport of charged materials in a liquid environment, wherein the conductor contacting at least a portion of the first face of the substrate is a film.

27. The device of claim 26 for effecting the photoelectric transport of charged materials in a liquid environment, wherein the film is a copper film.

28. The device of claim 19 for effecting the photoelectric transport of charged materials in a liquid environment, further including a chemical layer supported on the substrate.

29. The device of claim 28 for effecting the photoelectric transport of charged materials in a liquid environment, wherein the chemical layer includes $Mn_2O_3$.

30. The device of claim 29 for effecting the photoelectric transport of charged materials in a liquid environment, further including a metal layer disposed between the substrate and the chemical layer.

31. The device of claim 30 for effecting the photoelectric transport of charged materials in a liquid environment, wherein the metal layer disposed between the substrate and the chemical layer is palladium.

32. The device of claim 19 for effecting the photoelectric transport of charged materials in a liquid environment, further including a containment structure disposed in fixed relation with the substrate.

33. The device of claim 32 for effecting the photoelectric transport of charged materials in a liquid environment, wherein the containment structure includes a sheet like containment system having an aperture through the sheet.

34. The device of claim 33 for effecting the photoelectric transport of charged materials in a liquid environment, wherein the sheet is a polytetrafluoroethylene sheet.

35. The device of claim 19 for effecting the photoelectric transport of charged materials in a liquid environment, further including an optical fiber disposed between the light source and the device.

36. The device of claim 35 for effecting the photoelectric transport of charged materials in a liquid environment, wherein the optical fiber is a single mode optical fiber.

37. The device of claim 19 for effecting the photoelectric transport of charged materials in a liquid environment, wherein the light source includes a laser.

38. The device of claim 19 for effecting the photoelectric transport of charged materials in a liquid environment, wherein the substrate comprises a chemically stabilized semiconductor, photoconductor, or photodiode.

39. The method for the photoelectric transport of charged materials in a liquid environment, comprising the steps of:
    providing a photoconductor substrate with a permeation layer disposed thereon, wherein the permeation layer comprises agarose;
    contacting a charged material in a liquid environment in a region spaced apart from the photoconductor substrate by a permeation layer;
    applying a voltage to at least one conductor, the at least one conductor positioned above the photoconductor substrate in contact with the liquid environment; and
    illuminating at least a portion of the photoconductor substrate with a light source.

40. The method of claim 39, wherein the charged entity is a nucleic acid.

41. The method of claim 39, further including an optical fiber disposed between the light source and the photoconductor substrate.

42. The method of claim 41, wherein the optical fiber is a single mode optical fiber.

43. The method of claim 41, wherein the light source includes a laser.

44. The method of claim 39, wherein the substrate comprises a chemically stabilized semiconductor, photoconductor, or photodiode.

45. The method of claim 39, wherein the at least one conductor comprises an auxiliary electrode and a reference electrode.

46. The method of claim 39, wherein the auxiliary electrode is a Platinum electrode and the reference electrode is a Silver electrode.

47. The method of claim 39, wherein the photoconductor substrate is a semiconductor.

48. The method of claim 47, wherein the semiconductor is an n-type semiconductor.

49. The method of claim 47, wherein the semiconductor comprises silicon.

* * * * *

SEQUENCE LISTING

<160> NUMBER OF SEQ ID NOS: 12

<210> SEQ ID NO 1
<211> LENGTH: 20
<212> TYPE: DNA
<213> ORGANISM: Artificial
<220> FEATURE:
<223> OTHER INFORMATION: Synthetic Oligonucleotide

<400> SEQUENCE: 1
gcaccgattc gataccgtag                                                    20

<210> SEQ ID NO 2
<211> LENGTH: 20
<212> TYPE: DNA
<213> ORGANISM: Artificial
<220> FEATURE:
<223> OTHER INFORMATION: Synthetic Oligonucleotide

<400> SEQUENCE: 2
ctacggtatc gaatcggtgc                                                    20

<210> SEQ ID NO 3
<211> LENGTH: 20
<212> TYPE: DNA
<213> ORGANISM: Artificial
<220> FEATURE:
<223> OTHER INFORMATION: Synthetic Oligonucleotide

<400> SEQUENCE: 3
ttcaggcaat tgatcgtaca                                                    20

<210> SEQ ID NO 4
<211> LENGTH: 20
<212> TYPE: DNA
<213> ORGANISM: Artificial

```
<220> FEATURE:
<223> OTHER INFORMATION: Synthetic Oligonucleotide

<400> SEQUENCE: 4
tgtacgatca attgcctgaa                                              20

<210> SEQ ID NO 5
<211> LENGTH: 14
<212> TYPE: DNA
<213> ORGANISM: Artificial
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: Biotinylated at residue 1
<220> FEATURE:
<221> NAME/KEY: misc_feature
<222> LOCATION: (13)..(13)
<223> OTHER INFORMATION: NH2 or Fluorescent Dye attached at residue 13

<400> SEQUENCE: 5
gagagcacat gagc                                                    14

<210> SEQ ID NO 6
<211> LENGTH: 19
<212> TYPE: DNA
<213> ORGANISM: Artificial
<220> FEATURE:
<223> OTHER INFORMATION: Synthetic Oligonucleotide
<220> FEATURE:
<221> NAME/KEY: misc_feature
<222> LOCATION: (19)..(19)
<223> OTHER INFORMATION: Biotinylated at residue 19

<400> SEQUENCE: 6
gatgagcagt tctacgtgg                                               19

<210> SEQ ID NO 7
<211> LENGTH: 29
<212> TYPE: DNA
<213> ORGANISM: Artificial
<220> FEATURE:
<223> OTHER INFORMATION: Synthetic Oligonucleotide
<220> FEATURE:
<221> NAME/KEY: misc_feature
<222> LOCATION: (11)..(11)
<223> OTHER INFORMATION: Fluorescent dye with 493 nm absorption and 503
      nm emission attached at residue 11

<400> SEQUENCE: 7
tgatacggtg tctcgactca tgtgctctc                                    29

<210> SEQ ID NO 8
<211> LENGTH: 18
<212> TYPE: DNA
<213> ORGANISM: Artificial
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: Fluorescent dye with 493 nm absorption and 503
      nm emission attached at residue 1

<400> SEQUENCE: 8
ccacgtagaa ctgctatc                                                18

<210> SEQ ID NO 9
```

```
<211> LENGTH: 18
<212> TYPE: DNA
<213> ORGANISM: Artificial
<220> FEATURE:
<223> OTHER INFORMATION: Synthetic Oligonucleotide

<400> SEQUENCE: 9
accagcttaa tgttgcca                                                 18

<210> SEQ ID NO 10
<211> LENGTH: 20
<212> TYPE: DNA
<213> ORGANISM: Artificial
<220> FEATURE:
<223> OTHER INFORMATION: Synthetic Oligonucleotide

<400> SEQUENCE: 10
tggtcgaatt acaacggtag                                               20

<210> SEQ ID NO 11
<211> LENGTH: 10
<212> TYPE: DNA
<213> ORGANISM: Artificial
<220> FEATURE:
<223> OTHER INFORMATION: Synthetic Oligonucleotide

<400> SEQUENCE: 11
tacgtatgca                                                          10

<210> SEQ ID NO 12
<211> LENGTH: 10
<212> TYPE: DNA
<213> ORGANISM: Synthetic oligonucleotide

<400> SEQUENCE: 12
atgcatacgt                                                          10
```